(12) United States Patent
Fahrenkrug et al.

(10) Patent No.: US 8,309,791 B2
(45) Date of Patent: Nov. 13, 2012

(54) METHOD FOR PRODUCING A TRANSGENIC PIG USING A HYPER-METHYLATED TRANSPOSON

(75) Inventors: Scott C. Fahrenkrug, Minneapolis, MN (US); Daniel F. Carlson, Inver Grove Heights, MN (US); Aron M. Geurts, New Berlin, WI (US)

(73) Assignee: Recombinectics, Inc., Saint Paul, MN (US)

( * ) Notice: Subject to any disclaimer, the term of this patent is extended or adjusted under 35 U.S.C. 154(b) by 232 days.

(21) Appl. No.: 12/504,364

(22) Filed: Jul. 16, 2009

(65) Prior Publication Data

US 2010/0146655 A1    Jun. 10, 2010

Related U.S. Application Data

(60) Provisional application No. 61/081,293, filed on Jul. 16, 2008.

(51) Int. Cl.
*A01K 67/027* (2006.01)
*C12N 15/00* (2006.01)

(52) U.S. Cl. ............................................. 800/17; 800/25
(58) Field of Classification Search .................. None
See application file for complete search history.

(56) References Cited

U.S. PATENT DOCUMENTS

| | | | |
|---|---|---|---|
| 4,873,191 A | 10/1989 | Wagner et al. |
| 5,110,802 A | 5/1992 | Cantin et al. |
| 5,144,019 A | 9/1992 | Rossi et al. |
| 5,149,796 A | 9/1992 | Rossi et al. |
| 5,272,262 A | 12/1993 | Rossi et al. |
| 5,610,053 A | 3/1997 | Chung et al. |
| 5,731,178 A | 3/1998 | Sippel et al. |
| 5,750,380 A | 5/1998 | Itakura et al. |
| 5,985,661 A | 11/1999 | Rossi |
| 6,100,448 A | 8/2000 | Thompson et al. |
| 6,395,549 B1 | 5/2002 | Tuan et al. |
| 6,548,741 B2 | 4/2003 | DeSousa et al. |
| 6,562,570 B1 | 5/2003 | Rossi et al. |
| 6,613,752 B2 | 9/2003 | Kay et al. |
| 7,034,115 B1 | 4/2006 | Kawakami |
| 7,078,196 B2 | 7/2006 | Tuschl et al. |
| 7,176,304 B2 | 2/2007 | McSwiggen et al. |
| 7,195,916 B2 | 3/2007 | Qin et al. |
| 7,345,027 B2 | 3/2008 | Tolentino et al. |
| 7,399,586 B2 | 7/2008 | Klinghoffer et al. |
| 7,422,853 B1 | 9/2008 | Huang et al. |
| 7,423,142 B2 | 9/2008 | Vornlocher |
| 7,425,544 B2 | 9/2008 | Dobie et al. |
| 7,452,987 B2 | 11/2008 | Giese et al. |
| 7,459,547 B2 | 12/2008 | Zamore et al. |
| 7,507,810 B2 | 3/2009 | Karras et al. |
| 7,507,811 B2 | 3/2009 | Khvorova et al. |
| 7,517,864 B2 | 4/2009 | Vargeese et al. |
| 7,524,653 B2 | 4/2009 | Nichols et al. |
| 7,541,344 B2 | 6/2009 | Bhat et al. |
| 2003/0036056 A1 | 2/2003 | Rossi et al. |
| 2003/0119017 A1 | 6/2003 | McSwiggen |
| 2003/0124513 A1 | 7/2003 | McSwiggen |
| 2003/0125281 A1 | 7/2003 | Lewis et al. |
| 2003/0130186 A1 | 7/2003 | Vargeese et al. |
| 2003/0139363 A1 | 7/2003 | Kay et al. |
| 2003/0144239 A1 | 7/2003 | Agami et al. |
| 2003/0148519 A1 | 8/2003 | Engelke et al. |
| 2003/0153519 A1 | 8/2003 | Kay et al. |
| 2003/0157691 A1 | 8/2003 | Qin et al. |
| 2003/0166282 A1 | 9/2003 | Brown et al. |
| 2003/0166512 A1 | 9/2003 | Xie |
| 2004/0197910 A1 | 10/2004 | Cooper et al. |
| 2004/0203158 A1 | 10/2004 | Hackett et al. |
| 2005/0003542 A1 | 1/2005 | Kay et al. |
| 2005/0177890 A1 | 8/2005 | Kawakami |
| 2005/0241007 A1 | 10/2005 | Miskey et al. |
| 2005/0260270 A1 | 11/2005 | Lewis et al. |
| 2005/0266561 A1 | 12/2005 | Wells |
| 2006/0166282 A1 | 7/2006 | Singh et al. |
| 2006/0210977 A1 | 9/2006 | Kaminski |
| 2006/0233757 A1 | 10/2006 | Maury |
| 2007/0022485 A1 | 1/2007 | Takeda et al. |
| 2007/0204356 A1 | 8/2007 | Fraser |
| 2007/0219148 A1 | 9/2007 | Schaack et al. |
| 2008/0038308 A1 | 2/2008 | Miller et al. |
| 2009/0029934 A1 | 1/2009 | McCray et al. |
| 2009/0042297 A1 | 2/2009 | George, Jr. et al. |
| 2009/0169638 A1 | 7/2009 | Davis et al. |
| 2010/0105140 A1 | 4/2010 | Fahrenkrug et al. |

FOREIGN PATENT DOCUMENTS

| | | |
|---|---|---|
| WO | 92/06988 A1 | 4/1992 |
| WO | 95/19788 A1 | 7/1995 |
| WO | 99/46372 A2 | 9/1999 |
| WO | 00/60115 A2 | 10/2000 |
| WO | 02/44321 A2 | 6/2002 |
| WO | 02/097114 A2 | 12/2002 |
| WO | 03/008573 A2 | 1/2003 |
| WO | 03/020931 A2 | 3/2003 |
| WO | 03/056022 A2 | 7/2003 |
| WO | 03/066650 A2 | 8/2003 |
| WO | 03/068797 A2 | 8/2003 |
| WO | 03/070193 A2 | 8/2003 |
| WO | 03/070750 A2 | 8/2003 |
| WO | 03/070895 A2 | 8/2003 |
| WO | 03/070914 A2 | 8/2003 |
| WO | 03/070918 A2 | 8/2003 |
| WO | 2006/036975 A2 | 4/2006 |

OTHER PUBLICATIONS

Houdebine. The methods to generate transgenic animals and to control transgene expression. J. Biotechnology, 2002, vol. 98, pp. 145-160.*

(Continued)

*Primary Examiner* — Deborah Crouch
(74) *Attorney, Agent, or Firm* — Dardi & Herbert, PLLC; Curtis B. Herbert

(57) ABSTRACT

Transgenic artiodactyls are described as well as methods of making and using such artiodactyls.

8 Claims, 15 Drawing Sheets

OTHER PUBLICATIONS

Horie et al. Efficient chromosomal transposition of a Tc1/mariner-like transposon Sleeping Beauty in mice. PNAS, 2001, vol. 98, pp. 9191-9196.*

Onishi et al. Pig Cloning by Microinjection of Fetal Fibroblast Nuclei. Science, 2000, vol. 289, pp. 1188-1190.*

Park et al., "Sleeping Beauty transposition in the mouse genome is associated with changes in DNA methylation at the site of insertion", Genomics, 88:204-213 (2006).

Betzl et al., "Epigenetic modification of transgenes under the control of the mouse mammary tumor virus LTR: tissue-dependent influence on transcription of the transgenes", Biol. Chem. 377(11):711-9 (Nov. 1996).

Brem et al., Large Transgenic Animals In: Maclean N. Ed. Animals with Novel Genes. Cambridge, UK: Cambridge University, 1994:179-244.

Brummelcamp et al., A System for Stable Expression of Short Interfering RNA's in Mammalian Cells, Science, 296:550-553 (2002).

Carmell et al., "Germline transmission of RNA in mice", Nature Structural Biology, 10(2):91-92 (2003).

Cao et al.,"DNA constructs designed to produce short haripin, interfering RNAs in transgenic mice sometimes show early lethality and an interferon response", J. Appl. Genet. 46(2):217-225 (2005).

Cogoni et al., "Gene silencing in Neurospora crassa requires a protein homologous to RNA-dependent RNA polymerase", Nature, 399:166-169 (May 13, 1999).

Denti et al., "A New Vector, Based on the PolIII Promoter of the U1 snRNA Gene, for the Expression of siRNAs in Mammalian Cells", Molecular Therapy, 10(1):191-199 (Jul. 2004).

Eckhardt et al., "DNA methylation profiling of human chromosomes 6, 20 and 22", Nat. Genet. 38(12):1378-1385 (2006).

Fraser et al., "Precise excision of TTAA-specific lepidopteran transposons piggyBac (IFP2) and tagalong (TFP3) from the baculovirus genome in cell lines from two species of Lepidoptera", Insect Mol Biol, 5(2):141-151 (May 1996).

Gasior et al., "Alu-linked hairpins effecienlty mediate RNA interference with less toxicity than do H1-expressed short hairpin RNAs", Analytical Biochemistry, 349:41-48 (2006).

Grimm et al., Fatality in mice due to oversaturation of cellular microRNA/short hairpin RNA pathways, Nature, 441:537-541 (May 25, 2006).

Kunath et al., "Transgenic RNA interference in ES cell-derived embroys recapitulates a genetic null phenotype", Nature Biology, 21:559-561 (May 2003).

Lickert et al., "Baf60c is essential for function of BAF chromatin remodelling complexes in heart development", Nature, 432(7013):107-12 (Nov. 4, 2004).

Michalkiewicz et al., "Efficieint trasngenic rat production by a lentiviral vector", Am. J. Physiol. Heart Circ. Physiol., 293: H881-H894 (2007).

Miyagishi et al., "u6 promoter-driven siRNAs with four uridine 3' overhangs efficiently suppress targeted gene expression in mammalian cells", Nature Biotechnology, 19:497-500 (May 2002).

Nelson et al., tRNA regulation of gene expression: Interactions of an mRNA 5'-UTR with a regulatory tRNA, RNA, 12:1254-1261 (2006).

Noelle et al., "CD40 and its ligand, an essential ligand-receptor pair for thymus-dependent B-cell activation", Immunology Today, 13(11):431-433 (1992).

Palmer et al., "Stable knockdown of CFTR establishes a role for the channel in P2Y receptor-stimulated anion secretion", J. Cell Physiol. 206(3):759-770 (Mar. 2006).

Paul et al., "Effective expression of small interfering RNA in human cells", Nature Biotechnology, 29:505-508 (May 2002).

Peng et al., "A transgenic approach for RNA interference-based genetic screening in mice", PNAS, 103 (7):2252-2256 (Feb. 14, 2006).

Reynolds, "Rational siRNA design for RNA interference", Nat. Biotechnoly, 22(3):326-330 (2004).

Romano et al., "Quelling: transient inactivation of gene expression in Neurospora crassa by transformation with homologous sequences", Mol. Microbiol., 6(22):3343-3353 (Nov. 1992).

Scherer et al., "Approaches for the sequence-specific knockdown of mRNA", Nature Biotechnology, 21 (12):1457-1465(Dec. 2003).

Sui et al., "A DNA vector-based RNAi technology to suppress gene expression in mammalian cells", PNAS, 99 (8):5515-5520 (Apr. 16, 2002).

Summerton et al., "Morpholino Antisense Oligomers: Design, Preparation, and Properties", Antisense Nucleic Acid Drug Dev., 7(3):187-195 (Jun. 1997).

Thompson et al., "Germ line transmission and expression of a corrected HPRT gene produced by gene targeting in embryonic stem cells", Cell, 56(2):313-321 (Jan. 13, 1989).

Wakayama et al., "Full-term development of mice from enucleated oocytes injected with cumulus cell nuclei", Nature, 394(6691):369-374 (Jul. 23, 1998).

Wilmut et al., "Viable offspring derived from fetal and adult mammalian cells", Nature, 385(6619):810-813 (Feb. 25, 1997).

Yin et al., "siRNA agents inhibit oncogene expression and attenuate human tumor cells growth", Journal of Experimental Therapeutics and Oncology, 3:194-204 (2003).

Armstrong et al., "Epigenetic modification is central to genome reprogramming in somatic cell nuclear transfer", Stem Cells, 24:805-814 (2006).

Balciunas et al., "Harnessing a High Cargo-Capacity Transposon for Genetic Applications in Vertebrates", PLoS Genet 2006, 2(11):1715-1724 (Nov. 2006).

Baus et al., "Hyperactive Transposase Mutants of the Sleeping Beauty Transposon", Mol. Ther., 12(6):1148-1156 (Dec. 2005).

Chevalier-Mariette et al., "CpG content affects gene silencing in mice: evidence from novel transgenes", Genome Biology 4(9):R53-R53.11 (Aug. 14, 2003).

Cogoni et al., "Transgene silencing of the al-1 gene in vegetative cells of Neurospora is mediated by a cytoplasmic effector and does not depend on DNA-DNA interactions or DNA methylation", EMBO J., 15(12):3153-3163 (Jun. 17, 1996).

Deachapunya et al., "Insulin Stimulates Transepithelial Sodium Transport by Activation of a Protein Phosphatase That Increases Na-K Atpase Activity in Endometrial Epithelial Cells", J Gen Physiol, 114(4):561-574 (Oct. 1, 1999).

Dupuy et al., "Mammalian germ-line transgenesis by transposition", Proc. Natl. Acad. Sci. USA, 99(7):4495-4499 (Apr. 2, 2002).

Fire et al., "Potent and specific genetic interference by double-stranded RNA in Caenorhabditis elegans", Nature, 391(6669):806-811 (1998).

Geurts et al., "Gene Transfer into Genomes of Human Cells by the Sleeping Beauty Transposon System", Mol. Ther. 8(1):108-117 (2003).

Geurts et al., "Gene Mutations and Genomic Rearrangements in the Mouse as a Result of Transposon Mobilization from Chromosomal Concatemers", pIOS Genetics, 2:e156 (2006).

Guatelli et al., "Isothermal, in vitro amplification of nucleic acids by a multienzyme reaction modeled after retroviral replication", Proc. Natl. Acad. Sci. USA, 87(5):1874-1878 (1990).

Hackett et al., "Predicting preferential DNA vector insertion sites: implications for functional genomics and gene therapy", Genome Biol., :(Suppl 1)S12.1-S12.17 (2007).

Hasuwa et al., "Small interfering RNA and gene silencing in transgenic mice and rats", FEBS Lett. 532 (1-2):227-230 (Dec. 4, 2002).

Hofmann et al., "Efficient transgenesis in farm animals by lentiviral vectors", EMBO Rep., 4(11):1054-1060 (2003).

Kawakami, "Tol2: a versatile gene transfer vector in vertebrates", Genome Biology, 8 (Suppl. 1):S7 (Oct. 31, 2007).

Kennerdell et al., "Use of dsRNA-Mediated Genetic Interference to Demonstrate that frizzled and frizzled 2 Act in the Wingless Pathway" Cell, 95:1017-1026 (Dec. 23, 1998).

Lavitrano et al., "Efficient production by sperm-mediated gene transfer of human decay accelerating factor (hDAF) transgenic pigs for xenotransplantation", Proc. Natl. Acad. Sci. USA, 99(22):14230-14235 (Oct. 29, 2002).

Lavitrano et al., "Sperm-mediated gene transfer", Reprod. Fert. Develop., 18:19-23 (2006).

Leaver, "A family of Tc1-like transposons from the genomes of fishes and frogs: evidence for horizontal transmission", Gene, 271(2):203-214 (2001).

Li et al., "Defining the optimal parameters for hairpin-based knockdown constructs", RNA, 13:1765-1774 (2007).

Lickert, "Dissecting Wnt/beta-catenin signaling during gastrulation using RNA interference in mouse embryos", Development, 132(11):2599-609 (Jun. 2005).

Lo, "Transformation by iontophoretic microinjection of DNA: multiple integrations without tandem insertions", Mol. Cell. Biol. 3(10):1803-1814 (Oct. 1983).

Luthra et al., "Isothermal Multiple Displacement Amplification: A Highly Reliable Approach for Generating Unlimited High Molecular Weight Genomic DNA from Clinical Specimens", J. Mol Diagn, 6(3):236-242 (Aug. 2004).

McIntyre et al., "Design and cloning strategies for constructing shRNA expression vectors", BMC Biotechnology, 6 (1): 8 pages (Jan. 5, 2006).

Miskey et al., "The Frog Prince: a reconstructed transposon from Rana pipiens with high transpositional activity in vertebrate cells", Nucleic Acids Res., 31(23):6873-6881 (2003).

Miskey et al., "The Ancient mariner Sails Again: Transposition of the Human Hsmar1 Element by a Reconstructed Transposase and Activities of the SETMAR Protein on Transposon Ends", Mol. Cell. Biol., 27(12):4589-4600 (Jun. 2007).

Misquitta et al., "Targeted disruption of gene function in Drosophila by RNA interference (RNA-i): A role for nautilus in embryonic somatic muscle formation", Proc. Natl. Acad. Sci., USA, 96(4):1451-1456 (1999).

Ohlfest et al., "Phenotypic correction and long-term expression of factor VIII in hemophilic mice by immunotolerization and nonviral gene transfer using the Sleeping Beauty transposon system", Blood, 105 (7):2691-2698 (Apr. 2005).

Orban et al., Tissue- and site-specific DNA recombination in transgenic mice, Proc. Natl. Acad. Sci. USA, 89 (15):6861-6865 (Aug. 1992).

Papaioannou et al., "The preimplantation pig embryo: cell number and allocation to trophectoderm and inner cell mass of the blastocyst in vivo and in vitro", Development, 102(4):793-803 (Apr. 1988).

Park et al., "DNA methylation of Sleeping Beauty with transposition into the mouse genome", Genes to Cells, 10:763-776 (2005).

Pavlopoulus et al., "The DNA transposon Minos as a tool for transgenesis and functional genomic analysis in vertebrates and invertebrates", Genome Biology, 8(Suppl. 1):S2-S2.7, Oct. 31, 2007.

Pinard et al., "Assessment of whole genome amplification-induced bias through high-throughput, massively parallel whole genome sequencing", BMC Genomics, 7(216):21 pages (Aug. 23, 2006).

Rakyan et al., "DNA Methylation Profiling of the Human Major Histocompatibility Complex: A Pilot Study for the Human Epigenome Project", PLoS Biology, 2(12):2170-2182 (Dec. 2004).

Raymond et al., "Simple, quantitative primer-extension PCR assay for direct monitoring of microRNAs and short-interfering RNAs", RNA, 11(11):1737-1744 (Nov. 2005).

Schumacher et al., "Epigenetic and Genotype-specific Effects on the Stability of de Novo Imposed Methylation Patterns in Transgenic Mice", J. Biol. Chem., 275:37915-37921 (Aug. 22, 2000).

Szulc et al., "A versatile tool for conditional gene expression and knockdown", Nature Methods, 3(2):109-116 (Feb. 2, 2006).

Taxman et al., "Criteria for effective design, construction, and gene knockdown by shRNA vectors", BMC Biotechnol. 6(7):16 pages (Jan. 24, 2006).

Vallier et al., "An efficient system for conditional gene expression in embryonic stem cells and in their in vitro and in vivo differentiated derivatives", Proc Natl Acad Sci USA, 98(5):2467-2472 (Feb. 27, 2001).

Van Der Putten et al., "Efficient insertion of genes into the mouse germ line via retroviral vectors", Proc. Natl. Acad. Sci. USA, 82(18):6148-6152 (Sep. 15, 1985).

Wilbur et al., "RNA as a Source of Transposase for Sleeping Beauty-Mediated Gene Insertion and Expression in Somatic Cells and Tissues", Mol. Ther. 13(3):625-630 (Mar. 2006).

Wilson et al., "PiggyBac Transposon-mediated Gene Transfer in Human Cells", Mol Ther, 15(1):139-145 (Jan. 2007).

Wolf et al., "Transgenic technology in farm animals—progress and perspectives", Exp. Physiol., 85(6):615-625 (2000).

Wu et al., "piggyBac is a flexible and highly active transposon as compared to Sleeping Beauty, Tol2, and Most in mammalian cells", Proc Natl Acad Sci USA, 103(41):15008-15013 (Oct. 10, 2006).

Yusa et al., "Enhancement of Sleeping Beauty Transposition by CpG Methylation: Possible Role of Heterochromatin Formation", Molecular and Cellular Biology, 24(9):4004-4018 (May 2004).

Amarzguioui et al., "An algorithm for selection of functional siRNA Sequences", Biochem. Biophys. Res. Commun., 316:1050-1058 (Apr. 16, 2004).

Chen et al., "A new positive/negative selectable marker, putk, for use in embryonic stem cells", Genesis 28(1):31-35 (2000).

Cibelli et al., "Cloned Transgenic Calves Produced from Nonquiescent Fetal Fibroblasts", Science, 280:1256-1258 (May 22, 1998).

Filipiak et al., "Advances in transgenic rat production", Transgenic Res., 15(6):673-686 (2006).

Hyrup et al., "Peptide Nucleic Acids (PNA): Synthesis, properties and potential applications", Bioorgan. Med. Chem., 4(1):5-23 (Jan. 1996).

Kempken et al., "The hAT family: a versatile transposon group common to plants, fungi, animals, and man", Chromosoma 2001, 110(1):1-9.

Kiwaki et al., "Correction of Ornithine Transcarbamylase Deficiency in Adult spfash Mice and in OTC-Deficient Human Hepatocytes with Recombinant Adenoviruses Bearing the CAG Promoter", Human Gene Ther., 7(7):821-830 (May 1996).

Lois et al., "Germline Transmission and Tissue-Specific Expression of Transgenes Delivered by Lentiviral Vectors" Science, 295(5556):868-872 (Feb. 1, 2002).

Plasterk et al., "Resident aliens: the Tc1/mariner super-Family of transposable elements", Trends Gene, 15 (8):326-332 (Aug. 1, 1999).

Pravtcheva et al., "Transgene instability in mice injected with an in vitro methylated Igf2 gene", Mutat Res. 529 (1-2):35-50 (Aug. 23, 2003).

Sarker et al., "Molecular evolutionary analysis of the widespread piggyBac transposon family and related "domesticated" sequences", Mol Genet Genomics, 270(2):173-180 (Oct. 2003).

Weiss, "Hot prospect for new gene amplifier", Science, 254:1292-1293 (Nov. 29, 1991).

Xu et al., "CMV-β-Actin Promoter Directs Higher Expression from an Adeno-Associated Viral Vector in the Liver than the Cytomegalovirus or Elongation Factor 1α Promoter and Results in Therapeutic Levels of Human Factor X in Mice", Hum. Gene Ther., 12(5):563-573 (2001).

\* cited by examiner

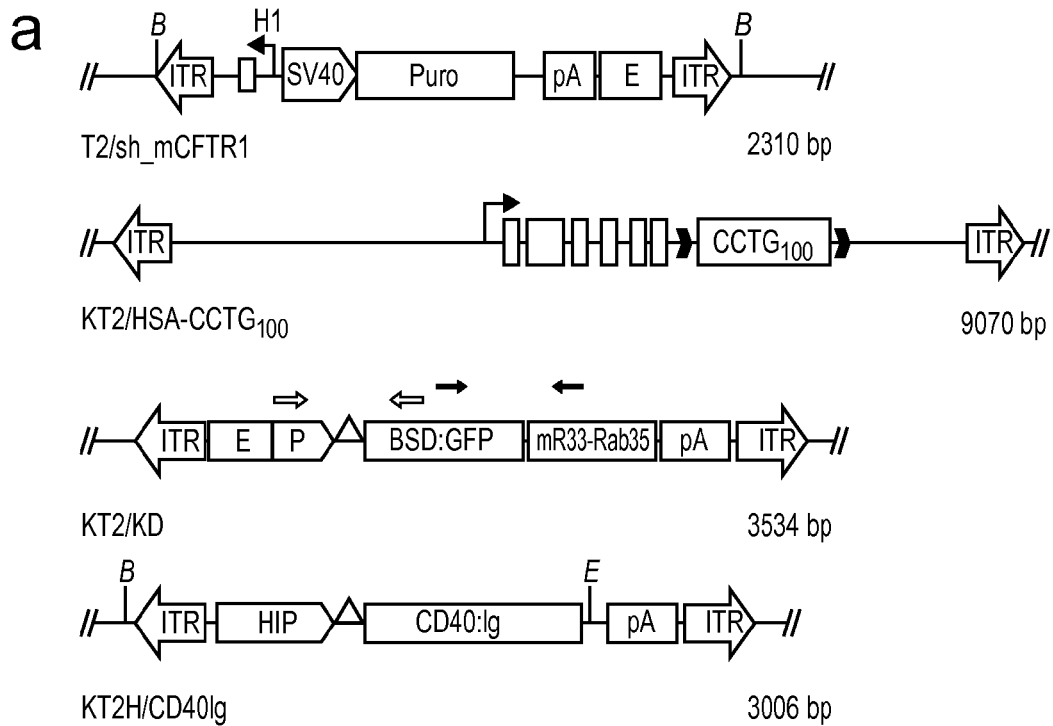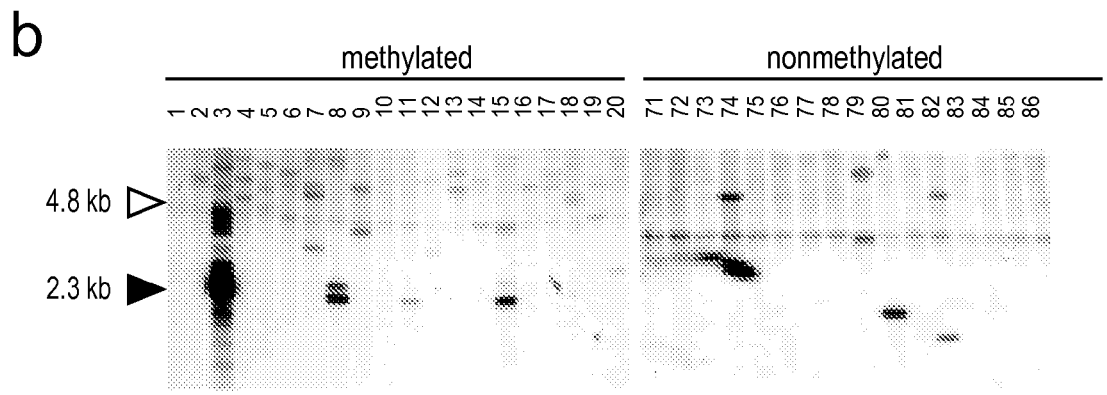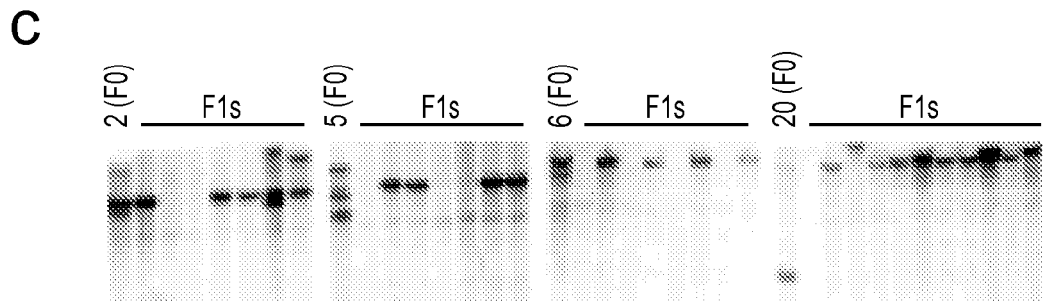
FIG. 1

FIGURE 3
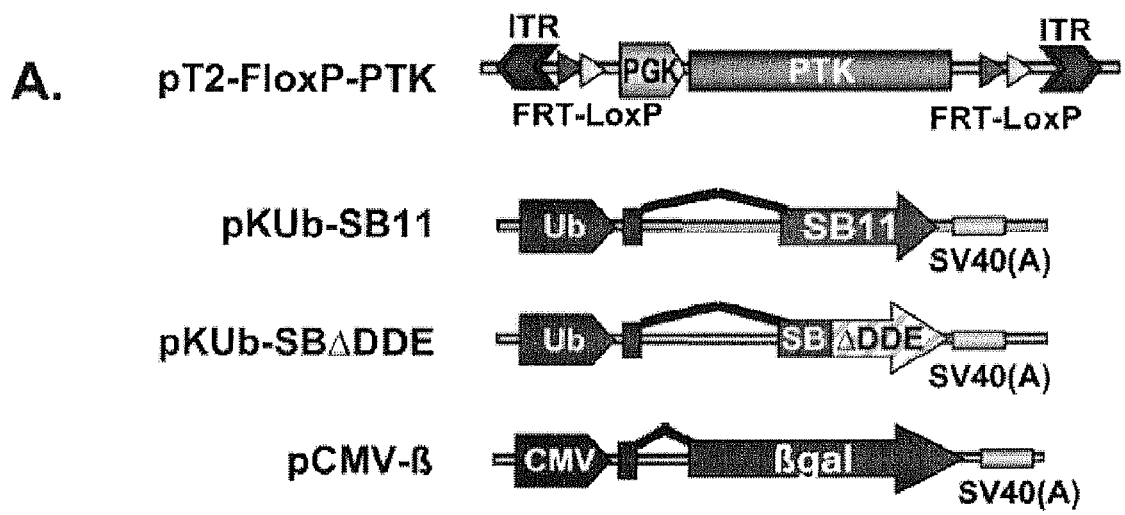
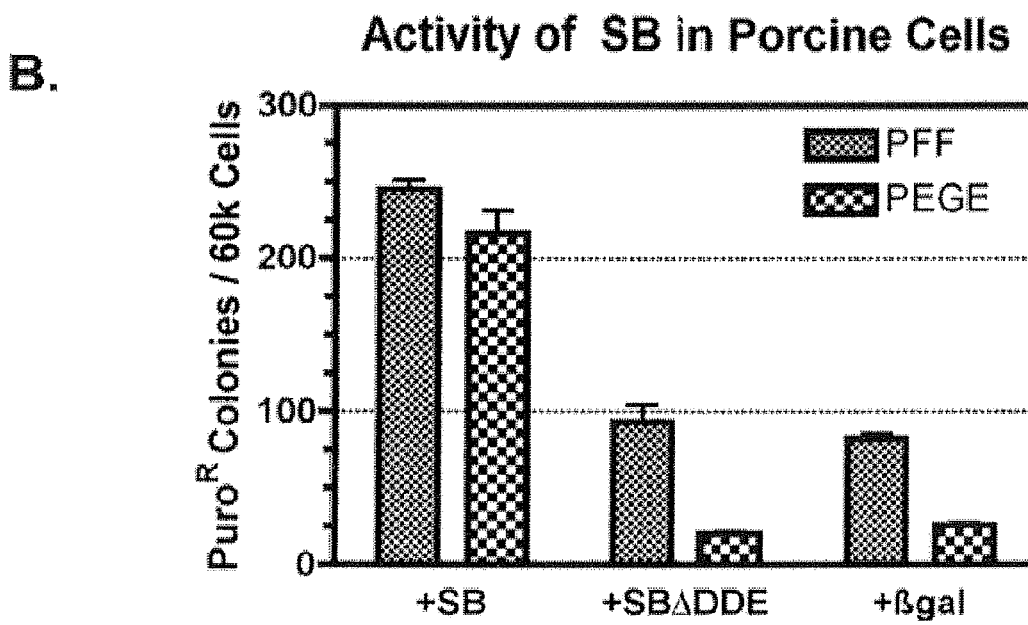

FIGURE 4
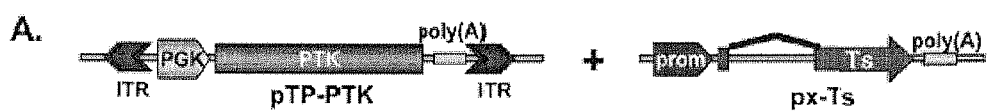
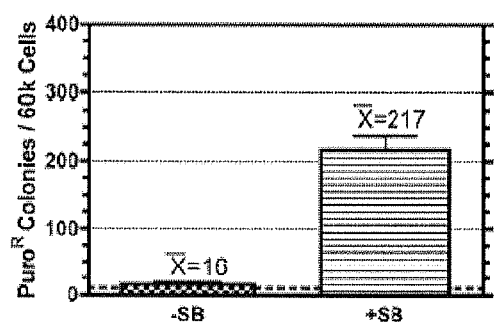
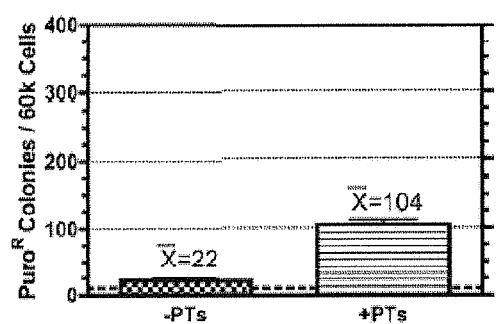
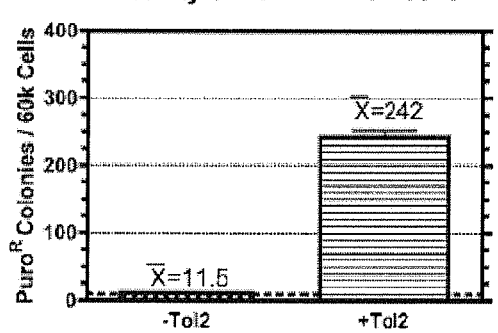
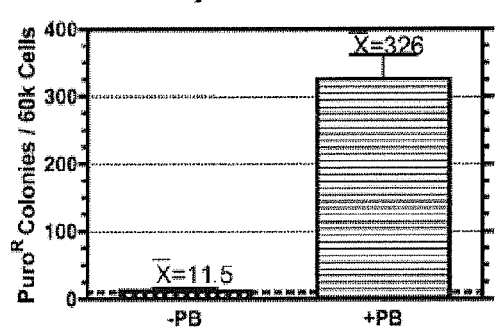

FIGURE 5                                         SEQ ID NO

| | | |
|---|---|---|
| gctggatccagatcccta | TA | CAGTTGAAGT | 82
| ATTGATATATAATTCACA | TA | CAGTTGAAGT | 83
| TCAATCATCACACTATGG | TA | CAGTTGAAGT | 84
| ATATTACAAGATATAT | TA | CAGTTGAAGT | 85
| GTAATGTTCCATTGTGTA | TA | CAGTTGGAGT | 86
| ACAAACAAGAACCACTAC | TA | CAGTTGAAGT | 87

| | | |
|---|---|---|
| CAAGGCACTG | TA | atcggtaccatttaaatc | 88
| CAAGGCACTG | TA | CTTGGGCAAGATGCTTAA | 89
| CAAGGCACTG | TA | TATCCTAATGCCTAGAGA | 90
| CAAGGCACTG | TA | ATCGGTACCCATGGTTGT | 91
| CAAGGCACTG | TA | TATTCAAGAAATCAAAAA | 92
| CAAGGCACTG | TA | TACGGTACCATTTGCTTG | 93

| | | |
|---|---|---|
| actatagggcga | ATTGGGCC | CAGAGGTGTA | 94
| GAGATTAAGGTG | CTAGTAGG | CAGAGGTGTA | 95
| ATGCTCAAGCCC | CCAGCCCC | CAGAGGTGTA | 96
| GACTTTAGCTAC | CTGCCCAG | CAGAGGTGTA | 97
| ACAACCAAGCCT | CCAAGGTC | CAGAGGTGTA | 98
| TCAAGTCAAGGA | GTCTCAAC | CAGAGGTGTA | 99

| | | |
|---|---|---|
| CTTTCTAGGG | TTAA | tctaggtaccatttaa | 100
| CTTTCTAGGG | TTAA | GCACAAACACTGCTGC | 101
| CTTTCTAGGG | TTAA | GAGCCCCTGCTCATC | 102
| CTTTCTAGGG | TTAA | CTTGATCAGAGATATA | 103
| CTTTCTAGGG | TTAA | TAGTTAGCAACAGCCT | 104
| CTTTCTAGGG | TTAA | ACTCTAGCATGGTTGT | 105

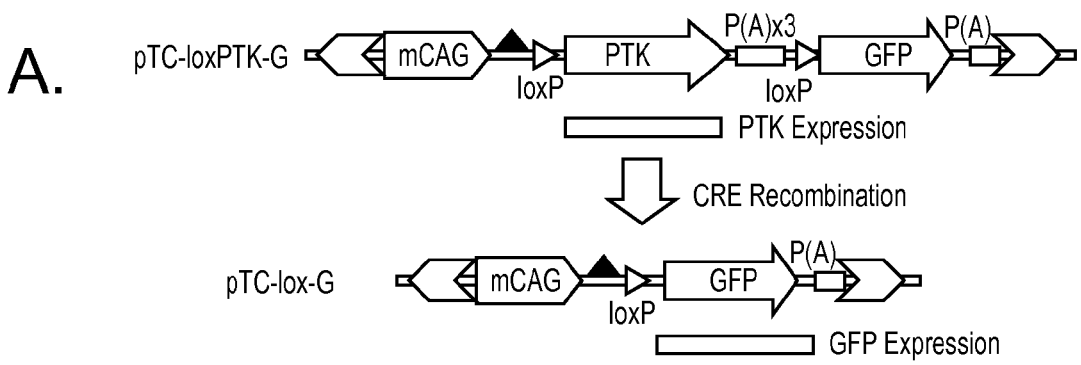
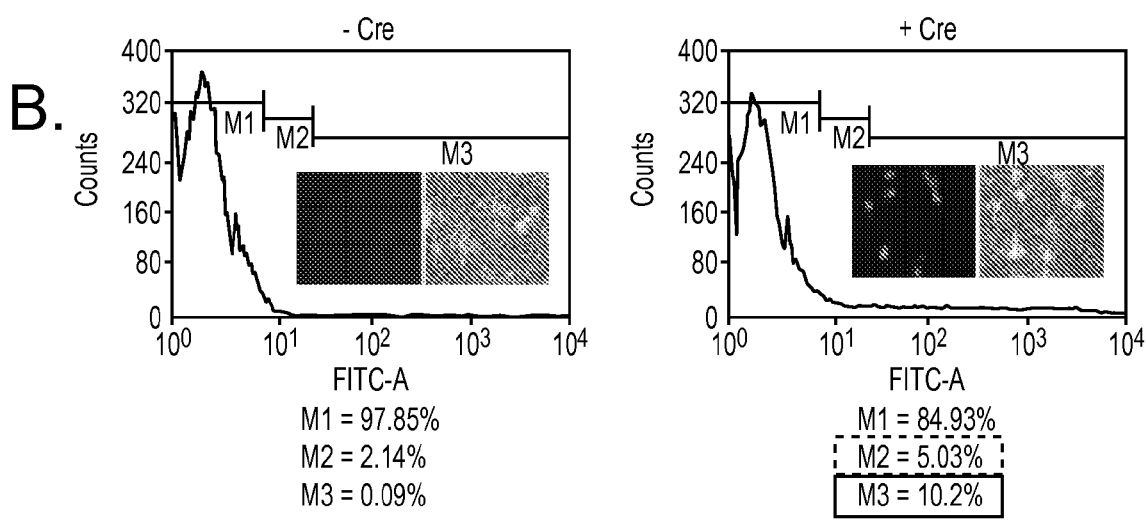
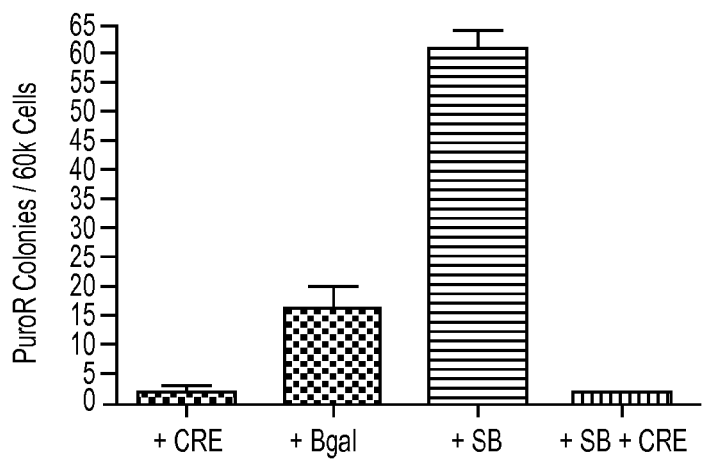
FIG. 8

FIGURE 9
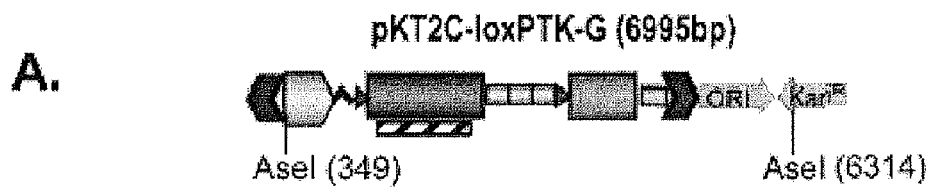
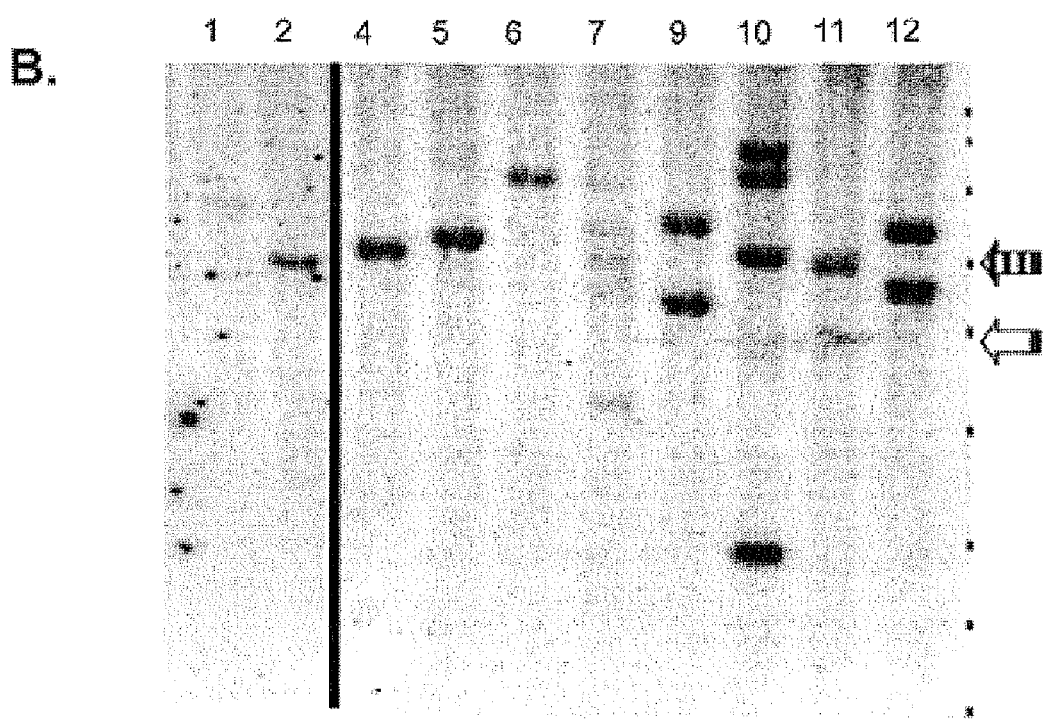
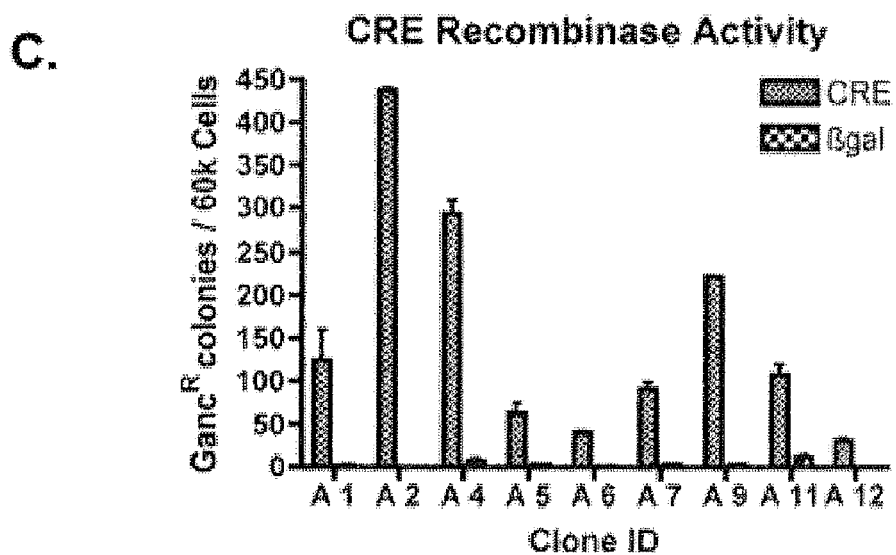

FIGURE 12A-B
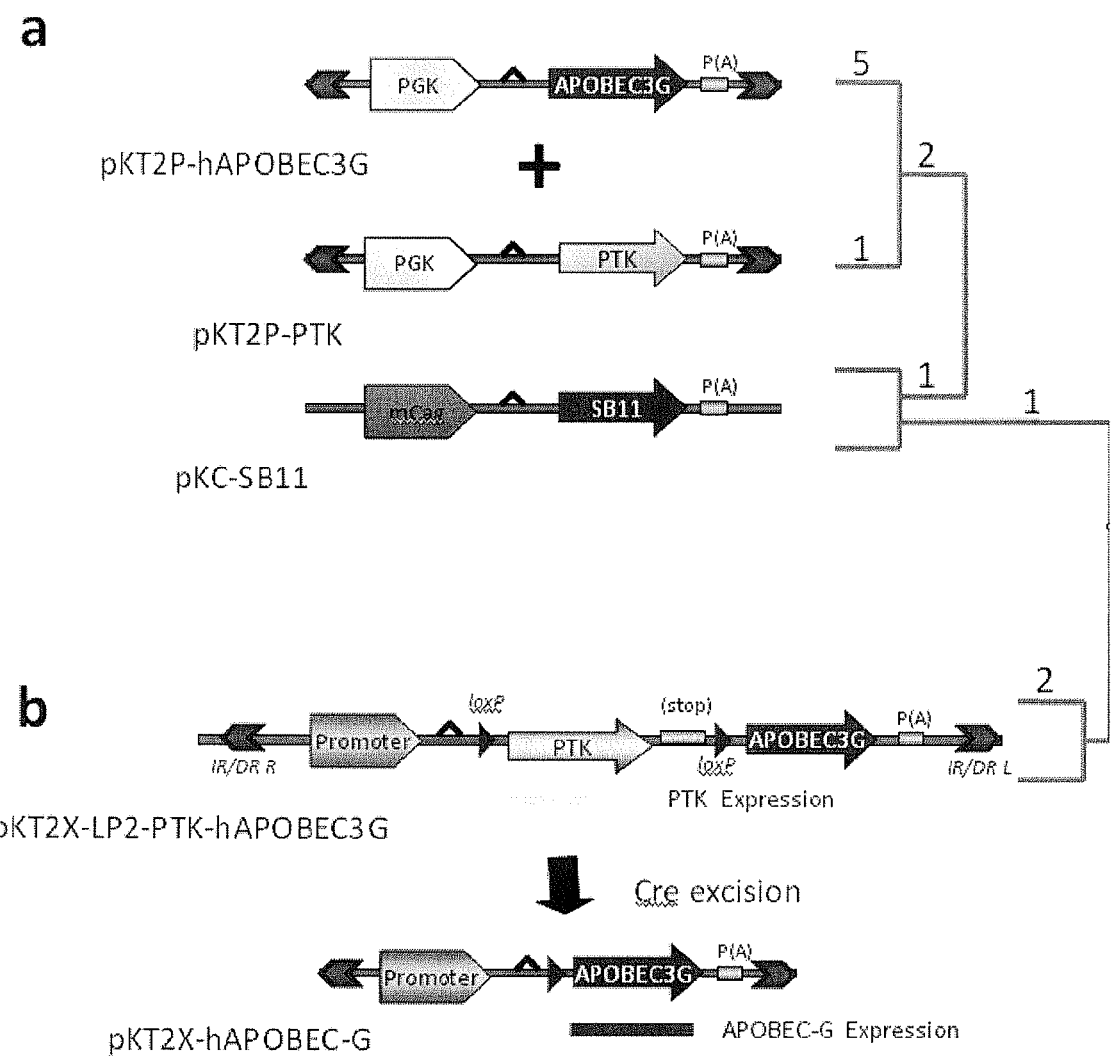

FIGURE 13
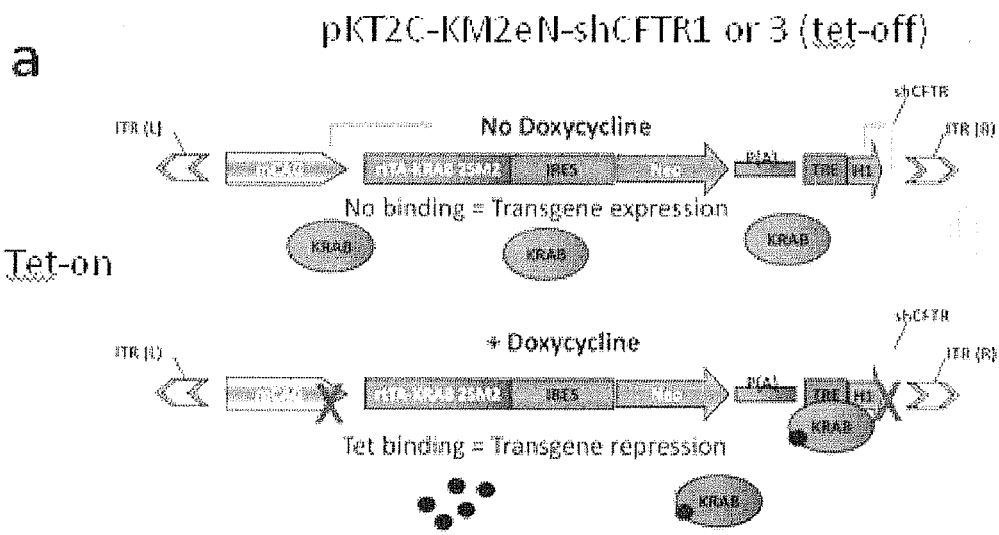
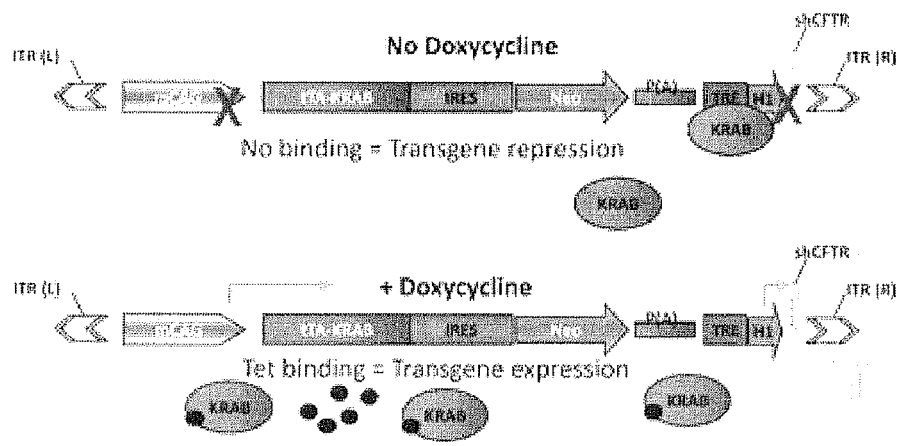
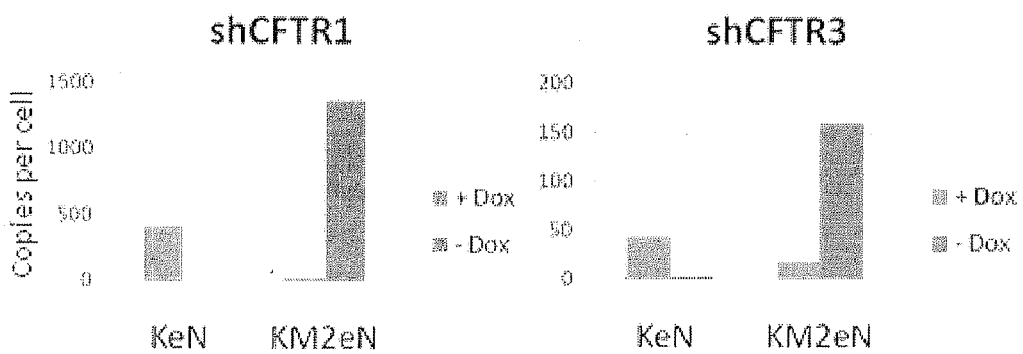

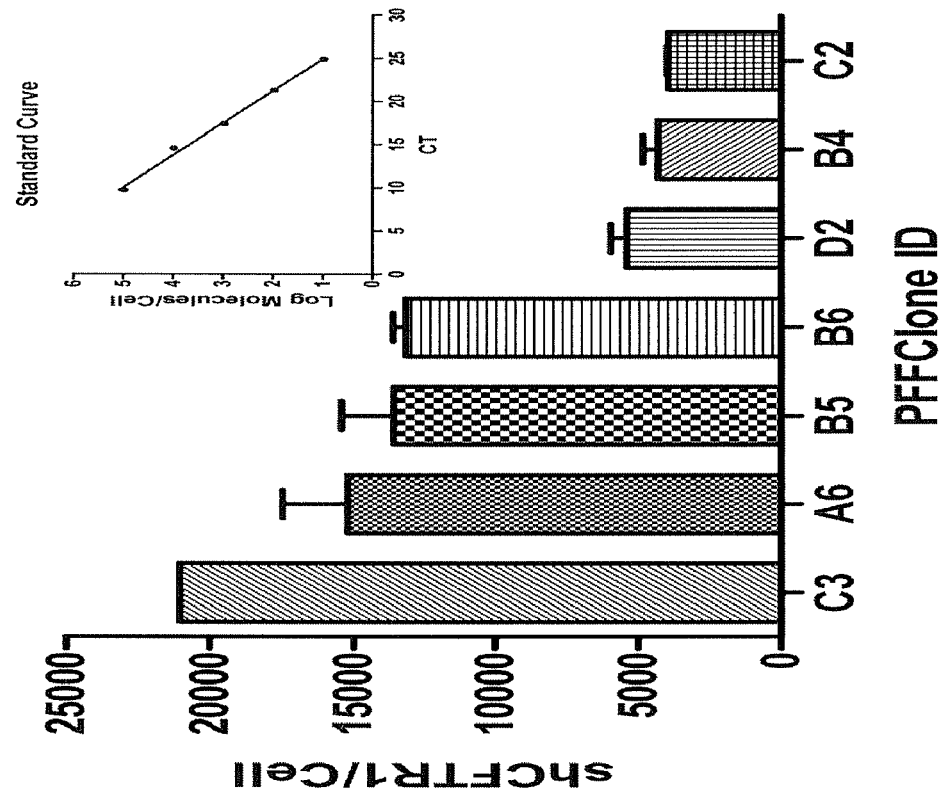
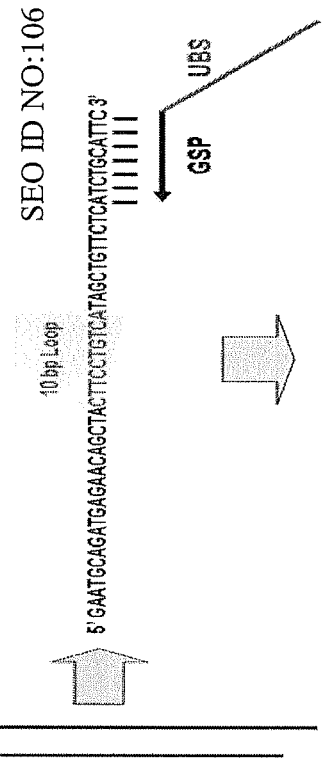
Figure 14

SEQUENCE LISTING

<160> NUMBER OF SEQ ID NOS: 107

<210> SEQ ID NO 1
<211> LENGTH: 26
<212> TYPE: DNA
<213> ORGANISM: Artificial Sequence
<220> FEATURE:
<223> OTHER INFORMATION: Synthetic DNA

<400> SEQUENCE: 1
ttattatttt tggaatagtt tagagg                                     26

<210> SEQ ID NO 2
<211> LENGTH: 26
<212> TYPE: DNA
<213> ORGANISM: Artificial Sequence
<220> FEATURE:
<223> OTHER INFORMATION: Synthetic DNA

<400> SEQUENCE: 2
aaaattccaa aaataatat cataac                                      26

<210> SEQ ID NO 3
<211> LENGTH: 26
<212> TYPE: DNA
<213> ORGANISM: Artificial Sequence
<220> FEATURE:
<223> OTHER INFORMATION: Synthetic DNA

<400> SEQUENCE: 3
ttgtggtttg tttaaattta ttaatg                                     26

<210> SEQ ID NO 4
<211> LENGTH: 25
<212> TYPE: DNA
<213> ORGANISM: Artificial Sequence
<220> FEATURE:
<223> OTHER INFORMATION: Synthetic DNA

<400> SEQUENCE: 4
ccaccaaaac aaaaatctaa acaac                                      25

<210> SEQ ID NO 5
<211> LENGTH: 20
<212> TYPE: DNA
<213> ORGANISM: Artificial Seqeunce
<220> FEATURE:
<223> OTHER INFORMATION: Synthetic DNA

<400> SEQUENCE: 5
cgccgcgttc gccgactacc                                            20

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA

<400> SEQUENCE: 6
cgcccccgct tcgacgctct c                                          21

<210> SEQ ID NO 7
<211> LENGTH: 20
<212> TYPE: DNA
<213> ORGANISM: Artificial Seqeunce
<220> FEATURE:
<223> OTHER INFORMATION: Synthetic DNA

<400> SEQUENCE: 7
gcttcctcct cagaccgctt                                               20

<210> SEQ ID NO 8
<211> LENGTH: 24
<212> TYPE: DNA
<213> ORGANISM: Artificial Sequence
<220> FEATURE:
<223> OTHER INFORMATION: PCR Primer

<400> SEQUENCE: 8
ggtcagcaaa gaacttatag cccc                                          24

<210> SEQ ID NO 9
<211> LENGTH: 33
<212> TYPE: DNA
<213> ORGANISM: Artificial Sequence
<220> FEATURE:
<223> OTHER INFORMATION: Synthetic DNA

<400> SEQUENCE: 9
gggcaagcag tcctaacaac catggaatgc aga                                33

<210> SEQ ID NO 10
<211> LENGTH: 24
<212> TYPE: DNA
<213> ORGANISM: Artificial Sequence
<220> FEATURE:
<223> OTHER INFORMATION: Synthetic DNA

<400> SEQUENCE: 10
gggcaagcag tcctaacaac catg                                          24

<210> SEQ ID NO 11
<211> LENGTH: 17
<212> TYPE: DNA
<213> ORGANISM: Artificial Seqeunce
<220> FEATURE:
<223> OTHER INFORMATION: Synthetic DNA

<400> SEQUENCE: 11
tagctgttct catctgc                                                  17

<210> SEQ ID NO 12
<211> LENGTH: 23
<212> TYPE: DNA
<213> ORGANISM: Artificial Seqeunce
<220> FEATURE:
<223> OTHER INFORMATION: Synthetic DNA

<400> SEQUENCE: 12
tctcggcatg gacgagctgt aca                                           23

<210> SEQ ID NO 13
<211> LENGTH: 35
<212> TYPE: DNA
<213> ORGANISM: Artificial Seqeunce
<220> FEATURE:
<223> OTHER INFORMATION: Primer

<400> SEQUENCE: 13
ctaaagtagc cccttgaatt ccgaggcagt aggca                              35

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
aagcttctgc cttctccctc c                                             21

<210> SEQ ID NO 15
<211> LENGTH: 20
<212> TYPE: DNA
<213> ORGANISM: Artificial Seqeunce
<220> FEATURE:
<223> OTHER INFORMATION: Synthetic DNA

<400> SEQUENCE: 15
aagtcaggtt gccagctgcc                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
cctcaagatt gtcagcaatg                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
atccacagtc ttctgagtgg                                               20

<210> SEQ ID NO 18
<211> LENGTH: 7
<212> TYPE: DNA
<213> ORGANISM: Artificial Sequence
<220> FEATURE:
<223> OTHER INFORMATION: Synthetic DNA/RNA
<220> FEATURE:
<221> NAME/KEY: misc_feature
<222> LOCATION: (2)..(2)
<223> OTHER INFORMATION: n is a or g or c or t/u
<220> FEATURE:
<221> NAME/KEY: misc_feature
<222> LOCATION: (3)..(3)
<223> OTHER INFORMATION: n is a or g or c or t/u

<400> SEQUENCE: 18 gnnaugg                                                              7

<210> SEQ ID NO 19
<211> LENGTH: 120
<212> TYPE: DNA
<213> ORGANISM: Artificial Sequence
<220> FEATURE:
<223> OTHER INFORMATION: Synthetic DNA

<400> SEQUENCE: 19
ataccggccg gaagttccta ttccgaagtt cctattctct agaaagtata ggaacttcat    60
aacttcgtat aatgtatgct atacgaagtt atctcgagaa ttcccgggag gcctactagt   120

<210> SEQ ID NO 20
<211> LENGTH: 118
<212> TYPE: DNA
<213> ORGANISM: Artificial Sequence
<220> FEATURE:
<223> OTHER INFORMATION: Synthetic DNA

<400> SEQUENCE: 20
gtattcatga gaagttccta tactttctag agaataggaa cttcggaata ggaacttcat    60
aacttcgtat agcatacatt atacgaagtt atccatggac tagtaggcct cccgggaa    118

<210> SEQ ID NO 21
<211> LENGTH: 29
<212> TYPE: DNA
<213> ORGANISM: Artificial Sequence
<220> FEATURE:
<223> OTHER INFORMATION: Synthetic DNA

<400> SEQUENCE: 21
caccatggga aaatcaaaag aaatcagcc                                      29

<210> SEQ ID NO 22
<211> LENGTH: 36
<212> TYPE: DNA
<213> ORGANISM: Artificial Sequence
<220> FEATURE:
<223> OTHER INFORMATION: Synthetic DNA

<400> SEQUENCE: 22
ggatcccaat ttaaaggcaa tgctaccaaa tactag                              36

<210> SEQ ID NO 23
<211> LENGTH: 9
<212> TYPE: DNA
<213> ORGANISM: Artificial Sequence
<220> FEATURE:
<223> OTHER INFORMATION: Synthetic DNA

<400> SEQUENCE: 23 agatctgat                                                             9

<210> SEQ ID NO 24
<211> LENGTH: 25
<212> TYPE: DNA
<213> ORGANISM: Artificial Sequence
<220> FEATURE:
<223> OTHER INFORMATION: Synthetic DNA

<400> SEQUENCE: 24
cattgatgag tttggacaaa ccaca                                          25

<210> SEQ ID NO 25
<211> LENGTH: 27
<212> TYPE: DNA
<213> ORGANISM: Artificial sequence
<220> FEATURE:
<223> OTHER INFORMATION: Synthetic DNA

<400> SEQUENCE: 25
accacatttg taggttttt acttgct                                         27

<210> SEQ ID NO 26
<211> LENGTH: 38
<212> TYPE: DNA
<213> ORGANISM: Artificial Sequence
<220> FEATURE:
<223> OTHER INFORMATION: Synthetic DNA

<400> SEQUENCE: 26
ctgagatctt aagctagcag gatccagaat tcattcag          38

<210> SEQ ID NO 27
<211> LENGTH: 26
<212> TYPE: DNA
<213> ORGANISM: Artificial Sequence
<220> FEATURE:
<223> OTHER INFORMATION: Synthetic DNA

<400> SEQUENCE: 27
ctgttccgct tcctcgctca ctgact          26

<210> SEQ ID NO 28
<211> LENGTH: 30
<212> TYPE: DNA
<213> ORGANISM: Artificial Sequence
<220> FEATURE:
<223> OTHER INFORMATION: Synthetic DNA

<400> SEQUENCE: 28
aaaaggatct aggtgaagat ccttttttgat          30

<210> SEQ ID NO 29
<211> LENGTH: 29
<212> TYPE: DNA
<213> ORGANISM: Artificial Sequence
<220> FEATURE:
<223> OTHER INFORMATION: Synthetic DNA

<400> SEQUENCE: 29
ctgcatcatg aacaataaaa ctgtctgct          29

<210> SEQ ID NO 30
<211> LENGTH: 27
<212> TYPE: DNA
<213> ORGANISM: Artificial Sequence
<220> FEATURE:
<223> OTHER INFORMATION: Synthetic DNA

<400> SEQUENCE: 30
tgccagtgtt acaaccaatt aaccaat          27

<210> SEQ ID NO 31
<211> LENGTH: 72
<212> TYPE: DNA
<213> ORGANISM: Artificial Sequence
<220> FEATURE:
<223> OTHER INFORMATION: Synthetic DNA

<400> SEQUENCE: 31
atatctcgag gccaccatgg ctcccaagaa gaagaggaag gtgatgagtc aatttgatat          60
attatgtaaa ac          72

<210> SEQ ID NO 32
<211> LENGTH: 33
<212> TYPE: DNA
<213> ORGANISM: Artificial Sequence
<220> FEATURE:
<223> OTHER INFORMATION: Synthetic DNA

<400> SEQUENCE: 32
atatagatct ttatatgcgt ctatttatgt agg          33

<210> SEQ ID NO 33
<211> LENGTH: 30
<212> TYPE: DNA
<213> ORGANISM: Artificial Sequence
<220> FEATURE:
<223> OTHER INFORMATION: Synthetic DNA

<400> SEQUENCE: 33
ccgaattcta ccatggtgag caagggcgag              30

<210> SEQ ID NO 34
<211> LENGTH: 31
<212> TYPE: DNA
<213> ORGANISM: Artificial Sequence
<220> FEATURE:
<223> OTHER INFORMATION: Synthetic DNA

<400> SEQUENCE: 34
ccagatcttt acttgtacag ctcgtccatg c            31

<210> SEQ ID NO 35
<211> LENGTH: 27
<212> TYPE: DNA
<213> ORGANISM: Artificial Sequence
<220> FEATURE:
<223> OTHER INFORMATION: Synthetic DNA

<400> SEQUENCE: 35
cactgaagtg ttgacttccc tgacagc                 27

<210> SEQ ID NO 36
<211> LENGTH: 33
<212> TYPE: DNA
<213> ORGANISM: Artificial Sequence
<220> FEATURE:
<223> OTHER INFORMATION: Synthetic DNA

<400> SEQUENCE: 36
ttcaattgtt agaagaactc gtcaagaagg cga          33

<210> SEQ ID NO 37
<211> LENGTH: 8
<212> TYPE: DNA
<213> ORGANISM: Artificial Sequence
<220> FEATURE:
<223> OTHER INFORMATION: Synthetic DNA

<400> SEQUENCE: 37 gttaactt                                      8

<210> SEQ ID NO 38
<211> LENGTH: 12
<212> TYPE: DNA
<213> ORGANISM: Artificial Sequence
<220> FEATURE:
<223> OTHER INFORMATION: Synthetic DNA

<400> SEQUENCE: 38
gttaagtcta ga                                 12

```
<210> SEQ ID NO 39
<211> LENGTH: 28
<212> TYPE: DNA
<213> ORGANISM: Artificial Sequence
<220> FEATURE:
<223> OTHER INFORMATION: Synthetic DNA

<400> SEQUENCE: 39
ctggatccag atctggtacc atttaaat                                           28

<210> SEQ ID NO 40
<211> LENGTH: 29
<212> TYPE: DNA
<213> ORGANISM: Artificial Sequence
<220> FEATURE:
<223> OTHER INFORMATION: Synthetic DNA

<400> SEQUENCE: 40
ttagatctgg cctcgcacac attccacat                                          29

<210> SEQ ID NO 41
<211> LENGTH: 25
<212> TYPE: DNA
<213> ORGANISM: Artificial Sequence
<220> FEATURE:
<223> OTHER INFORMATION: Synthetic DNA

<400> SEQUENCE: 41
tggttctttc cgcctcagaa gccat                                              25

<210> SEQ ID NO 42
<211> LENGTH: 23
<212> TYPE: DNA
<213> ORGANISM: Artificial Sequence
<220> FEATURE:
<223> OTHER INFORMATION: Synthetic DNA

<400> SEQUENCE: 42
tctccctata gtgagtcgta tta                                                23

<210> SEQ ID NO 43
<211> LENGTH: 23
<212> TYPE: DNA
<213> ORGANISM: Artificial Sequence
<220> FEATURE:
<223> OTHER INFORMATION: Synthetic DNA

<400> SEQUENCE: 43
tctcccttta gtgagggtta att                                                23

<210> SEQ ID NO 44
<211> LENGTH: 39
<212> TYPE: DNA
<213> ORGANISM: Artificial Sequence
<220> FEATURE:
<223> OTHER INFORMATION: Synthetic DNA

<400> SEQUENCE: 44
tggatcccaa tccttaaccc tagaaagata atcatattg                               39

<210> SEQ ID NO 45
<211> LENGTH: 32
<212> TYPE: DNA
<213> ORGANISM: Artificial Sequence
<220> FEATURE:
<223> OTHER INFORMATION: Synthetic DNA
```

<400> SEQUENCE: 45
gtggccataa aagttttgtt actttataga ag                          32

<210> SEQ ID NO 46
<211> LENGTH: 32
<212> TYPE: DNA
<213> ORGANISM: Artificial Sequence
<220> FEATURE:
<223> OTHER INFORMATION: Synthetic DNA

<400> SEQUENCE: 46
ttggccataa gttatcacgt aagtagaaca tg                          32

<210> SEQ ID NO 47
<211> LENGTH: 33
<212> TYPE: DNA
<213> ORGANISM: Artificial Sequence
<220> FEATURE:
<223> OTHER INFORMATION: Synthetic DNA

<400> SEQUENCE: 47
tggtacctag attaaccta gaaagatagt ctg                          33

<210> SEQ ID NO 48
<211> LENGTH: 52
<212> TYPE: DNA
<213> ORGANISM: Artificial Sequence
<220> FEATURE:
<223> OTHER INFORMATION: Synthetic DNA

<400> SEQUENCE: 48
tctcccttta gtgagggtta attgatatct aatacgactc actataggga ga    52

<210> SEQ ID NO 49
<211> LENGTH: 32
<212> TYPE: DNA
<213> ORGANISM: Artificial Sequence
<220> FEATURE:
<223> OTHER INFORMATION: Synthetic DNA

<400> SEQUENCE: 49
aaggatccga ttacagtgcc ttgcataagt at                          32

<210> SEQ ID NO 50
<211> LENGTH: 34
<212> TYPE: DNA
<213> ORGANISM: Artificial Sequence
<220> FEATURE:
<223> OTHER INFORMATION: Synthetic DNA

<400> SEQUENCE: 50
aaggtaccga ttacagtgcc ttgcataagt attc                        34

<210> SEQ ID NO 51
<211> LENGTH: 26
<212> TYPE: DNA
<213> ORGANISM: Artificial Sequence
<220> FEATURE:
<223> OTHER INFORMATION: Synthetic DNA

<400> SEQUENCE: 51
ccatctttgt tagggtttc acagta                                  26

```
<210> SEQ ID NO 52
<211> LENGTH: 25
<212> TYPE: DNA
<213> ORGANISM: artificial seqeunce
<220> FEATURE:
<223> OTHER INFORMATION: Synthetic DNA

<400> SEQUENCE: 52
ccaggttcta ccaagtattg acaca                                          25

<210> SEQ ID NO 53
<211> LENGTH: 30
<212> TYPE: DNA
<213> ORGANISM: Artificial Sequence
<220> FEATURE:
<223> OTHER INFORMATION: Synthetic DNA

<400> SEQUENCE: 53
aaagctagca tgaagaccaa ggagctcacc                                     30

<210> SEQ ID NO 54
<211> LENGTH: 26
<212> TYPE: DNA
<213> ORGANISM: Artificial Sequence
<220> FEATURE:
<223> OTHER INFORMATION: Synthetic DNA

<400> SEQUENCE: 54
aaggatcctc aatacttggt agaacc                                         26

<210> SEQ ID NO 55
<211> LENGTH: 30
<212> TYPE: DNA
<213> ORGANISM: Artificial Sequence
<220> FEATURE:
<223> OTHER INFORMATION: Synthetic DNA

<400> SEQUENCE: 55
ttagatctac catgaccgag tacaagccca                                     30

<210> SEQ ID NO 56
<211> LENGTH: 46
<212> TYPE: DNA
<213> ORGANISM: Artificial Sequence
<220> FEATURE:
<223> OTHER INFORMATION: Synthetic DNA

<400> SEQUENCE: 56
ataacttcgt ataatgtatg ctatacgaag ttatctcgag tggcca                   46

<210> SEQ ID NO 57
<211> LENGTH: 46
<212> TYPE: DNA
<213> ORGANISM: Artificial Sequence
<220> FEATURE:
<223> OTHER INFORMATION: Synthetic DNA

<400> SEQUENCE: 57
ataacttcgt atagcataca ttatacgaag ttattggcca ctcgag                   46

<210> SEQ ID NO 58
<211> LENGTH: 45
<212> TYPE: DNA
<213> ORGANISM: Artificial Sequence
<220> FEATURE:
<223> OTHER INFORMATION: Synthetic DNA
```

```
<400> SEQUENCE: 58
cctccactac gactcactga agggcaagca gtcctaacaa ccatg          45

<210> SEQ ID NO 59
<211> LENGTH: 18
<212> TYPE: DNA
<213> ORGANISM: Artificial Sequence
<220> FEATURE:
<223> OTHER INFORMATION: Synthetic DNA

<400> SEQUENCE: 59
gttgttagga ctgcttgc                                        18

<210> SEQ ID NO 60
<211> LENGTH: 26
<212> TYPE: DNA
<213> ORGANISM: Artificial Sequence
<220> FEATURE:
<223> OTHER INFORMATION: Synthetic DNA

<400> SEQUENCE: 60
ctagcatggt tgttaggact gcttgc                               26

<210> SEQ ID NO 61
<211> LENGTH: 25
<212> TYPE: DNA
<213> ORGANISM: Artificial Sequence
<220> FEATURE:
<223> OTHER INFORMATION: Synthetic DNA

<400> SEQUENCE: 61
cctccactac gactcactga agggc                                25

<210> SEQ ID NO 62
<211> LENGTH: 31
<212> TYPE: DNA
<213> ORGANISM: Artificial Sequence
<220> FEATURE:
<223> OTHER INFORMATION: Synthetic DNA

<400> SEQUENCE: 62
attttccaag ctgtttaaag gcacagtcaa c                         31

<210> SEQ ID NO 63
<211> LENGTH: 25
<212> TYPE: DNA
<213> ORGANISM: Artificial Sequence
<220> FEATURE:
<223> OTHER INFORMATION: Synthetic DNA

<400> SEQUENCE: 63
aattaaactg ggcatcagcg caatt                                25

<210> SEQ ID NO 64
<211> LENGTH: 26
<212> TYPE: DNA
<213> ORGANISM: Artificial Sequence
<220> FEATURE:
<223> OTHER INFORMATION: Synthetic DNA

<400> SEQUENCE: 64
acagaccgat aaaacacatg cgtcaa                               26
```

```
<210> SEQ ID NO 65
<211> LENGTH: 28
<212> TYPE: DNA
<213> ORGANISM: Artificial Sequence
<220> FEATURE:
<223> OTHER INFORMATION: Synthetic DNA

<400> SEQUENCE: 65
gggtgaatac ttatgcaccc aacagatg                                        28

<210> SEQ ID NO 66
<211> LENGTH: 30
<212> TYPE: DNA
<213> ORGANISM: Artificial Sequence
<220> FEATURE:
<223> OTHER INFORMATION: Synthetic DNA

<400> SEQUENCE: 66
gacttgtgtc atgcacaaag tagatgtcct                                      30

<210> SEQ ID NO 67
<211> LENGTH: 27
<212> TYPE: DNA
<213> ORGANISM: Artificial Sequence
<220> FEATURE:
<223> OTHER INFORMATION: Synthetic DNA

<400> SEQUENCE: 67
gcgcaattca attggtttgg taatagc                                         27

<210> SEQ ID NO 68
<211> LENGTH: 24
<212> TYPE: DNA
<213> ORGANISM: Artificial Sequence
<220> FEATURE:
<223> OTHER INFORMATION: Synthetic DNA

<400> SEQUENCE: 68
tcctaaatgc acagcgacgg attc                                            24

<210> SEQ ID NO 69
<211> LENGTH: 28
<212> TYPE: DNA
<213> ORGANISM: Artificial Sequence
<220> FEATURE:
<223> OTHER INFORMATION: Synthetic DNA

<400> SEQUENCE: 69
cagtacataa tgggaaaaag tccaaggg                                        28

<210> SEQ ID NO 70
<211> LENGTH: 20
<212> TYPE: DNA
<213> ORGANISM: Artificial Sequence
<220> FEATURE:
<223> OTHER INFORMATION: Synthetic DNA

<400> SEQUENCE: 70
cagctggatc cagatcccta                                                 20

<210> SEQ ID NO 71
<211> LENGTH: 11
<212> TYPE: DNA
<213> ORGANISM: Artificial Sequence
<220> FEATURE:
<223> OTHER INFORMATION: Synthetic DNA
```

<400> SEQUENCE: 71
cagttgaagt c                                                           11

<210> SEQ ID NO 72
<211> LENGTH: 20
<212> TYPE: DNA
<213> ORGANISM: Artificial Sequence
<220> FEATURE:
<223> OTHER INFORMATION: Synthetic DNA

<400> SEQUENCE: 72
ctacctcaag ataacatagc                                                  20

<210> SEQ ID NO 73
<211> LENGTH: 11
<212> TYPE: DNA
<213> ORGANISM: Artificial Sequence
<220> FEATURE:
<223> OTHER INFORMATION: Synthetic DNA

<400> SEQUENCE: 73
cagttgaagt a                                                           11

<210> SEQ ID NO 74
<211> LENGTH: 20
<212> TYPE: DNA
<213> ORGANISM: Artificial Sequence
<220> FEATURE:
<223> OTHER INFORMATION: Synthetic DNA

<400> SEQUENCE: 74
tgaaaaataa ttggaacaaa                                                  20

<210> SEQ ID NO 75
<211> LENGTH: 20
<212> TYPE: DNA
<213> ORGANISM: Artificial Sequence
<220> FEATURE:
<223> OTHER INFORMATION: Synthetic DNA

<400> SEQUENCE: 75
ttcggaagat gtggtatata                                                  20

<210> SEQ ID NO 76
<211> LENGTH: 20
<212> TYPE: DNA
<213> ORGANISM: Artificial Sequence
<220> FEATURE:
<223> OTHER INFORMATION: Synthetic DNA

<400> SEQUENCE: 76
tttatctatc aaaacacatc                                                  20

<210> SEQ ID NO 77
<211> LENGTH: 11
<212> TYPE: DNA
<213> ORGANISM: Artificial Sequence
<220> FEATURE:
<223> OTHER INFORMATION: Synthetic DNA

<400> SEQUENCE: 77
gacttcaact g                                                           11

```
<210> SEQ ID NO 78
<211> LENGTH: 20
<212> TYPE: DNA
<213> ORGANISM: Artificial Sequence
<220> FEATURE:
<223> OTHER INFORMATION: Synthetic DNA

<400> SEQUENCE: 78
tagggatctg gtaccattta                                               20

<210> SEQ ID NO 79
<211> LENGTH: 20
<212> TYPE: DNA
<213> ORGANISM: Artificial Sequence
<220> FEATURE:
<223> OTHER INFORMATION: Synthetic DNA

<400> SEQUENCE: 79
tatacacaat ggaatactac                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic DNA

<400> SEQUENCE: 80
tataaaaaaa tgtctgctcc                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic DNA

<400> SEQUENCE: 81
tagagacaga cctggaaagg                                               20

<210> SEQ ID NO 82
<211> LENGTH: 30
<212> TYPE: DNA
<213> ORGANISM: Artificial Sequence
<220> FEATURE:
<223> OTHER INFORMATION: Synthetic DNA

<400> SEQUENCE: 82
gctggatcca gatccctata cagttgaagt                                    30

<210> SEQ ID NO 83
<211> LENGTH: 30
<212> TYPE: DNA
<213> ORGANISM: Artificial Sequence
<220> FEATURE:
<223> OTHER INFORMATION: Synthetic DNA

<400> SEQUENCE: 83
attgatatat aattcacata cagttgaagt                                    30

<210> SEQ ID NO 84
<211> LENGTH: 30
<212> TYPE: DNA
<213> ORGANISM: Artificial Sequence
<220> FEATURE:
<223> OTHER INFORMATION: Synthetic DNA
```

<400> SEQUENCE: 84
tcaatcatca cactatggta cagttgaagt                                30

<210> SEQ ID NO 85
<211> LENGTH: 30
<212> TYPE: DNA
<213> ORGANISM: Artificial Sequence
<220> FEATURE:
<223> OTHER INFORMATION: Synthetic DNA

<400> SEQUENCE: 85
atattacaca agatatatta cagttgaagt                                30

<210> SEQ ID NO 86
<211> LENGTH: 30
<212> TYPE: DNA
<213> ORGANISM: Artificial Sequence
<220> FEATURE:
<223> OTHER INFORMATION: Synthetic DNA

<400> SEQUENCE: 86
gtaatgttcc attgtgtata cagttggagt                                30

<210> SEQ ID NO 87
<211> LENGTH: 30
<212> TYPE: DNA
<213> ORGANISM: Artificial Sequence
<220> FEATURE:
<223> OTHER INFORMATION: Synthetic DNA

<400> SEQUENCE: 87
acaaacaaga accactacta cagttgaagt                                30

<210> SEQ ID NO 88
<211> LENGTH: 30
<212> TYPE: DNA
<213> ORGANISM: Artificial Sequence
<220> FEATURE:
<223> OTHER INFORMATION: Synthetic DNA

<400> SEQUENCE: 88
caaggcactg taatcggtac catttaaatc                                30

<210> SEQ ID NO 89
<211> LENGTH: 30
<212> TYPE: DNA
<213> ORGANISM: Artificial Sequence
<220> FEATURE:
<223> OTHER INFORMATION: Synthetic DNA

<400> SEQUENCE: 89
caaggcactg tacttgggca agatgcttaa                                30

<210> SEQ ID NO 90
<211> LENGTH: 30
<212> TYPE: DNA
<213> ORGANISM: Artificial Sequence
<220> FEATURE:
<223> OTHER INFORMATION: Synthetic DNA

<400> SEQUENCE: 90
caaggcactg tatatcctaa tgcctagaga                                30

<210> SEQ ID NO 91
<211> LENGTH: 30
<212> TYPE: DNA
<213> ORGANISM: Artificial Sequence
<220> FEATURE:
<223> OTHER INFORMATION: Synthetic DNA

<400> SEQUENCE: 91
caaggcactg taatcggtac ccatggttgt         30

<210> SEQ ID NO 92
<211> LENGTH: 30
<212> TYPE: DNA
<213> ORGANISM: Artificial Sequence
<220> FEATURE:
<223> OTHER INFORMATION: Synthetic DNA

<400> SEQUENCE: 92
caaggcactg tatattcaag aaatcaaaaa         30

<210> SEQ ID NO 93
<211> LENGTH: 30
<212> TYPE: DNA
<213> ORGANISM: Artificial Sequence
<220> FEATURE:
<223> OTHER INFORMATION: Synthetic DNA

<400> SEQUENCE: 93
caaggcactg tatacggtac catttgcttg         30

<210> SEQ ID NO 94
<211> LENGTH: 30
<212> TYPE: DNA
<213> ORGANISM: Artificial Sequence
<220> FEATURE:
<223> OTHER INFORMATION: Synthetic DNA

<400> SEQUENCE: 94
actatagggc gaattgggcc cagaggtgta         30

<210> SEQ ID NO 95
<211> LENGTH: 30
<212> TYPE: DNA
<213> ORGANISM: Artificial Sequence
<220> FEATURE:
<223> OTHER INFORMATION: Synthetic DNA

<400> SEQUENCE: 95
gagattaagg tgctagtagg cagaggtgta         30

<210> SEQ ID NO 96
<211> LENGTH: 30
<212> TYPE: DNA
<213> ORGANISM: Artificial Sequence
<220> FEATURE:
<223> OTHER INFORMATION: Synthetic DNA

<400> SEQUENCE: 96
atgctcaagc ccccagcccc cagaggtgta         30

<210> SEQ ID NO 97
<211> LENGTH: 30
<212> TYPE: DNA
<213> ORGANISM: Artificial Sequence
<220> FEATURE:
<223> OTHER INFORMATION: Synthetic DNA

<400> SEQUENCE: 97
gactttagct acctgcccag cagaggtgta                                30

<210> SEQ ID NO 98
<211> LENGTH: 30
<212> TYPE: DNA
<213> ORGANISM: Artificial Sequence
<220> FEATURE:
<223> OTHER INFORMATION: Synthetic DNA

<400> SEQUENCE: 98
acaaccaagc ctccaaggtc cagaggtgta                                30

<210> SEQ ID NO 99
<211> LENGTH: 30
<212> TYPE: DNA
<213> ORGANISM: Artificial Sequence
<220> FEATURE:
<223> OTHER INFORMATION: Synthetic DNA

<400> SEQUENCE: 99
tcaagtcaag gagtctcaac cagaggtgta                                30

<210> SEQ ID NO 100
<211> LENGTH: 30
<212> TYPE: DNA
<213> ORGANISM: Artificial Sequence
<220> FEATURE:
<223> OTHER INFORMATION: Synthetic DNA

<400> SEQUENCE: 100
ctttctaggg ttaatctagg taccatttaa                                30

<210> SEQ ID NO 101
<211> LENGTH: 30
<212> TYPE: DNA
<213> ORGANISM: Artificial Sequence
<220> FEATURE:
<223> OTHER INFORMATION: Synthetic DNA

<400> SEQUENCE: 101
ctttctaggg ttaagcacaa acactgctgc                                30

<210> SEQ ID NO 102
<211> LENGTH: 30
<212> TYPE: DNA
<213> ORGANISM: Artificial Sequence
<220> FEATURE:
<223> OTHER INFORMATION: Synthetic DNA

<400> SEQUENCE: 102
ctttctaggg ttaagagccc cctgctcatc                                30

<210> SEQ ID NO 103
<211> LENGTH: 30
<212> TYPE: DNA
<213> ORGANISM: Artificial Sequence
<220> FEATURE:
<223> OTHER INFORMATION: Synthetic DNA

<400> SEQUENCE: 103
ctttctaggg ttaacttgat cagagatata                                30

```
<210> SEQ ID NO 104
<211> LENGTH: 30
<212> TYPE: DNA
<213> ORGANISM: Artificial Sequence
<220> FEATURE:
<223> OTHER INFORMATION: Synthetic DNA

<400> SEQUENCE: 104
ctttctaggg ttaatagtta gcaacagcct                                        30

<210> SEQ ID NO 105
<211> LENGTH: 30
<212> TYPE: DNA
<213> ORGANISM: Artificial Sequence
<220> FEATURE:
<223> OTHER INFORMATION: Synthetic DNA

<400> SEQUENCE: 105
ctttctaggg ttaaactcta gcatggttgt                                        30

<210> SEQ ID NO 106
<211> LENGTH: 52
<212> TYPE: DNA
<213> ORGANISM: Artificial Seqeunce
<220> FEATURE:
<223> OTHER INFORMATION: Synthetic DNA

<400> SEQUENCE: 106
gaatgcagat gagaacagct acttcctgtc atagctgttc tcatctgcat tc              52

<210> SEQ ID NO 107
<211> LENGTH: 45
<212> TYPE: DNA
<213> ORGANISM: Artificial Sequence
<220> FEATURE:
<223> OTHER INFORMATION: Synthetic DNA

<400> SEQUENCE: 107
atcgacaaga gtagacgtaa ggtaccaaca atcctgacga acggg                      45
```

METHOD FOR PRODUCING A TRANSGENIC PIG USING A HYPER-METHYLATED TRANSPOSON

CROSS-REFERENCE TO RELATED APPLICATIONS

This patent application claims priority to U.S. Provisional Ser. No. 61/081,293 filed Jul. 16, 2008, which is hereby incorporated by reference herein.

STATEMENT OF GOVERNMENT INTEREST

This invention was made with government support from the National Institutes of Health through the NIDDK. The United States government may have certain rights in the invention.

TECHNICAL FIELD

The technical field relates to methods for producing transgenic animals, and more particularly to producing transgenic animals using one or more transposons.

BACKGROUND

Transposons have a primary scientific use as gene discovery tools, for instance the creation of mutants to discover gene functions. The use of transposons is also being studied as delivery tool for gene therapy.

SUMMARY

Tools and techniques for using transposons for the creation of transgenic livestock have been discovered and are described herein. Further, tools and techniques for using small interfering ribonucleic acids (siRNAs) have been discovered and are taught herein. Moreover, techniques for making transgenic livestock by an efficient generation of founders and selection of animals with desired traits are described. Swine are an important agricultural commodity and biomedical model. These improved methods include germline transgenesis tools that provide new opportunities to improve production efficiency, enhance disease resistance, and add value to swine products. This document is based on the discovery of methods and materials for producing transgenic animals, and in particular transgenic artiodactyls (e.g., pigs, cows, sheep, and goats) and provides improved transgenesis rates. As described herein, transposons and recombinases are capable of mobilizing deoxyribonucleic acids (DNA) into and out of the porcine genome in a precise and efficient manner, providing the basis for developing transposon and recombinase based tools for genetic engineering of the swine genome.

Methylation of DNA is conventionally common DNA modification typically associated with quiescent (non-expressed) DNA. Unexpectedly, however, methylation can be used to enhance Sleeping Beauty transposition (Yusa, et al., *Molecular and Cellular Biology* (2004) 24 (9): 4004-4018) In some embodiments, cytosine-phosphodiester-guanine (CpG) hypermethylated transposon transgenes and pronuclear injection can be used to achieve enhanced germline transgenesis rates in artiodactyls with efficiencies ranging from 50-90%. Without being bound to a particular mechanism, artificially introduced methylation patterns are subsequently reprogrammed in the early embryo, reliably leading to founders which express the desired transgene. The term hypermethylation refers to a nucleic acid that has been treated to increase its methylation. A fully hypermethylated nucleic acid has a sequence wherein all of its CpG sites are methylated. A substantially fully hypermethylated nucleic acid has at least 90% of its CpG sites methylated following a methylation treatment. Embodiments include hypermethylated, fully hypermethylated, and substantially fully hypermethylated nucleic acids, e.g., transposons, or a sequence located between a pair of inverted terminal repeats of a transposon.

Transposons can also be used to make transgenic livestock. A transgenic pig was made by way of example, with the introduction of porcine cystic fibrosis transmembrane conductance regulator (CFTR) RNA interference cassetteas a particular example. In one aspect, this document features a transgenic pig, the nucleated cells of which include a nucleic acid construct. The nucleic acid construct contains a transcriptional unit that includes a regulatory region operably linked to a nucleic acid sequence encoding a siRNA (e.g., small hairpin RNA) that reduces expression of CFTR, wherein an inverted repeat of a transposon flanks each side of the transcriptional unit. The regulatory region can be a constitutive promoter or an inducible promoter. The inducible promoter can be regulated by, e.g., tetracycline or doxycycline. The transposon can be, e.g., selected from the group consisting of Sleeping Beauty, Tol2, PiggyBac, Frog Prince, Minos, and Hsmar1. The nucleic acid construct further can include an insulator element flanking each side of the transcriptional unit. The nucleic acid construct can be CpG-methylated.

In another aspect, the document features a method for making a transgenic pig. The method includes introducing a transgenic pig cell into an enucleated pig oocyte to establish a combined cell, wherein the transgenic pig cell includes a nucleic acid construct and a source of a transposase, the nucleic acid construct including a transcriptional unit, the transcriptional unit including a regulatory region operably linked to a nucleic acid sequence encoding a siRNA (e.g., small hairpin RNA) that reduces expression of porcine CFTR, wherein an inverted repeat of a transposon flanks each side of the transcriptional unit; producing a porcine embryo from the combined cell; transferring the porcine embryo to a recipient female; and allowing the porcine embryo to develop in the recipient female to produce the transgenic pig, the nucleated cells of which include the nucleic acid construct. The source of the transposase can be the nucleic acid construct encoding the siRNA or a different nucleic acid construct. The transposon can be selected from the group consisting of Sleeping Beauty, Tol2, PiggyBac, Frog Prince, Minos, and Hsmar1. The nucleic acid construct further can include an insulator element flanking each side of the transcriptional unit. The regulatory region can be a constitutive promoter or an inducible promoter (e.g., regulated by tetracycline or doxycycline). The target nucleic sequence can encode a small hairpin RNA that reduces expression of porcine CFTR. In some embodiments, expression of such a small hairpin RNA is regulated by an inducible promoter.

This document also features a method for making a transgenic pig that includes injecting a nucleic acid construct and a source of a transposase into a pronuclear staged in vitro fertilized egg. The nucleic acid construct includes a transcriptional unit, the transcriptional unit including a regulatory region operably linked to a target nucleic acid sequence, wherein an inverted repeat of a transposon flanks each side of the transcriptional unit; transferring the injected fertilized egg to a recipient female; and allowing the injected fertilized egg to develop in the recipient porcine female to produce the transgenic pig. The source of the transposase can be the nucleic acid construct that includes the target nucleic acid or a different nucleic acid construct. The transposon can be selected from the group consisting of Sleeping Beauty, Tol2, PiggyBac, Frog Prince, Minos, and Hsmar1. The nucleic acid construct further can include an insulator element flanking each side of the transcriptional unit. The regulatory region can be a constitutive promoter, a tissue-specific promoter (e.g., that preferentially expresses in heart tissue or beta-cells), or inducible (e.g., regulated by tetracycline or doxycycline). The target nucleic acid sequence can encode, for example, a polypeptide such as a recombinase or a fluorescent polypeptide or a siRNA such as a small hairpin RNA (e.g., a small hairpin RNA reduces expression of porcine CFTR).

In yet another aspect, this document features a method for making a transgenic pig. The method includes injecting at least two nucleic acid constructs and a source of a transposase into an animal, e.g., a pronuclear staged in vitro fertilized egg, wherein each nucleic acid construct includes a transcriptional unit and an inverted repeat of a transposon flanking each side of the transcriptional unit, wherein the transcriptional unit of one of the nucleic acid constructs includes a regulatory region operably linked to a first target nucleic acid sequence, and wherein the transcriptional unit of one of the nucleic acid constructs includes a regulatory region operably linked to a nucleic acid sequence encoding a second target nucleic acid (e.g., a selectable marker or another gene of interest). The injected fertilized egg may be transferred to a recipient female; and the injected fertilized egg allowed to develop in the recipient porcine female to produce the transgenic pig. The nucleic acid construct encoding the second target nucleic acid can be provided in excess of the nucleic acid construct that includes the target nucleic acid sequence.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are hereby incorporated by reference herein in their entirety. In case of conflict, the present specification, including definitions, will control. In addition, the materials, methods, and examples are illustrative only and not intended to be limiting. The details of one or more embodiments of the invention are set forth in the accompanying drawings and the description below.

DESCRIPTION OF DRAWINGS

FIG. 1 depicts efficient transposition of chemically modified transposons after pronuclear injection. a) The T2/sh_m-CFTR1 transposon expresses puromycin N-acetyltransferase (Puro) from the SV40 viral promoter and enhancer (E). A hairpin designed to silence the mouse Cftr gene product is expressed from the human H1 promoter. The KT2/HSA-CCTG$_{300}$ transposon contains the human skeletal actin gene with 300 copies of a CCTG tetranucleotide repeat in its 3'UTR, flanked by loxP sites (black chevrons). The KT2/KD$^{Rab38}$ transposon expresses a blasticidin-green fluorescent fusion protein (Bsd:GFP) and a silencer hairpin targeting rat Rab38, flanked by human microRNA 30 gene sequences, from a CpG-less promoter (from pCpG-mcs, Invivogen, San Diego, Calif.). The KT2H-CD40Ig transposon drives expression of CD40Ig from the human insulin promoter (HIP). (b) Southern blots on founder animals obtained after pronuclear injection with CpG-hypermethylated or nonmethylated transposon substrate and SB transposase mRNA reveal a significant increase in both the number of transgenic animals and the number of independent transgene integration events. BamHI (B (a)) digestion of genomic DNA resulted in a predictable 2310-bp fragment (black arrowhead) from random, nonhomologous integrants while transposase-mediated events are evident as slower-migrating fragments. A nonspecific hybridization near 4.8-kb is evident in all lanes. (c) Germline mosaicism is evident in the outcross generation from select founders. In several cases, insertions present in tail-biopsy DNA from founders (first lane in each group) are not found in their offspring.

FIGS. 3A and 3B depict Sleeping Beauty function in pig cells. A) Diagrams of the DNA vectors transfected into pig cells. pT2-FloxP-PTK is the experimental SB transposon. The transposon is flanked by inverted terminal repeats (ITR). The puromycin phosphotransferase-thymidine kinase fusion protein (PTK) is flanked by recombinase recognition sites, FRT and loxP, for Flp and Cre, respectively. pKUb-SB11 is the source of transposase and is expressed from the ubiquitin promoter (Ub). pKUb-SBΔDDE is a nonfunctional version of transposase because of an internal deletion within the catalytic domain. pCMV-β functions as negative control. B) The colony forming ability of pT2-FloxP-PTK in pig fetal fibroblast (PFF) and porcine endometrial gland epithelium (PEGE) was determined by counting puromycin resistant colonies after plating 60,000 cells on 10 cm dishes when pT2-FloxPPTK was co-transfected with pKUb-SB11 (+SB), pKUb-SBΔDDE (+SBΔDDE), or pCMV-β (+βgal). The addition of functional transposase (+SB) versus a non-functional transposase (SBΔDDE) or pCMV-β (Bgal) was determined to be significant by analysis with an unpaired t-test (p-values<0.000002).

FIG. 4A-4E depict the activity of multiple transposon systems in PEGE cells. A) A drawing of a generic transposon (pTP-PTK) used for colony formation assays. The transposons used, except the transposon-specific inverted terminal repeats, are identical. The vector backbones of the transposons are also identical except for pGTol2P-PTK. The pKx-Ts drawing is a generic representation of the transposase-expressing vector. The promoter choices include Ub, CMV, and mCAGs for SB, Tol2, and PB and PP, respectively. The vector backbones and poly(A) signals are identical except for pCMV-Tol2 B-E) The number of colonies formed with SB, PP, Tol2, or PB PTK transposons are shown with βgal instead of transposase (−Ts) and with transposase (+Ts), where Ts is SB, PP, Tol2, or PB. In each case, the significance of transposase was verified with an unpaired t-test (p-values≦0.00002).

FIG. 5 contains examples of transposon insertion junctions. Transposon junctions amplified from PEGE cells are shown in groups of five with expected non-transposed vector sequence (lowercase) highlighted above. From top to bottom, SB (ITR-L), PP (ITR-R), Tol2 (ITR-L), and PB (ITR-R), and. Target site duplications (bold) for each transposon are separated from genomic DNA and corresponding (ITR) by a space. FIG. 5 sets for the SEQ ID NOs: 82-105.

FIG. 8A-8C depict a CRE-Activated Transgene. A) An illustration of the Cre-activated transgene vector. The full vector, pTC-loxPTK-G, produces PTK from the mini-CAGs promoter. Transcriptional leakage into the downstream gene, GFP, is limited due to the incorporation of three full polyadenylation signals, a so-called triple-stop. Recombination by Cre eliminates PTK and triplestop, activating GFP expression from pTC-lox-G. B) pTC-loxPTK-G was transfected into PEGE cells with (+Cre) or without (−Cre) pPGK-nlsCre. Cells were monitored for GFP expression by fluorescent microscopy (image inserts) and flow cytometry. The percentage of cells expressing GFP was dependent on co-transfection with pPGK-nlsCre. C) PEGE cells were transfected with pTC-loxPTK-G along with pPGK-nlsCre (+Cre), pCMV-β (+βgal), pKUb-SB11 (+SB), or pKUb-SB11 and pPGK-nlsCre (+SB+Cre). The cells were plated in puromycin selective media and colonies were counted.

FIG. 9 depicts conditional gene-activation of integrated transposons. Colonies from the transfection of pTC-loxPTK-G with pKUb-SB11 (FIG. 5C) were expanded in selective media containing puromycin. DNA from these transgenic colonies was isolated and analyzed by Southern hybridization. A) A schematic of pKT2C-loxPTK-G that shows the AseI restriction sites and the location of the PTK hybridization probe (diagonal lined rectangle) used for Southern analysis. B) A Southern blot of pKT2C-loxPTK-G colonies. The clones were analyzed without Cre excision, so integrants that result from transposition should be equal to or greater than the transposon size of 4.9 kb (open arrow). Whereas, bands associated with concatemer formation are found at 6.0 kb (vertical line arrow). The positions of the DNA marker bands of the 1 kb QUANTI-MARKER from ISC Bioexpress (Kaysville, Utah), are indicated by black dots on the right of each blot with sizes of 12, 10, 8, 6, 5, 4, 3, 2.5, and 2 kb shown. C) pKT2C-loxPTK-G colonies were transfected with pPGK-nlsCre and plated under gancyclovir selection. Clones with PTK eliminated by recombination became gancyclovir resistant and were counted. Cre-activation of all clones was determined to be significant (p<0.5).

FIGS. 12A-12B depict APOBEC-G expression plasmids and transfection scheme. FIG. 12A contains a map of pKT2X-LP2-PTK-APOBEC-G, where "X" represents the miniCags, Ubiquitin or PGK promoters. This transposon was transfected at a 2:1 ratio with pKC-SB100X as shown and cells were selected in medium containing puromycin. Upon the addition of Cre recombinase via transfection or crossing with to a Cre transgenic animal, the PTK stop cassette is removed thereby juxtaposing the APOBEC-G cDNA to the promoter and activating expression. B) Two transposons, pKT2P-APOBEC-G and pKT2P-PTK, were simultaneously transfected into cells at a 5:1 ratio in trans with pKC-SB100X for a total of 2 parts transposon to 1 part transposase. Cells were selected in medium containing puromycin and assayed for co-retention of both PTK by selection and APOBEC-G transposons by PCR.

FIGS. 13A-13C depict tet regulated expression of shCFTR. In FIGS. 13A and 13B, vector design and predicted response to doxycycline is illustrated. Each vector contains a neomycin resistance gene (Neo) downstream of the ECMV internal ribosome entry site (IRES) allowing for selection in medium containing G-418 when the cassette is in the active state. C) Neomycin resistant pig fetal fibroblasts (PFFs) were cultured in the presence or absence of doxycycline (Dox) for a period of 15 days. Small fraction RNA was isolated followed by qRT-PCR for either shCFTR1 or shCFTR3. Copies per cell were determined by comparison to a standard curve for either shCFTR1 or shCFTR3 calibrated to the assumption that each cell contains 10 pg of total RNA of which 20% is small fraction RNA.

FIG. 14A is a schematic of the quantification of shCFTR1 in PFFs. A gene specific primer (GSP) is designed against the shRNA of interest with 9 base pairs hybridization domain at the 3' end. A universal binding sequence (UBS) is included at the 5' end of the GSP for hybridization of a universal primer (UP). The GSP is used to reverse transcribe target shRNAs resulting in an extended product with a UBS tail. This extended product can be quantified by SYBR Green qPCR using a specific locked nucleic acid primer ((LNA) (a DNA modification that increases the affinity of hybridization approximately 5° C. per base pair) and a universal primer. FIG. 14 sets forth SEQ ID NOs:106-107.

FIG. 14B is a graph of the amount of shRNA/cell in the recited clones. Small fraction enriched RNA was purified from PFF clones according to manufacturer's protocol using the PURELINK miRNA kit (Invitrogen Carlsbad, Calif.). Quantification was performed as detailed in FIG. 14A and copy number was calculated by the equation of the standard curve (inset).

DETAILED DESCRIPTION

Figure 2:
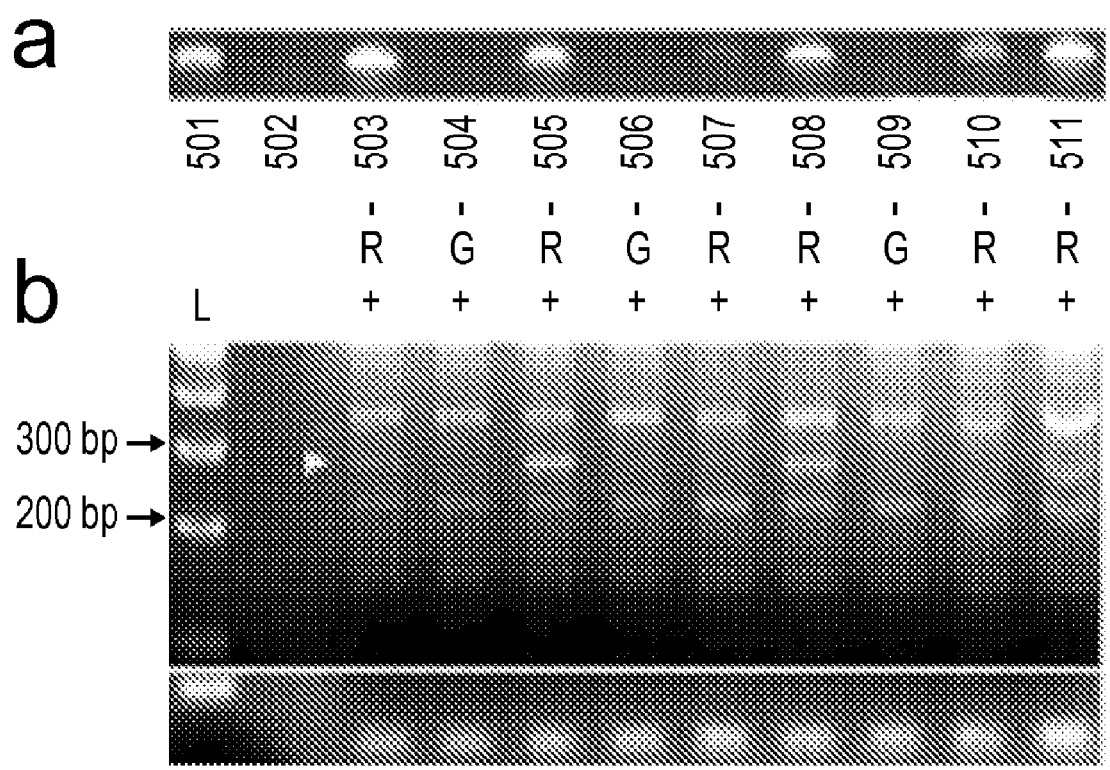
FIG. 2A depicts the genotyping of founder animals #501-511 using primers (black arrows of FIG. 1) specific to the BSD:GFP gene and miR30-Rab38 sequences. Seven of 11 rats were PCR positive for the transgene.
FIG. 2b depicts that nine animals (#503-511), including 6 of the 7 transgenics (arrows R), were tested for expression by RT-PCR using primers specific to the CLP promoter and BSD:GFP sequences (arrows G, FIG. 1a). Amid some background bands, the expected 277-bp product amplified from 4 of the 6 transgenic animals (white arrowhead).

As described herein, transposons and recombinases are capable of mobilizing DNA into and out of an artiodactyl (e.g., pig, cow, sheep, or goat) genome in a precise and efficient manner, providing the basis for developing transposon and recombinase based tools for genetic engineering of artiodactyls. In some embodiments, cytosine-phosphodiester-guanine (CpG) hypermethylated transposon transgenes and pronuclear injection can be used to achieve enhanced germline transgenesis rates in artiodactyls with efficiencies ranging from 50-90%. Without being bound to a particular mechanism, the artificially introduced methylation patterns are subsequently reprogrammed in the early embryo, reliably leading to founders which express the desired transgene.

Nucleic Acid Constructs

Nucleic acid constructs that can be used to produce transgenic animals include a target nucleic acid sequence. As used herein, the term "nucleic acid" includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) *Antisense Nucleic Acid Drug Dev.* 7(3):187-195; and Hyrup et al. (1996) *Bioorgan. Med. Chem.* 4(1):5-23. In addition, the deoxyphosphate backbone can be replaced with, for example, a phosphorothioate or phosphorodithioate backbone, a phosphoroamidite, or an alkyl phosphotriester backbone.

The target nucleic acid sequence can be operably linked to a regulatory region such as a promoter. Regulatory regions can be porcine regulatory regions or can be from other species. As used herein, "operably linked" refers to positioning of a regulatory region relative to a nucleic acid sequence in such a way as to permit or facilitate transcription of the target nucleic acid.

Any type of promoter can be operably linked to a target nucleic acid sequence. Examples of promoters include, without limitation, tissue-specific promoters, constitutive promoters, and promoters responsive or unresponsive to a particular stimulus. Suitable tissue specific promoters can result in preferential expression of a nucleic acid transcript in θ cells and include, for example, the human insulin promoter. Other tissue specific promoters can result in preferential expression in, for example, hepatocytes or heart tissue and can include the albumin or alpha-myosin heavy chain promoters, respectively.

In other embodiments, a promoter that facilitates the expression of a nucleic acid molecule without significant tissue- or temporal-specificity can be used (i.e., a constitutive promoter). For example, a beta-actin promoter such as the chicken θ-actin gene promoter, ubiquitin promoter, mini-CAGs promoter, glyceraldehyde-3-phosphate dehydrogenase (GAPDH) promoter, or 3-phosphoglycerate kinase (PGK) promoter can be used, as well as viral promoters such as the herpes virus thymidine kinase (TK) promoter, the SV40 promoter, or a cytomegalovirus (CMV) promoter. In some embodiments, a fusion of the chicken θ actin gene promoter and the CMV enhancer is used as a promoter. See, for example, Xu et al. (2001) *Hum. Gene Ther.* 12(5):563-73; and Kiwaki et al. (1996) *Hum. Gene Ther.* 7(7):821-30.

An example of an inducible promoter is the tetracycline (tet)-on promoter system, which can be used to regulate transcription of the nucleic acid. In this system, a mutated Tet repressor (TetR) is fused to the activation domain of herpes simplex VP 16 (transactivator protein) to create a tetracycline-controlled transcriptional activator (tTA), which is regulated by tet or doxycycline (dox). In the absence of antibiotic, transcription is minimal, while in the presence of tet or dox, transcription is induced. Another derivative of the tetracycline systems uses a fusion of the tetR protein to the Krüppel-associated box domain (KRAB) wherein the fusion protein directs transgene silencing to the targeted locus regulated by the presence (rtetR-KRAB fusion) or absence of dox or tet (tetR-KRAB fusion) (Szulc et al. 2006; *Nature Methods*). Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

Other elements that can be included on a nucleic acid construct encode signal peptides or selectable markers. Signal peptides can be used such that an encoded polypeptide is directed to a particular cellular location (e.g., the cell surface). Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture. Other selectable markers include fluorescent polypeptides, such as green fluorescent protein or yellow fluorescent protein.

In some embodiments, a sequence encoding a selectable marker can be flanked by recognition sequences for a recombinase such as, e.g., Cre or Flp. For example, the selectable marker can be flanked by loxP recognition sites (34 by recognition sites recognized by the Cre recombinase) or FRT recognition sites such that the selectable marker can be excised from the construct. See, Orban, et al., *Proc. Natl. Acad. Sci.* (1992) 89 (15): 6861-6865, for a review of Cre/lox technology, and Brand and Dymecki, *Dev. Cell* (2004) 6(1): 7-28. A transposon containing a Cre- or Flp-activatable transgene interrupted by a selectable marker gene also can be used to obtain transgenic animals with conditional expression of a transgene. For example, a promoter driving expression of the marker/transgene can be either ubiquitous or tissue-specific, which would result in the ubiquitous or tissue-specific expression of the marker in F0 animals (e.g., pigs). Tissue specific activation of the transgene can be accomplished, for example, by crossing a pig that ubiquitously expresses a marker-interrupted transgene to a pig expressing Cre or Flp in a tissue-specific manner, or by crossing a pig that expresses a marker-interrupted transgene in a tissue-specific manner to a pig that ubiquitously expresses Cre or Flp recombinase. Controlled expression of the transgene or controlled excision of the marker allows expression of the transgene.

In some embodiments, the target nucleic acid encodes a polypeptide. A nucleic acid sequence encoding a polypeptide can include a tag sequence that encodes a "tag" designed to facilitate subsequent manipulation of the encoded polypeptide (e.g., to facilitate localization or detection). Tag sequences can be inserted in the nucleic acid sequence encoding the polypeptide such that the encoded tag is located at either the carboxyl or amino terminus of the polypeptide. Non-limiting examples of encoded tags include glutathione S-transferase (GST) and Flag™ tag (Kodak, New Haven, Conn.). In other embodiments, the target nucleic acid sequence induces RNA interference against a target nucleic acid such that expression of the target nucleic acid is reduced. For example the target nucleic acid sequence can induce RNA interference against a nucleic acid encoding a cystic fibrosis transmembrane conductance regulatory (CFTR) polypeptide. For example, double-stranded small interfering RNA (siRNA) or small hairpin RNA (shRNA) homologous to a CFTR mRNA can be used to reduce expression of that mRNA. The term "siRNA" is used herein to include shRNAs, both of which are effector molecules in the process of RNA interference (RNAi). Such siRNAs for reduction of pig CFTR have been previously described but are not limited to the following sequences from Palmer et al., *J Cell Physiol.* 2006 March; 206(3):759-70 and are therein referred to as shCFTR1 (5' GCATGCAGATGAGAATAGCTA) shCFTR2 (5' and shCFTR3 (5' GAAGTAGTGATGGAGAATGTA) and shCFTR3 (5' GAAGAAGAGGTGCAAGATACA). Other variations thereof created by guidelines outlined below could also be capable of CFTR reduction in pigs.

RNAi as an Alternative to Knockout Models

RNAi is an evolutionarily conserved surveillance mechanism that responds to double-stranded RNA by sequence-specific silencing of gene expression. Stable expression of short hairpin RNA (shRNA) in eukaryotic cells using H1, U6, and 7S K pol III promoters {Brummelkamp, 2002, 11910072; Miyagishi, 2002, 11981564; Paul, 2002, 11981566; Sui, 2002, 11960009}, as well as PolII promoters {Denti, 2004, 15272480} has proven effective for the elimination of mRNA transcribed from targeted transgenes. This approach has been widely used to study gene function in cellular models and has been quite successfully applied to mice by tandem mouse ES cell transfection/tetraploied embryo aggregation {Kunath, 2003, 12679785; Lickert, 2005, 15857914; Lickert, 2004, 15525990}. Encouraging results were also reported after PNI of RNAi expression cassettes in mice and rats {Hasuwa, 2002 #392}. However, Carmell et. al. 2003 reported failure to generate a phenotype for several targets by PNI in mice, although the same constructs were able to knockdown Neil-1 by ES cell transgenesis and blastocysts injection {Carmell, 2003 #393}. Cao et. al. noted an interferon response to expressed silencer RNA duplexes {Cao, 2005, 15876690}, an observation also made by others in cultured cells and somatic tissues {Fish, 2004, 15291968; Grimm, 2006, 16724069}. Approaches to modulate efficacy and toxicity by modifying the length and sequence of shRNA's will likely aid in the development of stable RNAi in vivo {Fish, 2004, 15291968; Gasior, 2006, 16359634; Grimm, 2006, 16724069}, as will comparing the features of problematic versus successful shRNA expression cassettes. Indeed, Peng et. al. 2006 recently observed RNAi mediated mouse phenotypes after PNI without toxicity {Peng, 2006 #388}. In addition, we were able to recapitulate phenotypes associated with knockout of the CFTR gene in F1 mice generated by PNI. These observations as well as the CFTR pig model exemplified herein coupled with a demonstrated efficacy of RNAi in pig cells {Palmer, 2006 #287} suggests an efficient, dominant and specific approach to developing transgenic pigs by PNI (or SCNT).

Diseases Recapitulated by RNAi.

RNAi can be used for temporal or tissue specific reduction (herein referred to as knockdown) of tumor suppressor transcripts for generation cancer susceptible animal models. Such transcripts include; p53, pRb, APC, NF1, NF2, WT1, TSC1, TSC2, DPC4/SMAD4, DCC, BRCA1, BRCA2, LKB1, MSH2, MLH1, CDH1, CDKN2A, PTCH and MEN1.

RNAi can be used for temporal or tissue specific knockdown of genes (in parenthesis) linked to human single gene disorders including; Muscular dystrophy of Duchene and Becker types (Dystrophin); familial Alzheimer disease (APP); Fanconi anemia (FANCA, FANCC, FANCE, FANCF, FANCG, FANCJ); Hemophilia A (Factor VIII); Hemophilia B (Factor IX); myotonic dystrophy (DMPK); Huntington disease (HD); Osteogenesis imperfect (COL1A1 or COL1A2); polycystic kidney disease (PKD1 or PKD2); Retinitis pigmentosa (multiple targets); spinal muscular atrophy (SMA1); Severe Combine Immune Deficiency (IL2RG or JAK3 or ADA or IL7R alpha or CD3 delta or epsilon, RAG1/RAG2 or ARTEMIS or CD45); Type I Diabetes (all transcripts located within genetic loci IDDM1 to IDDM18); Type II Diabetes (PAX4 or TFAP2B or ABCC8 or IRS1 or insulin receptor or GCK or Kir6.2); atherosclerosis (LDLR, ATHS).

RNAi can also be used to model cellular hypoplasias knockdown of transcripts required for viability in muscle, heart, lung, pancreas, liver, kidney, bone and nervous system.

RNAi can also be used to model channelopathies other the cystic fibrosis by knockdown of ion channel transcripts including: SCN1A, SCN2A, SCN4A, SCN5A, SCN1B, KCNQ1, KCNH2, KCNJ2, KCNH2, ANKB, CACNA2, KCNJ11, SUR1, SUR2, KCNE1, KCNE2, ABCC7, CLCN1, CLCN5, CLCN7, CLCNKB, RYR1, RyR2, GABRG2, CHRNA4, CHRNB2, GLRA1). Basic design parameters for effective siRNAs have been described by several groups Li, *RNA* (2007) 13: 1765-1774; Taxman *BMC Biotechnol.* (2006); 6: 7; Amarzguioui, *Biochem. Biophys. Res. Commun.* 316, 1050-1058 (2004); Reynolds, *Nat. Biotechnoly.* 22, 326-330 (2004). Several web-based RNAi design tools incorporate guidelines of the above studies to generate effective siRNAs targeted to an mRNA of choice (e.g., as at www.ambion.com or [http://site] sfold.wadsworth.org or www.sirnawizard.com).

Embodiments of the invention thus include creating transgenic pigs or artiodactyls that express one or more of the RNAi (siRNA) set forth herein. Materials and methods used herein may be used for their introduction. For instance a transposase system may be used, e.g., one of the SBs, or Passport.

Constructs for siRNA can be produced as described, for example, in Fire et al. (1998) *Nature* 391:806-811; Romano and Masino (1992) *Mol. Microbiol.* 6:3343-3353; Cogoni et al. (1996) *EMBO J.* 15:3153-3163; Cogoni and Masino (1999) *Nature* 399:166-169; Misquitta and Paterson (1999) *Proc. Natl. Acad. Sci. USA* 96:1451-1456; and Kennerdell and Carthew (1998) *Cell* 95:1017-1026. Constructs for shRNA can be produced as described by McIntyre and Fanning (2006) *BMC Biotechnology* 6:1. In general, shRNAs are transcribed as a single-stranded RNA molecule containing complementary regions, which can anneal and form short hairpins. RNAi is described in greater detail elsewhere (Yin and Wan, 2002; Scherer and Rossi, 2003) and below. As categorized by Yin and Wan, RNAi includes long double stranded RNAs, long single stranded sense RNA, single stranded RNAs that form duplexes, short double stranded RNAs, and short antisense RNAs. RNAi is the subject of U.S. patent and PCT applications, e.g., certain of the following: US20030125281; US20030130186; US20030124513; US20030119017; US20030144239; US20030166282; US20030148519; US20030157691; US20030153519; US20030139363; US20030166512; US20030036056; WO03056022; WO03020931; WO03008573; WO0244321; WO03070895; WO03070193; WO03070750; WO03070918; WO03070914; WO03066650; WO03068797; WO02097114; WO9946372; WO0060115; WO9519788; WO9206988; and U.S. Pat. No. 6,562,570 U.S. Pat. No. 5,985,661. U.S. Pat. No. 5,750,380 U.S. Pat. No. 5,750,380 U.S. Pat. No. 5,272,262 U.S. Pat. No. 5,149,796; U.S. Pat. No. 5,144,019; and U.S. Pat. No. 5,110,802. Use of RNAi and shRNA and other materials and methods as described in these publications is contemplated in combinations with the embodiments described elsewhere herein. Further siRNAs and methods of generating them or using them are described, e.g., in U.S. Pat. No. 7,422,853, U.S. Pat. No. 7,452,987, U.S. Pat. No. 7,195,916, U.S. Pat. No. 7,524,653, US20050260270, U.S. Pat. No. 7,459,547, U.S. Pat. No. 7,078,196, and U.S. Pat. No. 7,507,811.

Indeed, a variety of siRNAs may be applied to the creation of artiodactyls by following the methods used herein. Some examples of siRNAs are set forth in U.S. Pat. No. 7,517,864, U.S. Pat. No. 7,345,027, or U.S. Pat. No. 7,176,304 that describe compounds, compositions, and methods useful for modulating VEGF and/or VEGFR gene expression using short interfering nucleic acid (siRNA) molecules. And U.S. Pat. No. 7,423,142 describes siRNAs for an anti-apoptotic gene such as a Bcl gene. And US20080038308 describes siRNA molecules that down-regulate the expression of proteins that inhibit bone formation. And U.S. Pat. No. 7,399,586 describes siRNA polynucleotides that interfere with expression of members of the protein tyrosine phosphatase (PTP) class of enzymes that mediate signal transduction. And US20090169638 describes siRNA inhibitors of ribonucleotide reductase subunit 2 (R2). And U.S. Pat. No. 7,541,344 describes siRNAs for modulation of survivin expression. And U.S. Pat. No. 7,507,810 describes compositions and their uses directed to IL-4R alpha. And U.S. Pat. No. 7,425,544 describes modulation of eIF4E expression with siRNAs. US20070219148 describes siRNA specific to sub-units α, α and β of the kinase protein CK2. And US20090029934 describes siRNA molecules targeted against a gene of interest in respiratory epithelial cells. Nucleic acid constructs can be methylated using an SssI CpG methylase (New England Biolabs, Ipswich, Mass.). In general, the nucleic acid construct can be incubated with S-adenosylmethionine and SssI CpG-methylase in buffer at 37° C. Hypermethylation can be confirmed by incubating the construct with one unit of HinP1I endonuclease for 1 hour at 37° C. and assaying by agarose gel electrophoresis.

Nucleic acid constructs can be introduced into embryonic, fetal, or adult porcine cells of any type, including, for example, germ cells such as an oocyte or an egg, a progenitor cell, an adult or embryonic stem cell, a kidney cell such as a PK-15 cell, an islet cell, a beta cell, a liver cell, or a fibroblast such as a dermal fibroblast, using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

In transposon systems, the transcriptional unit of a nucleic acid construct, i.e., the regulatory region operably linked to a target nucleic acid sequence, is flanked by an inverted repeat of a transposon. Several transposon systems, including, for example, Sleeping Beauty (see, U.S. Pat. No. 6,613,752 and U.S. Patent Publication No. 20050003542); Frog Prince (Miskey et al. (2003) *Nucleic Acids Res.* 31(23):6873-81; US20050241007); Tol2 (Kawakami (2007) *Genome Biology* 8 (Suppl.1):S7, US20050177890, U.S. Pat. No. 7,034,115); Minos (Pavlopoulos et al. (2007) *Genome Biology* 8(Suppl.1):S2); Hsmar1 (Miskey et al. (2007)) *Mol Cell Biol.* 27(12):4589-600); Piggybac (US20090042297, US20070204356); and Passport (Leaver (2001) *Gene,* 271 (2), 203-214, U.S. Ser. No. 61/081,324 filed Jul. 16, 2008 and copending U.S. Ser. No. 12/504,286 entitled "Plaice DNA Transposon System" filed Jul. 17, 2009, both by Fahrenkrug et al.) have been developed to introduce nucleic acids into cells, including mice, human, and pig cells. The Sleeping Beauty transposon is particularly useful. A transposase can be encoded on the same nucleic acid construct as the target nucleic acid, can be introduced on a separate nucleic acid construct, or provided as an mRNA (e.g., an in vitro transcribed and capped mRNA).

Insulator elements also can be included in a nucleic acid construct to maintain expression of the target nucleic acid and to inhibit the unwanted transcription of host genes. See, for example, U.S. Patent Publication No. 20040203158. Typically, an insulator element flanks each side of the transcriptional unit and is internal to the inverted repeat of the transposon. Non-limiting examples of insulator elements include the matrix attachment region (MAR) type insulator elements and border-type insulator elements. See, for example, U.S. Pat. Nos. 6,395,549, 5,731,178, 6,100,448, and 5,610,053, and U.S. Patent Publication No. 20040203158.

Transgenic Artiodactyls

This document features transgenic artiodactyls (e.g., pigs, sheep, goats, and cows). The nucleated cells of the transgenic artiodactyls provided herein contain a nucleic acid construct described above. As used herein, "transgenic artiodactyl" includes founder transgenic artiodactyls as well as progeny of the founders, progeny of the progeny, and so forth, provided that the progeny retain the nucleic acid construct. For example, a transgenic founder animal can be used to breed additional animals that contain the nucleic acid construct. Transgenic pigs are particularly useful.

Tissues obtained from the transgenic artiodactyls (e.g., transgenic pigs) and cells derived from the transgenic artiodactyls (e.g., transgenic pigs) also are provided herein. As used herein, "derived from" indicates that the cells can be isolated directly from the animal or can be progeny of such cells. For example, brain, lung, liver, pancreas, heart and heart valves, muscle, kidney, thyroid, corneal, skin, blood vessels or other connective tissue can be obtained from a transgenic artiodactyl (e.g., transgenic pig). Blood and hematopoietic cells, Islets of Langerhans, beta cells, brain cells, hepatocytes, kidney cells, and cells from other organs and body fluids, for example, also can be derived from transgenic artiodactyls (e.g., transgenic pigs). Organs and cells from transgenic pigs can be transplanted into a human patient. For example, islets from transgenic pigs can be transplanted to human diabetic patients.

Various techniques known in the art can be used to introduce nucleic acid constructs into non-human animals to produce founder lines, in which the nucleic acid construct is integrated into the genome. Such techniques include, without limitation, pronuclear microinjection (U.S. Pat. No. 4,873, 191), retrovirus mediated gene transfer into germ lines (Van der Putten et al. (1985) *Proc. Natl. Acad. Sci. USA* 82, 6148-1652), gene targeting into embryonic stem cells (Thompson et al. (1989) *Cell* 56, 313-321), electroporation of embryos (Lo (1983) *Mol. Cell. Biol.* 3, 1803-1814), sperm mediated gene transfer (Lavitrano et al. (2002) *Proc. Natl. Acad. Sci. USA* 99, 14230-14235; Lavitrano et al. (2006) *Reprod. Fert. Develop.* 18, 19-23), and in vitro transformation of somatic cells, such as cumulus or mammary cells, or adult, fetal, or embryonic stem cells, followed by nuclear transplantation (Wilmut et al. (1997) *Nature* 385, 810-813; and Wakayama et al. (1998) Nature 394, 369-374). Pronuclear microinjection, sperm mediated gene transfer, and somatic cell nuclear transfer are particularly useful techniques.

Typically, in pronuclear microinjection, a nucleic acid construct described above is introduced into a fertilized egg; 1 or 2 cell fertilized eggs are used as the pronuclei containing the genetic material from the sperm head and the egg are visible within the protoplasm. Pronuclear staged fertilized eggs can be obtained in vitro or in vivo (i.e., surgically recovered from the oviduct of donor animals). In vitro fertilized eggs can be produced as follows. For example, swine ovaries can be collected at an abattoir, and maintained at 22-28° C. during transport. Ovaries can be washed and isolated for follicular aspiration, and follicles ranging from 4-8 mm can be aspirated into 50 mL conical centrifuge tubes using 18 gauge needles and under vacuum. Follicular fluid and aspirated oocytes can be rinsed through pre-filters with commercial TL-HEPES (Minitube, Verona, Wis.). Oocytes surrounded by a compact cumulus mass can be selected and placed into TCM-199 Oocyte Maturation Medium (Minitube, Verona, Wis.) supplemented with 0.1 mg/mL cysteine, 10 ng/mL epidermal growth factor, 10% porcine follicular fluid, 50 µM 2-mercaptoethanol, 0.5 mg/ml cAMP, 10 IU/mL each of pregnant mare serum gonadotropin (PMSG) and human chorionic gonadotropin (hCG) for approximately 22 hours in humidified air at 38.7° C. and 5% $CO_2$. Subsequently, the oocytes can be moved to fresh TCM-199 maturation medium which will not contain cAMP, PMSG or hCG and incubated for an additional 22 hours. Matured oocytes can be stripped of their cumulus cells by vortexing in 0.1% hyaluronidase for 1 minute.

Mature oocytes can be fertilized in 500 µl MINITUBE PORCPRO IVF MEDIUM SYSTEM (Minitube, Verona, Wis.) in Minitube 5-well fertilization dishes. In preparation for in vitro fertilization (IVF), freshly-collected or frozen boar semen can be washed and resuspended in PORCPRO IVF Medium to $4 \times 10^5$ sperm. Sperm concentrations can be analyzed by computer assisted semen analysis (SPERMVISION, Minitube, Verona, Wis.). Final in vitro insemination can be performed in a 10 µl volume at a final concentration of approximately 40 motile sperm/oocyte, depending on boar. Incubate all fertilizing oocytes at 38.7° C. in 5.0% $CO_2$ atmosphere for 6 hours. Six hours post-insemination, presumptive zygotes can be washed twice in NCSU-23 and moved to 0.5 mL of the same medium. This system can produce 20-30% blastocysts routinely across most boars with a 10-30% polyspermic insemination rate.

Linearized nucleic acid constructs can be injected into one of the pronuclei then the injected eggs can be transferred to a recipient female (e.g., into the oviducts of a recipient female) and allowed to develop in the recipient female to produce the transgenic animals. In particular, in vitro fertilized embryos can be centrifuged at 15,000×g for 5 minutes to sediment lipids allowing visualization of the pronucleus. The embryos can be injected with approximately 5 picoliters of the transposon/transposase cocktail using an Eppendorf FEMTOJET injector and can be cultured until blastocyst formation (~144 hours) in NCSU 23 medium (see, e.g., WO/2006/036975). Rates of embryo cleavage and blastocyst formation and quality can be recorded.

Embryos can be surgically transferred into uteri of asynchronous recipients. For surgical embryo transfer, anesthesia can be induced with a combination of the following: ketamine (2 mg/kg); tiletamine/zolazepam (0.25 mg/kg); xylazine (1 mg/kg); and atropine (0.03 mg/kg) (all from Columbus Serum). While in dorsal recumbency, the recipients can be aseptically prepared for surgery and a caudal ventral incision can be made to expose and examine the reproductive tract. Typically, 100-200 (e.g., 150-200) embryos can be deposited into the ampulla-isthmus junction of the oviduct using a 5.5-inch TOMCAT® catheter. After surgery, real-time ultrasound examination of pregnancy can be performed using an ALOKA 900 ULTRASOUND SCANNEr (Aloka Co. Ltd, Wallingford, Conn.) with an attached 3.5 MHz trans-abdominal probe. Monitoring for pregnancy initiation can begin at 23 days post fusion and can be repeated weekly during pregnancy. Recipient husbandry can be maintained as normal gestating sows.

In somatic cell nuclear transfer, a transgenic artiodactyl cell (e.g., a transgenic pig cell) such as an embryonic blastomere, fetal fibroblast, adult ear fibroblast, or granulosa cell that includes a nucleic acid construct described above, can be introduced into an enucleated oocyte to establish a combined cell. Oocytes can be enucleated by partial zona dissection near the polar body and then pressing out cytoplasm at the dissection area. Typically, an injection pipette with a sharp beveled tip is used to inject the transgenic cell into an enucleated oocyte arrested at meiosis 2. In some conventions, oocytes arrested at meiosis 2 are termed "eggs." After producing a porcine embryo (e.g., by fusing and activating the oocyte), the porcine embryo is transferred to the oviducts of a recipient female, about 20 to 24 hours after activation. See, for example, Cibelli et al. (1998) *Science* 280, 1256-1258 and U.S. Pat. No. 6,548,741. For pigs, recipient females can be checked for pregnancy approximately 20-21 days after transfer of the embryos.

Standard breeding techniques can be used to create animals that are homozygous for the target nucleic acid from the initial heterozygous founder animals. Homozygosity may not be required, however. Transgenic pigs described herein can be bred with other pigs of interest.

Conventional transgenesis with naked DNA tends to insert a plurality of exogenous gene copies into one site (making a concatemer of inserts). When conventionally-produced transgenic founders are thus created, transfection of donor cells for SCNT or pronuclear injection of one cell embryos is performed followed by screening for exogenous gene insertion: these animals are identified as founders and typically have one chromosome modified and have offspring with that same modification and potential for transgene expression and physiological consequence.

In contrast, the transposons were observed to make more useful transgenic founder animals. The animals received exogenous gene insertions at a plurality of chromosomal sites. The founders could then be bred and the offspring tested for the presence of exogenous genes. Since the founder had a plurality of sites and/or chromosomes altered, sexually generated offspring can inherit one or less than all of the alterations and can then be tested for desirable traits. The expression of exogenous genes and the effect of such genes on the physiology of the transgenic animals varies according to the number of copies and the serendipity of the insertion's proximity to a favorable promoter or avoidance of a mutagenic placement. The transposon-based founders thus had more opportunities for producing desirable offspring because there were insertions made at various chromosomal locales. But the conventionally-produced animals typically have about one site that is modified so that, if the founder does not turn out to be desirable, more animals have to be treated. Thus the use of transposons creates a substantially more efficient process because one founder yields a plurality of opportunities for a good outcome, so that fewer founders have to be created. Accordingly, embodiments include using a transposon-driven transfection scheme to create a transgenic founder and may include breeding the founder with non-treated animals to generate a generation of offspring having a distribution of the plurality of altered genes present in the parent founder.

In some embodiments, a nucleic acid of interest and a selectable marker can be provided on separate transposons and provided to either embryos or cells in unequal amount, where the amount of transposon containing nucleic acid of interest far exceeds (at least 3-10 fold excess; artisans will immediately appreciate that all ranges and values between the explicitly stated values are contemplated, e.g., at least a 5-fold excess, a 5 to 10-fold excess, or about 7-fold excess) the transposon containing the selectable marker. Transgenic cells or animals expressing the nucleic acid of interest can be isolated based on presence and expression of the selectable marker. Because the transposons will integrate into the genome in a precise and unlinked way (independent transposition events), the nucleic acid of interest and the selectable marker are not genetically linked and can easily be separated by genetic segregation through standard breeding. Thus, transgenic animals can be produced that are not constrained to retain selectable markers in subsequent generations. Accordingly, embodiments include delivering a plurality of transposons with distinct exogenous nucleic acids to an artiodactyl to create a transgenic animal expressing the plurality of exogenous nucleic acids, and subsequently breeding at least one of the exogenous nucleic acids out of the animal's offspring. For instance, a first sequence may code a marker and a second sequence encode a nucleic acid of interest. Similarly, there may be a plurality of nucleic acids of interest that are introduced to an animal to create a founder, with subsequent breeding being used to select for one or more of the nucleic acids of interest. Thus an animal may be bred to produce a desired combination of genes, or an animal may be transfected with more than one gene with the expectation that breeding will provide for more than one transgenic animal line.

Once transgenic animals have been generated, expression of a target nucleic acid can be assessed using standard techniques. Initial screening can be accomplished by Southern blot analysis to determine whether or not integration of the construct has taken place. For a description of Southern analysis, see sections 9.37-9.52 of Sambrook et al., 1989, *Molecular Cloning, A Laboratory Manual*, second edition, Cold Spring Harbor Press, Plainview; NY. Polymerase chain reaction (PCR) techniques also can be used in the initial screening. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example *PCR Primer: A Laboratory Manual*, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis (1992) *Genetic Engineering News* 12,1; Guatelli et al. (1990) *Proc. Natl. Acad. Sci. USA* 87, 1874-1878; and Weiss (1991) *Science* 254, 1292-1293. At the blastocyst stage, embryos can be individually processed for analysis by PCR, Southern hybridization and splinkerette PCR (see, e.g., Dupuy et al. *Proc Natl Acad Sci USA* (2002) 99(7):4495-4499).

Expression of a nucleic acid sequence encoding a polypeptide in the tissues of transgenic pigs can be assessed using techniques that include, without limitation, Northern blot analysis of tissue samples obtained from the animal, in situ hybridization analysis, Western analysis, immunoassays such as enzyme-linked immunosorbent assays, and reverse-transcriptase PCR (RT-PCR).

The invention will be further described in the following examples, which do not limit the scope of the invention described in the claims.

EXAMPLES

Example 1

Mammalian Germline Transgenesis Catalyzed by Chemically Modified Transposons

Materials and Methods
Preparation of CpG-Methylated Transposon Substrates

Transposon plasmids were treated with SssI CpG methylase (New England Biolabs, Ipswich, Mass.) according to the manufacturer's recommendations. Briefly, Qiagen (Valencia, Calif.) kit-prepped plasmid DNA was resuspended in 1×NEB buffer 2 at 20 μg/mL and supplemented with 160 μM S-adenosylmethionine and 1 unit/μg of active, or heat inactivated (65° C., 20 min), SssI CpG-methylase and incubated at 37° C. for one hour. Hypermethylation was confirmed by cutting 100 ng of treated sample with one unit of HinP1I endonuclease for 1 hour at 37° C. and assayed by agarose gel electrophoresis.

For animal transgenesis, the pT2/sh_mCFTR1 and pKT2/KDRab38 transposon plasmids were linearized with ApaLI endonuclease, and the pKT2/HSA-CCTG300 transposon with AseI after methylase treatment. The mouse transgenes were purified after gel electrophoresis using the ULTRA-CLEAN 15 DNA Purification Kit (MoBio, Carlsbad, Calif.), ethanol precipitated twice, and resuspended in injection buffer (5 mM Tris-Cl pH 7.5, 0.1 mM EDTA) before serial dialysis three times against 500 mL of injection buffer using SLIDE-A-LYZER CASSETTES (10,000 MWCO, Pierce, Rockford, Ill.). The rat transgene was purified using a NUCLEOSPIN kit (Clontech, Mountain View, Calif.) as described by Filipiak and Saunders (*Transgenic Res.* 15:673-686 (2006)). SB11 mRNA was prepared using the Ambion (Austin, Tex.) MMESSAGE MMACHINE® T3 kit as described by Wilbur et al. (*Mol. Ther.* 13:625-30 (2006)) and mixed with transposon DNA at 15 ng/uL RNA, 5 ng/TL DNA the morning of injection, and maintained on ice before injection into FVB/N strain mouse embryos or Sprague Dawley strain rat embryos (both rodent strains from Charles River Laboratories) using standard techniques.

Southern Blot Analysis

T2_shmCFTR1 transgenic mouse tail biopsy DNA was extracted by Proteinase-K buffer digestion and phenol/chloroform extracted using a standard protocol. 10 μg of DNA was subjected to BamHI restriction endonuclease digestion and run on a 0.8% agarose gel. After transfer to a MAG-NAPROBE nylon membrane (GE Osmonics, Minnetonka, Minn.), the samples were probed by labeling the 1,117-bp NcoI fragment of the pT2/sh_mCFTR1 plasmid with I-$^{32}$P using a random-primer protocol and HEXANUCLEOTIDES (Roche, Indianapolis, Ind.). KT2/HSA-CCTG$_{300}$ transgenic mouse DNA was digested with EcoRI and probed with the 661-bp XhoI-BglII fragment of pKT2/HSA-CCTG$_{300}$ in the same manner.

Bisulfite-Mediated Genomic Sequencing

Bisulfite sequencing of transposon integrations was performed as described by Park et al. *Genes to Cells* 10:763-776 (2005) and Park et al *Genomics* 88:204-213 (2006). For the present study, liver genomic DNA was digested with restriction endonuclease EcoRI to fragment the genome and ensure complete DNA denaturation during bisulfite treatment. PCR primers for SV region were SVshF, [5'-TTATTATTTTTG-GAATAGTTTAGAGG] (SEQ ID NO:1), and SVshR, [5'-AAAATTCCAAAAAATAATATCATAAC] (SEQ ID NO:2); primers for region P were PuroF, [5'-TTGTGGTTTGTT-TAAATTTATTAATG] (SEQ ID NO:3), and PurM1R, [5'-CCACCAAAACAAAAATCTAAACAAC] (SEQ ID NO:4).

Tissue Culture Methods

In vitro analysis of transposition rates of nonmethylated and methylated transposon constructs was performed as described by Geurts et al. (*Mol. Ther.* 8:108-117 (2003)). 500 ng pCMV-SB11 and equal molar ratios of transposon plasmid, normalized to 500 ng pT2/SVNeo, were used for each transfection.

Transcript Quantification

Tissue samples (lung, liver, small intestine) were preserved in Rnalater® (Ambion) and RNA was isolated using the PURELINK miRNA isolation kit (Invitrogen, Carlsbad Calif.). Large fractions RNA (500 ng) from the small intestine was reverse transcribed with SUPERSCRIPT™ III, using random hexamers, according to the manufactures protocol (Invitrogen, Carlsbad Calif.). Quantitative PCR for puromycin ([5'-CGCCGCGTTCGCCGACTACC] (SEQ ID NO:5) and [5'-CGCCCCCGCTTCGACGCTCTC]) (SEQ ID NO:6) and Hypoxanthine-Guanine Phosphoribosyl Transferase (HPRT) ([5'-GCTTCCTCCTCAGACCGCTT] (SEQ ID NO:7) and [5'-GGTCAGCAAAGAACTTATAGCCCC]) (SEQ ID NO:8) were performed using IQ SYBR GREEN SUPERMIX (Biorad, Hercules, Calif.) on a MX3000P thermal cycler (Stratagene, La Jolla, Calif.). Puromycin expression was normalized to HPRT expression levels.

Short hairpin RNA directed against mouse Cftr (sh_mCFTR1) was detected using a modified primer-extension qPCR approach described by Raymond, et al. (*RNA* 11:1737-1744 (2005)). 0.25 pmol of a gene specific primer (GSP), [5'-GGGCAAGCAGTCCTAACAACCATGGAAT-GCAGA] (SEQ ID NO:9) designed against sh_mCFTR1 with a 9 base pair hybridization domain (bold) was used to reverse transcribe 50 ng of small fraction RNA from either the lungs or liver. A universal binding sequence (italics) is included for hybridization of a universal primer (UP), [5'-GGGCAAGCAGTCCTAACAACCATG] (SEQ ID NO:10). The product was quantified by SYBR Green using a short primer with locked nucleic acids (indicated lowercase) to raise hybridization temperature [5'-TagCTgTTCT-CATCTGC] (SEQ ID NO:11) and the UP primer. Total mCFTR1 was determined by comparison to a standard curve generated by qPCR of known amounts of mock template ranging from 8 to 800,000 copies per cell (based on the assumption that each cell contains 10 pg total RNA (see Raymond et al. 2005 supra) and that one-fifth of total RNA purifies in the small fraction when using the PURELINK miRNA isolation kit (data not shown).

Transgenic Rat PCR Genotyping and RT-PCR

Tail biopsy DNA from Sprague Dawley founder animals were screened by PCR for presence of the KT2/KDRab38 transposon with the primers GFP-T-F {5'-TCTCGGCATG-GACGAGCTGTACA] (SEQ ID NO:12) and miR30-EcoRI [5'-CTAAAGTAGCCCCTTGAATTCCGAG-GCAGTAGGCA] (SEQ ID NO:13) yielding a 339-bp product. RT-PCR was performed on tail biopsy total RNA, which was isolated with TRIZOL® (Invitrogen) and treated with DNASE I (Invitrogen), using CLP-F [5'-AAGCTTCTGCCT-TCTCCCTCC] (SEQ ID NO:14) and BSD:GFP-R [5'-AAGTCAGGTTGCCAGCTGCC] (SEQ ID NO:15), or GAPDH-F [5'-CCTCAAGATTGTCAGCAATG] (SEQ ID NO:16) and GAPDH-R [5'-ATCCACAGTCTTCT-GAGTGG] (SEQ ID NO:17), and the SUPERSCRIPT™ III ONE-STEP RT-PCR system (Invitrogen) under the following conditions: one cycle of 50° C. for 30', 30 cycles of 94° for 30", 55° for 30", 68° for 30", and a final 68° extension for 5'. RT-PCR yielded a 277-bp product after splicing of the 140-bp synthetic intron (FIG. 2A).

Results

Typically, hyperactive Sleeping Beauty transposases such as SB11 were used. See, Geurts et al. (2003) *Mol. Ther.* 8, 108-117; and Baus et al. (2005) *Mol. Ther.* 12, 1148-1156. The in vitro transcription vector for SB had an optimized kozak consensus sequence for initiation of translation (GXX-AUGG) (SEQ ID NO:18). The transposase gene was cloned between the 5' and 3' xenopus beta-globin UTRs. The T2/sh_mCFTR1, pKT2/HSA-CCTG$_{300}$, and pKT2/KD$^{Rab38}$ SB transposon-based transgenes (FIG. 1A) were generated for modeling single-gene human disorders in transgenic laboratory mice and rats while the pKT2H-CD40Ig transposon was designed to direct β-cell specific expression of the fusion protein CD40Ig (Noelle et al., *Immunology Today* 1992, 13(11):431-433). Cocktails for T2/sh_mCFTR1, pKT2/HSA-CCTG300, and pKT2H-CD40Ig transposons were prepared containing 5 ng/μL methylated or nonmethylated transposon donor plasmid substrate plus 15 ng/μL in vitro transcribed, capped SB11 transposase mRNA, and injected into wild type FVB/N strain pronuclei. Additional controls in the pKT2H-CD40Ig set of injections substituted a "dead" version of SB transposase (SB11ΔDDE) with both methylated and nonmethylated transposon substrate to determine if transgene methylation alone alters the frequency of genome integration. The pKT2/KD$^{Rab38}$ transgene was prepared only as a methylated transgene and injected under the same conditions into Sprague Dawley (SD) rat embryos. Injected embryos were transferred to the oviduct of pseudopregnant females and carried to parturition.

Table 1 summarizes the efficiency of gene transfer to mouse and rat embryos by methylated and nomethylated SB transposon transgenes as determined by Southern blot or PCR analysis of founder tail biopsy DNA. Southern blot analysis revealed that in the presence of SB11 transposase, 18 of 20 and 44 of 55 live born mice injected with methylated T2/sh_mCFTR1 and KT2H-CD40Ig, respectively, were transgenic versus 4 of 16, and 15 of 25 when using the equivalent nonmethylated transposons (FIG. 1b and data not shown). Combining data from all transposons reveals the rate of transgenesis for non-methylated transposons to be around 45%±15%, while methylated transposons gave a transgenesis rate of 73%±15%, even including data from a very large Tn (see below).

TABLE 1

Germline transgenesis rates mediated by SB

| Vector | Host | Size (kb) | Founders generated | Transgenesis frequency (%) | Copy number[a] | Fraction expressing transgene[b] |
|---|---|---|---|---|---|---|
| SB Transposon Methylated | | | | | | |
| T2/sh_mCFTR1 | mouse | 2.3 | 20 | 90 | 1-8 SC, CC | 7/7 |
| KT2/HAS-CCTG$_{300}$ | mouse | 9.1 | 21 | 57 | 1-3 SC, CC | NA |
| KT2H-CD40Ig | mouse | 3 | 55 | 80 | 1-11 SC, CC | NA |
| KT2/KD$^{Rab38}$ | rat | 3.5 | 11 | 65 | 1-4 SC, CC | 4/6 |
| nonmethylated | | | | | | |
| T2/sh_mCFTR1 | mouse | 2.3 | 16 | 25 | 1 SC | 2/2 |
| KT2/HSA-CCTG$_{300}$ | mouse | 9.1 | 21 | 52 | 1-3 SC, CC | NA |
| KT2H-CD40Ig | mouse | 3 | 25 | 60 | 1-9 SC, CC | NA |
| T/K14-Agouti[c] | mouse | 4.3 | 20 | 45 | 1-5 SC, CC | 6/9 |

[a]SC—single copy transposition, CC - multicopy concatemer
[b]NA—not assayed
[c]Dupuy et. al. 2002

Transgenic founders from both groups harbored both single-copy transposition events and multi-copy concatemers (FIG. 1b), reflecting both TnT and random, nonhomologous integration, respectively. Beyond enhancement on a per/animal transgenesis rate, the use of methylated transposons significantly increases the number of transposase mediated insertions per founder (Table 2). Most significant is the 2-4 fold increase in the incidence of concatemer-free transgenic founders for methylated T2/sh_mCFTR1 and KT2H-CD40Ig transposons, and amongst these, an elevated number of transgenes per genome over the nonmethylated equivalent. Interestingly, in the presence of a transgene concatemer, the number of transpositions per founder is nearly equivalent for methylated and nonmethylated transposons, suggesting that integration of a concatemer acts as a seed for subsequent transposition events in the embryo (since the only source of transposase is mRNA). Given the association of deletions with concatemers, particularly in the presence of active transposase, concatemer confounded founders should be avoided when propagating transgenic lines. More importantly, the use of supercoiled instead of linearized transposon may eliminate the occurrence of concatemers, since DSB would not be available for NHEJ for array formation prior to integration. Supercoiled is the native form of plasmid extracted from bacteria. Linearized DNA has generally been treated with a restriction enzyme thereby opening up the supercoiled circular plasmid into linear form. Methylation is a chemical modification that can be applied to linear or supercoiled DNA, but is not required to produce either.

TABLE 2

Transgene architecture and copy number

| Transposon | Condition | | Transgenic (percent) | Num. with TnT[a] (avg. Tn per pup) | Num. with C[c] (% liveborn) | TnT in C lines (per pup) | Num. w/ TnT only (% liveborn) | TnT in NC[c] lines (per pup) |
|---|---|---|---|---|---|---|---|---|
| | CpG | SB11 | | | | | | |
| KT2H-CD40Ig | + | + | 44 (80) | 44 (4.36) | 13 (23.5) | 58 (3.57) | 30 (55) | 134 (4.46) |
| KT2H-CD40Ig | − | + | 15 (60) | 15 (2.66) | 7 (28) | 27 (3.85) | 8 (32) | 13 (1.63) |
| KT2H-CD40Ig | + | − | 5 (14.7) | NA | 5 | 0 | NA | 0 |
| KT2H-CD40Ig | − | − | 2 (18) | NA | 2 | 0 | NA | 0 |
| T2/shP2-mCFTR1 | + | + | 18 (90) | 18 (2.84) | 3 (15)[b] | 10 (3.33) | 15 (75) | 38 (2.53) |
| T2/shP2-mCFTR1 | − | + | 4 (25) | 4 (1) | 1 (6.25)[b] | 0 | 3 (18.75) | 4 (1.33) |
| KT2-HAS cctg(300) | + | + | 11 (52) | 7 (1.72) | 10 (48)[b] | 18 (1.8) | 1 (9) | 1 (1) |
| KT2-HAS cctg(300) | − | + | 12 (57) | 7 (1.25) | 11 (52)[b] | 14 (1.3) | 1 (8) | 1 (1) |
| T/K14 Agouti[d] | − | + | 19 (45) | NR | 13 (31) | NR | 6 (14) | 18 (3) |

[a]TnT - transposase mediated integration as determined from southern blot
[b]Determined by band intensity and size rather than vector hybridization
[c]C—concatemer, animal that includes inserts mediated by random incorporation, NC—non-concatemer
[d]Dupuy et. al., 2002
NR—not reported,
NA—not assayed Ideal sites for SB integration are scattered throughout the genome. Taken together, T2/sh_mCFTR1 and KT2H-CD40Ig concatemer free founders result in approximately 172 distinct linkage groups (2.3 per liveborn offspring) compared to 17 (0.41 per liveborn offspring) using nonmethylated transposons. Therefore methylation-enhanced TnT resulted in approximately in nearly a log-fold increase in the number of potential transgenic mouse strains. Variations in the intensity of probe hybridization within some lanes (FIG. 1b, data not shown), however, indicate transgene mosaicism, as has been previously observed by others (see Hofmann et al., *EMBO Rep.* (2003) 4(11):1054-60, Brem et al., (1994) 179-244, Lois et al., *Science* (2002) 295(5556):868-872, Michalkiewicz et al., 2007, and Wolf et al., *Exp Physiol* (2000) 85(6): 615-625)). All founders generated with methylated T2/sh_mCFTR1 transposons examined (n=7), but only half of founders generated by nonmethylated transposons (2 of 4), transmitted at least one transgene copy to their offspring (FIG. 1c and data not shown). Notably, the reliable transmission of methylated transposons to the F1 generation contrasts an earlier study using partially methylated transgenes that observed abnormal germline transmission, transgene instability, and in some cases, abnormal offspring [see Pravtcheva et al., *Mutat Res* (2003) 529(1-2):35-50]. None of these problems were observed in the T2/sh_mCFTR1 transgenic mice.

Example 2

Transposition of a Large-Cargo Transposon in the Mouse Embryo

The significant enhancement of transposition of small transposons led us to question whether a similar enhancement would be observed in large transposon constructs. The KT2/HSA-CCTG$_{300}$ transposon is approximately 9.1 kb in length (FIG. 1a). It has been previously reported that a decrease in activity of roughly 15% per kb for transposons larger than 2 kb occurs in a colony forming assay and that 7.2- and 10.3-kb SB transposons have negligible transposition activity (see Geurts et al. (2003) *Mol Ther* 8(1):108-117)). Surprisingly, the 9.1-kb KT2/HSA-CCTG$_{300}$ was active in the mouse embryo and led to roughly 50% transgenesis (Table 1). This effectively demonstrates that large transposons can be mobilized by SB transposase. These experiments were done using a 4-fold lower number of Tn molecules given the larger size of the KT2/HSA-CCTG300 transposon. It is possible that under these conditions that Tn substrates was limiting.

Example 3

Efficient Rat Transgenesis with Methylated Transposon Substrates

Primers specific to the Bsd:GFP and miR30-Rab38 sequences were used to identify 7 transgenic founders among 11 live-born SD rat pups after injection with methylated pKT2/KDRab38 substrate and transposase mRNA (FIG. 2a). This frequency was comparable to the KT2/HSA-CCTG$_{300}$ transposon in the mouse (above) but was not compared to nonmethylated substrate. A 64% transgenesis rate by methylated TnT in SD rats is a marked enhancement over using naked DNA, which can result in transgenesis efficiencies ranging from 17-41% per live born animal in this strain (Filipiak and Saunders, *Transgenic Res.* 15:673-686 (2006)).

To verify that rat transgenesis was the result of SB transposition, linker mediated PCR (LM-PCR) was used to identify several transposition events as described by Geurts et al. (*PLos Genetics* 2:e156 (2006)). Fourteen independent transposition events were identified among six of the seven founder animals, while the remaining founder demonstrated random, nonhomologous integration of the donor transposon plasmid (data not shown). Thus, as for mouse, not only does methylation-enhanced TnT result in a 3- to 7-fold enhancement in rat transgenesis frequency (per live born animal) over standard pronuclear injection, more than one transgenic rat strain could be segregated from some founders, where traditional approaches nearly always, which almost always result in a single transgenic strain per founder. Furthermore, 4 out of 4 founders passed at least one copy of the KT2/KDRab38 transgene to their F1 offspring (data not shown) and 4 of 6 transgenic founders express the transgene by RT-PCR (FIG. 2b).

Example 4

Activity of Transposons and Recombinases in Porcine Cells

Vector Construction pT2-Floxp-PTK—To generate a multiple cloning sequence flanked by FRT and loxP recombinase recognition sequences (FRT-loxP MCS), two oligonucleotides with overlapping sequence (shown in bold) were designed, FRT-loxP Upper [ATACCGGCCGGAAGTTCCTATTCCGAAGTTC-CTATTCTCTAGAAAGTATAGGAACTTCATAACTTCG- TATAATGTATGCTATACGAAGTTATCTCGAGAATTCC-CGGGAGGCCTACTAGT] (SEQ ID NO:19), and FRT-loxP Lower [GTATTCATGAGAAGTTCCTATACTTTCTAGAG-AATAGGAACTTCGGAATAGGAACTTCATAACTTCGT-ATAGCATACATTATACGAAGTTATCCATGGACTAGTA-GGCCTCCCGGGAA] (SEQ ID NO:20). These oligonucleotides were annealed and elongated by PCR using Pwo polymerase. The 218 base pair PCR fragment was cloned into pCR4 using the ZERO BLUNT TOPO PCR CLONING KIT (Invitrogen, USA) to create pCR4FRT-loxP MCS, and its sequence was verified. FRTloxP MCS was subsequently excised with EagI and BspHI and cloned into pT2/BH (see world wide web at cbs.umn.edu/labs/perry/plasmids/plasmid.html) cleaved with EagI and NcoI to produce pT2-FRT-loxP MCS. Finally, a completely filled XhoI fragment, containing the mouse PGK promoter, the PTK fusion protein, and bovine growth hormone poly(A) signal from YTC37 (Chen and Bradley Genesis 2000, 28(1):31-35.), was cloned into SmaI cleaved pT2-FRT-loxP MCS to produce pT2-FloxP-PTK.

pKUb-SB11-A 1.0 kb fragment of the SB11 transposase from pCMV-SB11 (Geurts et al. Mol Ther 2003, 8(1):108-117), which had been amplified with CDS-SB11-F1 [CAC-CATGGGAAAATCAAAAGAAATCAGCC] (SEQ ID NO:21) and CDS-SB11-R1 [GGATCCCAATTTAAAG-GCAATGCTACCAAATACTAG] (SEQ ID NO:22) primers and subcloned into an intermediate vector adding a 5' BglII site and the sequence [AGATCTGAT] (SEQ ID NO:23), was cloned into the BamHI site of pKUb to make pKUb-SB11. pKUb was made by cloning nucleotides 3561-4771 of the human UbC gene (genbank accession D63791), which contains the UbC promoter, non-coding exon 1, and intron 1, into pK-SV40(A) between intact BglII and NheI restriction endonuclease sites. pK-SV40(A) was made by cloning a single copy of the SV40 poly(A) signal amplified by PCR with oligos KJC-SV40(A)-F1 [CATTGATGAGTTTGGA-CAAACCACA] (SEQ ID NO:24) and KJC-SV40(A)-R1 [ACCACATTTGTAGAGGTTTTACTTGCT] (SEQ ID NO:25) into pK-A10 opened with XmnI. pK-A10 was made by cloning KJC-Adapter 10 [CTGAGATCTTAAGCTAG-CAGGATCCAGAATTCATTCAG] (SEQ ID NO:26) into pK digested with PvuII creating a multiple cloning site with PvuII, BglII, AflII, NheI, BamHI, EcoRI, XmnI, and PvuII recognition sites. pK was made by joining an 0.8 kb PCR product of PBLUESCRIPTSK—(Stratagene), containing the pUC_ORI amplified with oligos KJC-pUC_ORI-F1 [CTGT-TCCGCTTCCTCGCTCACTGACT] (SEQ ID NO:27) and KJC-pUC_ORI-R1 [AAAAGGATCTAGGTGAAGATC-CTTTTTGAT] (SEQ ID NO:28), to a 0.9 kb PCR product of pENTR-D-TOPO (Invitrogen), which contains the kanamycin resistance gene amplified by oligos KJCKanR-F1 [CTG-CATCATGAACAATAAAACTGTCTGCT] (SEQ ID NO:29) and KJC-KanR-R1 [TGCCAGTGTTACAAC-CAATTAACCAAT] (SEQ ID NO:30). The junction of ORI-F1 to KanR-R1 created a single PvuII site.

pCMV-β is available from Clontech (Mountainview, Calif.).

pPGK(nls)CRE was provided by Dr. David Largaespada (University of Minnesota).

pKT2P-(nls)FLP—A Flp open reading frame containing the large T antigen nuclear localization signal (bold) and a Kozak consensuses sequence was generated by amplifying the Flp open reading frame using primers CDS Kozak-NLS Flp 5' [ATATCTCGAGGCCACCATGGCTCCCAA-GAAGAAGAGGAAGGTGATGAGTC AATTTGATATAT-TATGTAAAAC] (SEQ ID NO:31) and CDS Flp 3' [ATATA-GATCTTTATATGCGTCTATTTATGTAGG] (SEQ ID NO:32) using POG44 (Invitrogen, USA) as template. The resulting PCR product was cloned into pCR4 using the ZERO BLUNT TOPO PCR CLONING KIT (Invitrogen, USA) creating pCR4-nlsFlp. The nlsFlp open reading frame was subsequently excised with XhoI and BglII and inserted into XhoI-BglII cleaved pKT2-PGKi to produce pKT2P-nlsFlp. pKT2-PGKi contains the human PGK promoter in front of the miniintron, MCS, and rabbit beta-globin 3'UTR found in mini-CAGs.

pKT2C-EGFP was made by cloning a 0.7 kb XhoI to BglII fragment of pKT2P-GeN into pKT2-mCAG opened from BglII to XhoI. pKT2-mCAG was made by cloning a 2.2 kb BamHI to KpnI fragment of pSBT-mCAG [73] into pK-A3 opened from BamHI to KpnI. pKT2P-GeN was made by cloning EGFP as a 0.75 kb EcoRI fragment from pCR4-EGFP into the EcoRI site of pKT2P-eNeo. pCR4-EGFP was made by cloning a PCR fragment of EGFP from pEGFP-N1 (Clontech) amplified with primers KJC-EGFP-F3 [CCGAATTCTACCATGGTGAGCAAGGGCGAG] (SEQ ID NO:33) and KJCEGFP-R2 [CCAGATCTTTACTTGTA-CAGCTCGTCCATGC] (SEQ ID NO:34) into pCR4-TOPO (Invitrogen). pKT2P-eNeo contains the encephalomyocarditis virus internal ribosome entry site and neomycin resistance gene amplified from pGT-Neo with KJC-BactinSA-F1 [CACTGAAGTGTTGACTTCCCTGACAGC] (SEQ ID NO:35) and KJC-Bgeo-R1 [TTCAATTGTTAGAA-GAACTCGTCAAGAAGGCGA] (SEQ ID NO:36). The eNeo cassette was subcloned and acquired a modified sequence at the 3' end [GTTAACTT] (SEQ ID NO:37) to [GTTAAGTCTAGA] (SEQ ID NO:38) including a BglII site. The 1.4 kb eNeo cassette was isolated with EcoRI and BglII and moved into pKT2-PGKi opened from BglII to EcoRI.

pKT2P-PTK was made by cloning a 2.7 kb PvuII fragment from pKP-PTK_TS into pKT2-RV opened with EcoRV. pKT2-RV was made by cloning a 0.6 kb BamHI to KpnI fragment of pSBT-RV (Ohlfest et al., Blood 2005, 105(7): 2691-2698) into pK-A3 opened with BamHI and KpnI. pK-A3 was made by opening pK with PvuII and inserting KJC-Adapter 3 [CTGGATCCAGATCTGGTACCATTTAAAT] (SEQ ID NO:39) creating a small multiple cloning site with PvuII, BamHI, BglII, KpnI, and SwaI sites. pKP-PTK_TS was made by cloning a 2.3 kb BglII to EcoRI fragment of pCR4-PGK-PTK into the MCS of pK-SV40(×2) opened with EcoRI and BglII. pCR4-PGK-PTK was made by cloning a 2.3 kb PCR product of pT2-FloxP-PTK amplified with PuroΔTK-F1 [TTAGATCTGGCCTCGCACACATTCCA-CAT] (SEQ ID NO:40) and PuroΔTK-R1 [TGGTTCTTTC-CGCCTCAGAAGCCAT] (SEQ ID NO:41) into pCR4-TOPO (Invitrogen). pKSV40(×2) was made by cloning two copies of the SV40 poly(A) signal amplified by PCR with oligos KJCSV40(A)-F1 [CATTGATGAGTTTGGA-CAAACCACA] (SEQ ID NO:24) and KJC-SV40(A)-R1 [ACCACATTTGTAGAGGTTTTACTTGCT] (SEQ ID NO:25) into pK-A10 opened with XmnI.

pTol2-PTK—The mini Tol2 transposon donor plasmid was constructed by inserting the PvuII fragment of pKP-PTKTS into pGemT-Tol12 opened from SwaI to HindIII (filled) to produce pGTol2P_PTK.

pCMV-Tol2 was constructed as described in Balciunas et al. PLoS Genet. 2006, 2(11):e169.

pPBTP-PTK was made by cloning a 2.7 kb PvuII fragment of pKP-PTK_TS into pPBT-SE opened from SmaI to EcoRV. pPBT-SE was made by cloning the 102 by PCR product containing an outward facing T7 polymerase site, the SE multiple cloning site, and an outward facing T3 polymerase site into pPBT cut with MscI. The PCR product was amplified from pKT2-SE using T7-REVCOMP [TCTCCCTATAGT- GAGTCGTATTA] (SEQ ID NO:42) and T3-REVCOMP [TCTCCCTTTAGTGAGGGTTAATT] (SEQ ID NO:43) primers. pPBT was made by cloning the PB LTR1 and LTR2 into pKT2-SE from KpnI to BamHI. LTR1 and LTR 2 from PB were amplified from pXL-Bac-II, (Fraser et al., (1996) Insect Mol. Biol. 5(2):141-51), using PB-LTR1-F1 [TG-GATCCCAATCCTTAACCCTAGAAA-GATAATCATATTG] (SEQ ID NO:44) and PB-LTR1-R1 [GTGGCCATAAAAGTTTTGTTACTTTATAGAAG] (SEQ ID NO:45) or PBLTR2-F1 [TTGGCCATAAGTTATCACG-TAAGTAGAACATG] (SEQ ID NO:46) and PB-LTR2-R1 [TGGTACCTAGATTAACCCTAGAAAGATAGTCTG] (SEQ ID NO:47), respectively. LTR1 and LTR2 PCR products were cloned into pCR4 vector (Invitrogen) and subsequently excised by BamHI and MscI or MscI and KpnI digestion, respectively. pKT2-SE was made by cloning the 0.7 kb BamHI to KpnI fragment containing the SB inverted repeats and SE multiple cloning site from pSBTSE (Ohlfest et al., supra) into pK-A3 opened from KpnI to BamHI.

pKC-PB was made by inserting the 2.1 kb NheI to BamHI fragment of p3XP3-DsRed (Malcolm Fraser; see world wide web at piggbac.bio.nd.edu) containing the PB transposase coding sequence into the 3.2 kb BamHI to NheI fragment of pKC-SB11, which resulted in the exchange of SB11 with PB transposase.

pPTnP-PTK—A 2.7 kb PvuII to PvuII fragment of pKPPT-K_TS was cloned into the EcoRV site of pPTn2-RV to make pPTnP-PTK. pPTn2-RV was made by cloning KJCAdapter 4 [TCTCCCTTTAGTGAGGGTTAAT-TGATATCTAATACGACTCACTATAGGGAGA] (SEQ ID NO:48) into the MscI site of prePTn2(−1) creating T7 and T3 polymerase binding sites orientated out towards the inverted repeats of the PTn transposon and separated by an EcoRV site. prePPTn2(−1) was made by cloning a 0.5 kb BamHI to KpnI fragment of pCR4-PPTN2A into pK-A3 opened from KpnI to BamHI. pCR4-PPTN2A was created by topo cloning a 0.5 kb PCR product amplified from prePPTN2(−2) using oligos PPTN-F1 (BamHI) [AAGGATCCGATTACAGTGC-CTTGCATAAGTAT] (SEQ ID NO:49) and PPTN-R1 (KpnI) [AAGGTACCGATTACAGTGCCTTGCATAAGTATTC] (SEQ ID NO:50) into pCR4-Topo (Invitrogen). pre-PPTN2(−2) was created by amplifying the majority of pBluKS-PPTN5 (Leaver Gene 2001, 271(2):203-214) with oligos PPTN-OL2 [CCATCTTTGTTAGGGGTTTCA-CAGTA] (SEQ ID NO:51) and PPTN-OR1 [CCAGGTTC-TACCAAGTATTGACACA] (SEQ ID NO:52). The PCR fragment was then self-ligated to produce an empty transposon with a single MscI site in its interior.

pKC-PTs1 was made by cloning a 1.0 kb NheI to EcoRI fragment of pKUb-PTs1 that contained the PPTN transposase (PTs) into pK-mCAG opened from EcoRI to NheI. pK-mCAG was made by cloning the mCAG promoter from pSBT-mCAG (Ohlfest et al. supra) as a 0.96 kb SmaI to EcoRI (filled) fragment into pK-SV40(A)×2 opened with AflII (filled). pKUb-PTs1 was made by replacing the SB11 gene from pKUb-SB11 with PTs by cloning a 1.0 kb BamHI to NheI fragment from pCR4-PPTs1B into pKUb-SB11 from NheI to BamHI. pCR4-PPTs1B was made by cloning a PCR fragment of pBluKS-PPTN4 (Leaver, supra), amplified with primers CDS-PPTs-F1 [AAAGCTAGCATGAAGAC-CAAGGAGCTCACC] (SEQ ID NO:53) and CDS-PPTs-R1 [AAGGATCCTCAATACTTGGTAGAACC] (SEQ ID NO:54) into pCR4-Topo (Invitrogen).

pKT2C-loxPTK-G was made by cloning a 2.3 kb PvuII fragment of pK-PTK_TS into the MscI site of pKT2C-lox-GFP. pK-PTK_TS was made by cloning a 1.9 kb BglII to EcoRI fragment of pCR4-PTK into the MCS of pK-SV40(×2) opened with EcoRI and BglII. pCR4-PTK was made by cloning a 1.9 kb PCR product of pT2-FloxP-PTK using oligos PuroΔTK-F2 [TTAGATCTACCATGACCGAG-TACAAGCCCA] (SEQ ID NO:55) and PuroΔTK-R1 [TG-GTTCTTTCCGCCTCAGAAGCCAT] (SEQ ID NO:41) into pCR4-TOPO (Invitrogen). pKT2C-lox-GFP was made by cloning 0.1 kb EcoRI fragment of pCR4-loxP, which contains two direct repeat loxP sites separated with a MscI site, into pKT2CEGFP opened with EcoRI. pCR4-loxP was made by topo cloning the annealed and extended oligos loxP-F1 [ATAACTTCGTATAATGTATGCTATAC-GAAGTTATCTCGAGTGGCCA] (SEQ ID NO:56) and loxP-R1 [ATAACTTCGTATAGCATACATTATAC-GAAGTTATTGGCCACTCGAG] (SEQ ID NO:57) into pCR4-TOPO (Invitrogen).

Cell Culture and Transposition/Recombinase Assays

Pig fibroblasts were isolated from 43 day old embryos. The tissue was dissociated using a collagenase/DNAse I treatment as well as mechanical disruption. The cells from the female piglet #8 were cultured in DMEM enriched with 10% FBS and 2× antibiotic/antimycotic solution (Gibco #15240-022). The cells were passaged in DMEM high glucose media enriched with 10% FBS, 2 mm Lglutamine, 1×P/S until spontaneously establishing line PF8. A subpopulation of porcine endometrial gland epithelium cells (Deachapunya et al. J Gen Physiol 1999, 114(4):561-574) were spontaneously immortalized, strain PEGE. The PEGE cells were maintained in DMEM supplemented with 10% FCS, 1× Penn/Strep, 10 µg/ml Insulin (Sigma, USA), and 1×L-Glutamine.

For transposition assays cells were plated in each well of a six well plate to achieve 60-80% confluence within 6-24 hours. Cells were transfected using TRANSIT-LT1 (Minis Bio Corporation, Wis.) transfection reagent according to the manufacturer's instructions with a ratio of 3:1 lipid: µg DNA. Each transfection contained a total of 1.15 to 1.5 µg of plasmid DNA. Wells 1-3 contained transposon plus transposase, well 4 contained transposon with no transposase, well 5 contained SB plus SB transposase and well 6 contained pKT2C-EGFP only. Molar amounts of each transposon were fixed at $1.5 \times 10^{-13}$ moles of transposon (0.75×10-13 Moles for Tol2) while transposase plasmid was added at a molar ratio of 1:1 for SB, Tol2, and PB, and 1:0.5 for PP. The choice of the promoters and transfection ratios for SB and PP was based on the highest transposition activity observed in human HT1080 cells (data not shown). Strong promoters (CMV & mini-CAGs) and transfection conditions for Tol2 and PB were selected based on previously published data and the observation that these transposon systems seem less susceptible to overexpression inhibition than SB and PP. [Wu et al. Proc Natl Acad Sci USA 2006, 103(41):15008-15013; Wilson et al. Mol Ther 2007, 15(1):139-145; and Balciunas et al., supra). Total DNA weight was adjusted using pCMV-β plasmid. Forty-eight hours after transfection cells were trypsinized, and two replicates of 60,000 cells were plated onto 100 mm plates in media containing 0.3 µg/ml puromycin and selected for 9-12 days. Colonies were visualized by methylene blue staining and counted. A minimum of two six-well plates were transfected for each experiment. The mean colony number and standard error are shown in figures.

Southern Hybridizations

Several independent puromycin resistant PEGE foci for each transposon were aspirated and grown to confluence on a 100 mm plate. Genomic DNA was extracted using standard methods and approximately 10 µg was digested with SspI (Tol2 clones) or AseI (SB, PB, and PP) clones. Digested DNA was separated on 0.7% agarose gel and transferred to positively charged nylon membranes (GE Osmotics, USA).

Membranes were probed with a random primed 1524 bp XmaI fragment of pKP-PTK-TS that contained the bulk of the PTK gene and visualized by autoradiography or phosphor imaging.

Cloning Transposon Junctions

Genomic DNA was isolated from pooled, fixed, and stained puromycin resistant clones for each transposon. For splinkerette PCR, DNA was cut with Sau3AI or NlaIII and junctions were cloned as described by Dupuy et al. *Proc Natl Acad Sci USA* 2002, 99(7):4495-4499. For blocked linker-mediated PCR, DNA was cut with NspI for Tol2 and SB, and a cocktail of enzymes including XbaI, AvrII, NheI and SpeI for PB and PP. The NspI digested DNA was ligated to the blocked linker-SphI that was created by annealing primerette-long [CCTCCACTACGACTCACTGAAGGGCAAG-CAGTCCTAACAACCATG] (SEQ ID NO:58) and blink-SphI [5'P-GTTGTTAGGACTGCTTGC-3'P] (SEQ ID NO:59). Whereas the DNA digested with the cocktail was ligated to the blocked linker-XbaI that was produced by annealing primerette long to blink-XbaI [5'P-CTAGCATG-GTTGTTAGGACTGCTTGC-3'P] (SEQ ID NO:60). Following ligation the junction sequences were amplified by nested PCR. The primary PCR used the common primer primerette-short [CCTCCACTACGACTCACT-GAAGGGC] (SEQ ID NO:61) with transposon-specific primers SB_IRDR(L)-O1 [ATTTTCCAAGCTGTT-TAAAGGCACAGTCAAC] (SEQ ID NO:62), Tol2(L)-O1 [AATTAAACTGGGCATCAGCGCAATT] (SEQ ID NO:63), PB-LTR(R)-O1 [ACAGACCGATAAAACACAT-GCGTCAA] (SEQ ID NO:64), and PTn-IRDR(R)-O1 [GGGTGAATACTTATGCACCCAACAGATG] (SEQ ID NO:65). The secondary PCR reactions used the common primer primerette-nested [GGGCAAGCAGTCCTAA-CAACCATG] (SEQ ID NO:10) with transposon-specific primers SB_IRDR(L)-O2 [GACTTGTGTCATGCA-CAAAGTAGATGTCCT] (SEQ ID NO:66), Tol2(L)-O2 [GCGCAATTCAATTGGTTTGGTAATAGC] (SEQ ID NO:67), PB-LTR(R)-O2 [TCCTAAATGCACAGCGACG-GATTC] (SEQ ID NO:68), and PTn-IRDR(R)-O2 [CAGTA-CATAATGGGAAAAAGTCCAAGGG] (SEQ ID NO:69). To generate unique sequences serial dilutions (1:50 and 1:500) of the ligation reaction were used as template for the primary PCR. The primary PCR was diluted 1:50 and used as template in the secondary PCR reaction. The PCR fragments were shotgun cloned and sequenced.

Results

Sleeping Beauty Activity in Porcine Cells

To test the ability of the SB transposon systems to mediate transposition into the porcine genome, a transposon vector (pT2-FloxP-PTK) and a transposase expression vector (pKUb-SB11) were constructed (FIG. 3A). The transposon vector encodes a puromycin-thymidine kinase (PuroΔTK, PTK) fusion protein (Chen and Bradley, supra) between the inverted repeats of the SB transposon system. The PTK cassette was flanked by both FRT and loxP sites so that it could be used as a substrate for testing both Cre and Flp recombinases (see below). Pig fetal fibroblasts (PFF) or porcine endometrial gland epithelium (PEGE) cells were transfected with the PTK transposon along with the SB expression vector, a vector encoding non-functional SB (pKUb-SBΔDDE), or a β-galactosidase expression vector (pCMV-β). After the transfection period, cells with integrations were rendered resistant to puromycin selection, and formed clonal cell colonies after 9-12 days. Clones were stained with methylene blue and quantified (FIG. 1B). The transposase catalyzed 2.5×(PFF)-10×(PEGE) more colony formation versus transfection with a non-functional transposase (ΔDDE) or β-galactosidase. This difference in the rate of clone formation corresponds to TnT versus the background rate of non-transpositional transgenesis.

Multiple Transposon Systems Function in Porcine Cells

The success of the SB transposon system prompted investigation of three additional transposon systems. In addition to retesting the SB transposon system in PEGE cells, PP (an additional member of the Tc1 transposon family (Plasterk et al. *Trends Genet.* 1999, 15(8):326-332.), Tol2 (a member of the hAT transposon family (Kempken et al. *Chromosoma* 2001, 110(1):1-9), and PB, the founding member of the piggyBac transposon family (Sarkar et al. *Mol Genet Genomics* 2003, 270(2):173-180), were tested. PEGE cells are one of a few immortalized pig cell lines available, transfect consistently (8-15%), and form tight non-migrating clonal colonies-essential characteristics for the colony forming assays performed. The PTK expression cassette was placed between inverted repeats corresponding to each transposon; pKT2P-PTK, pPTnP-PTK, pGTol2P-PTK, and pPBTPTK, respectively (FIG. 4A). PEGE cells were co-transfected with each of these transposons along with their corresponding transposase expression construct; pKUb-SB11, pKC-PTs1, pCMV-Tol2, or pKC-PB, respectively. Each transposon vector was also co-transfected with pCMV-β to determine the background rate of non-transpositional integration. Transfected PEGE cells were placed under puromycin selection for 9-12 days, colonies fixed, stained, and enumerated. Again, transfection of PEGE cells with both components of the SB system (FIG. 4B) resulted in over 200 colonies per 60,000 plated cells, or about 3.3% of transfected cells based on an average 10% transfection efficiency. This represented a 13.5-fold increase over transfection without transposase. Similar enhancements to transgenesis were seen for all the transposon systems. PP produced an average of over 100 colonies per 60,000 cells; a 5-fold increase over transfection without transposase (FIG. 4C). The inclusion of Tol2 transposase resulted in the generation of puromycin resistant colonies at a rate 21-fold over transfections without transposase (FIG. 4D), producing on average over 240 colonies per 60,000 cells. The PB transposon system (FIG. 4E) yielded an average of over 320 colonies per 60,000 cells (about 5% of transfected cells), representing a 28-fold increase over transfection without transposase.

Molecular Characterization of Transposition

Figure 6:
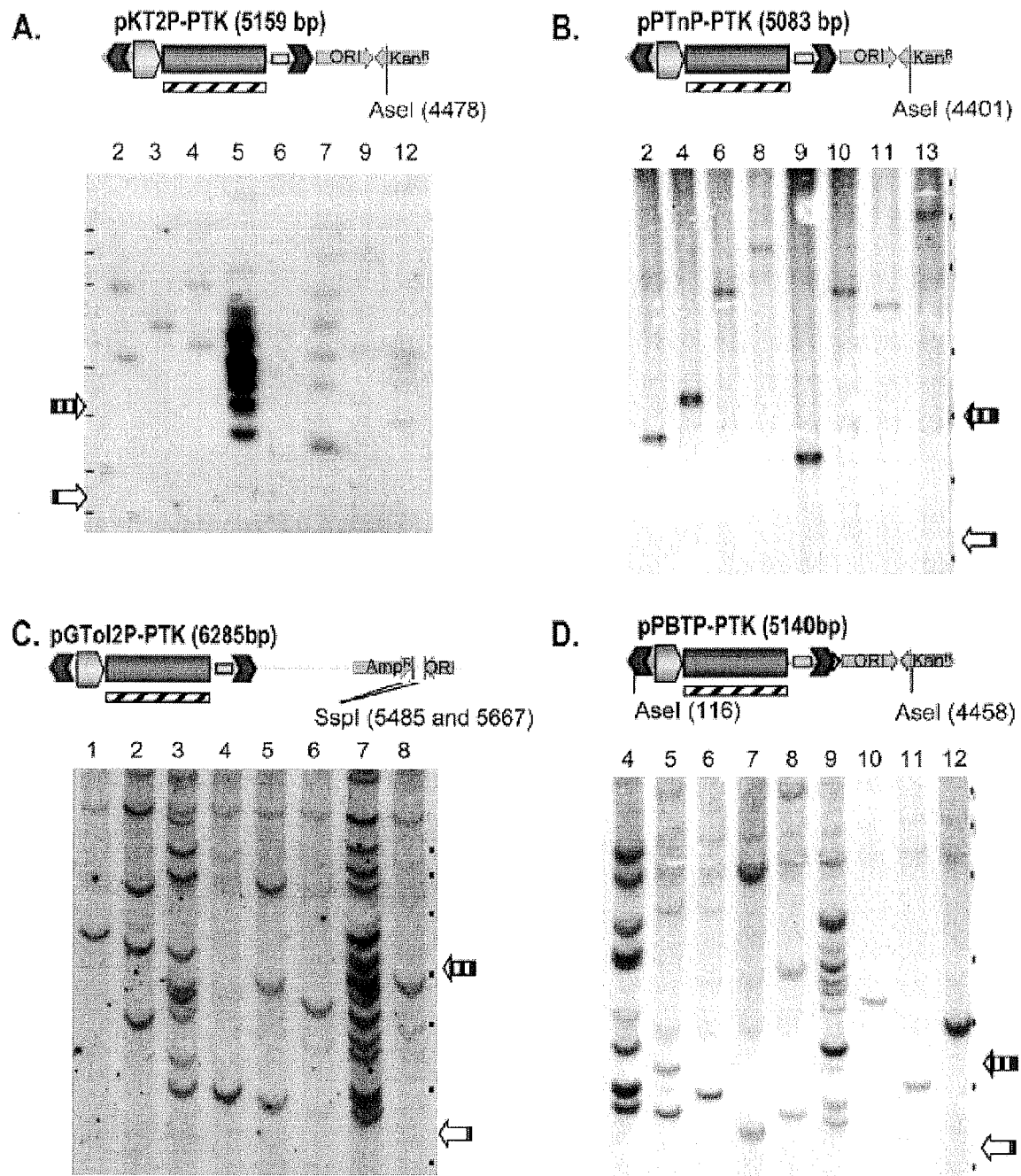
FIG. 6 contains Southern blots of PEGE Clones. Individual puromycin resistant PEGE colonies were isolated and expanded for Southern analysis A) SB B) PP C) Tol2, and D) PB. Each transposon donor plasmid transfected into PEGE cells is diagramed with restriction endonuclease sites used for DNA digestion and the probe fragment indicated (diagonal lined rectangle). Expected concatemer sizes (vertical lined arrow)/smallest possible transposition event (open arrow) for each transposon are 5159/3335 bp, 5083/3275 bp, 6285/3346 bp, and 5140/3320 bp, respectively. The positions of the marker bands are indicated by black dots on the right of each blot with sizes of 12, 10, 8, 6, 5, 4, and 3 kb are shown.

Integration of DNA transposons produces target-site duplications upon integration into the genome. Analogous to SB and other Tc1 type transposons, the target site preference for PP is a TA dinucleotide. Target-site preference for the PB transposon is a TTAA tetranucleotide (Fraser et al. *Insect Mol Biol* 1996, 5(2):141-151). Integration of Tol2 results in a target-site duplication of eight bases but does not rely on specific primary sequence, instead targeting a characteristic local deformation of DNA (Hackett et al., *Genome Biol.* (2007) 8 Suppl 1:S12). Blocked linker-mediated PCR was used to clone junction fragments after transfection of PEGE cells with each transposon system. Characteristic integration footprints were observed for each transposon system (FIG. 5). Junction sequences were compared to sequences in GenBank using BLAST. Despite the small amount of contemporaneous porcine genome sequence available, some flanking DNAs of each transposon system were found to have high identity to the pig genome, in most cases in abundant repetitive elements. This demonstrates bona fide transposition into the porcine genome for each transposon class. One characteristic advantage of transposase-mediated integration is the precise incorporation of one or more independently transposed gene expression cassettes, without adjacent plasmid vector. In order to observe representative integration events, DNA was isolated from 8 or 9 selected clones from each transposon and analyzed by Southern hybridization (FIG. 6). Non-transposase mediated integrations, often head to tail concatemer repeats, have a predictable hybridizing fragment size following restriction enzyme digestion. However, transposon mediated events have unique DNA outside of the ITRs and therefore have unpredictable and varying fragment lengths. The enhancement of transgenesis by transposition (as detected by increased colony formation) was substantiated by the presence of inserts of varying size in cellular clones, in most cases without concatemers. The level of TnT can also be measured by counting the number of independent integrations per cellular clone. The more active transposons Tol2 and PB, display multiple (up to 15) independent integration events. The wild-type PP transposon system mediated a single integration event per cellular clone, reflecting its lower activity in PEGE cells, whereas the engineered SB system displayed an intermediate number of insertions.

CRE/FLP Activity in Porcine Cells

Figure 7:
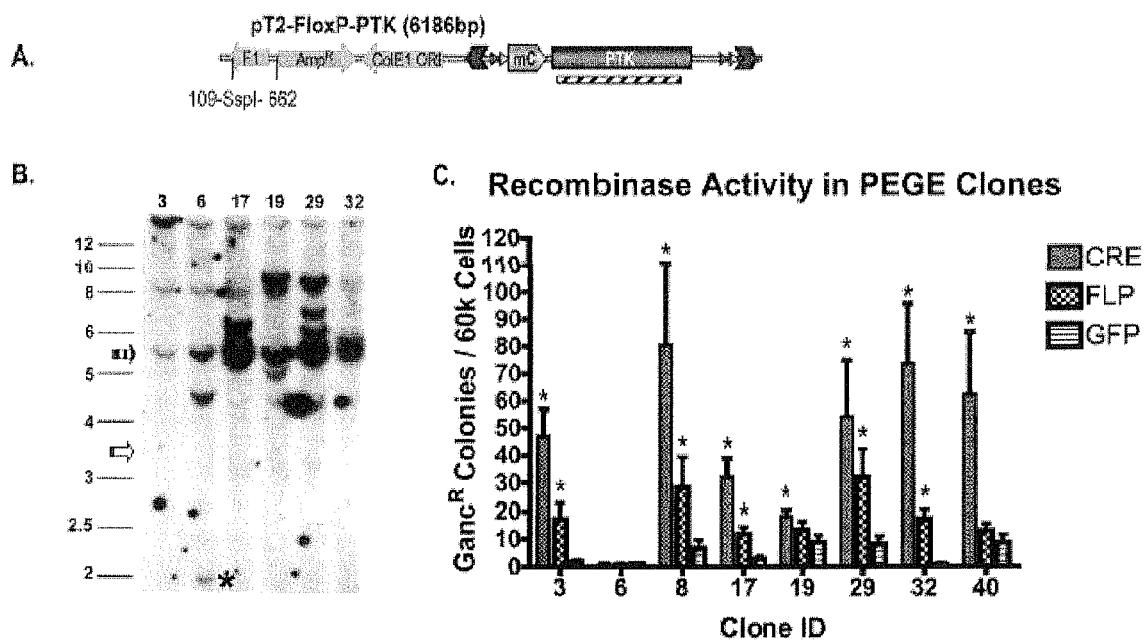
FIG. 7A-7C depict Cre/Flp Activity in Pig Cells. Individual puromycin resistant PEGE colonies were isolated and expanded for analysis. A) A diagram of the pT2-FloxP-PTK vector showing the location of restriction enzyme sites for SspI and the location of the PTK probe (diagonal lined rectangle). B) Southern analysis shows the number and size of vector inserts in several PEGE clones. The expected concatemer size of 5.6 kb (vertical lined arrow) as well as the smallest possible transposition event (open arrow) of 3.3 kb are indicated on the left of the image. An asterisk is placed to the right of a band slightly smaller than 2 kb in lane 2 (Clone #6). C) The rate of gancyclovir resistant colony formation after transfection of PEGE clones with pPGK-nlsCre (CRE), pKT2-nlsFlp (FLP), or pKT2C-EGFP (GFP). Values that are significantly different from the background (GFP) as determined by an unpaired t-test (p=0.05) are designated with an asterisk (*).

To test the ability of Cre and/or Flp recombinase to function in porcine cells, pT2-FloxP-PTK (FIG. 3A) was transfected into PEGE cells along with SB. These clones were obtained from preliminary transfections that were selected under very stringent drug conditions that favored high-copy integrations, particularly non-transposition events. DNA from puromycin resistant clones was isolated and analyzed by Southern hybridization. Isolated clones contained multiple copies of the PTK transgene due to non-transpositional integration, as indicated by concatemers and concatemer junction bands (FIG. 7). PTK transgenic clones were subsequently transfected with pPGKnlsCre, pKT2P-nlsFlp, or pKT2C-EGFP. Excision of the PTK cassette was detectable in transiently transfected cells by PCR, and the sequence of the excision product confirmed by sequencing (data not shown). Transfected cells were placed under selection with gancyclovir for 10-14 days and colonies counted (FIG. 7C). Only cells that had excised the PTK gene could withstand gancyclovir selection.

As expected for concatemers, we observed a low level of transgene instability as evidenced by the appearance of gancyclovir resistant clones upon transfection with pKT2C-EGFP. A much more pronounced recombinase stimulated elimination of the PTK cassette was demonstrated by elevated resistant colony formation for 7 out of 8 of the clones transfected with either pPGK-nlsCre or pKT2P-nlsFlp. While Cre and Flp are both active in PEGE cells, in all cases Cre mediated recombination/excision matched or exceeded that observed for Flp. A single clone (#6) never showed evidence of PTK elimination. The Southern analysis (FIG. 7B), revealed a fragment of pT2-FloxP-PTK likely resulting from the integration of a shortened PTK expression cassette lacking at least one flanking RRS. This clipped PTK transgene is therefore unable to be removed by recombinase-mediated excision.

CRE-Activated Gene Expression

To further demonstrate the functionality of the transposon based Cre recombinase system for use in porcine genome engineering, a SB transposon containing a Creactivated gene expression cassette was constructed—pTCloxPTK-G (FIG. 8A). The PTK gene would be transcribed by the mini-CAGs promoter and efficiently terminated by three complete poly (A) signals (triple stop) in the intact pTC-loxPTK-G (Vallier et al. *Proc Natl Acad Sci USA* 2001, 98(5):2467-2472.). Cre recombination results in deletion of the PTK/triple-stop cassette, thereby juxtaposing the mini-CAGS promoter and the downstream gene expression cassette and enabling transcription of the green fluorescent protein (GFP) gene.

Conditional activation of GFP expression was assessed by microscopy and flow cytometry after transient transfection of PEGE cells with pTC-loxPTK-G in the presence or absence of pPGK-nlsCRE (FIG. 8B). There was no GFP observed in cells transfected with pTC-loxPTK-G alone, whereas about 10-12% of the cells were GFP+ when transfected with pPGK-nlsCre. This corresponds well with the average transfection efficiency of PEGE cells, indicating that the Cre excision reaction is very efficient in transiently transfected cells.

To further examine the efficiency of Cre recombinase in transiently transfected cells, conditional removal of the PTK/triple stop expression cassette was assessed by selection in puromycin following co-transfection of PEGE cells with pTC-loxPTK-G and either Cre, β-galactosidase, SB, or Cre+SB. Transfected cells were plated under puromycin selection for 9-12 days, stained with methylene blue, and enumerated to quantify the efficiency of PTK/triple stop elimination prior to or after integration into the genome (FIG. 8C). Addition of pPGK-nlsCRE to the transfection, alone or in combination with pKUb-SB11 reduced puromycin-resistant colony counts to levels significantly lower than that observed for pKUb-SB11 or pCMV-β, which alone result in TnT and non-transpositional transgenesis with an intact PTK gene expression cassette, respectively. Therefore, Cre recombinase excision activity in transiently transfected PEGE cells approaches 100%, especially with regard to plasmids available for transposition by SB transposase.

Although this particular co-transfection with pTC-loxPTKG and SB suffered from a low transfection efficiency (~5%) that reduced TnT (compare FIG. 8C to 3B), puromycin resistant clones were expanded for characterization by Southern hybridization (FIG. 9). Analysis indicated TnT with 1 to 4 transposon integrations per clone. Although, clones 7, 10 and perhaps 11 contained hybridizing species near what would be expected for non-transpositional integration, their molar representation was equal to that of single copy inserts, not multicopy concatemers. Clones 7 and 10 also harbored hybridizing species smaller than was expected for transposition. These fragments likely represent non-transposase mediated DNA recombination events. The proportion of non-transpositional integrations detected by Southern analysis (1 in 4) corresponds well with the observed unfacilitated rate of transgenesis as determined by colony count for this transfection.

pTC-loxPTK-G clones were generated to analyze the efficiency of recombinase-directed selection-cassette recycling and the conditional activation of gene expression from a variety of porcine genomic loci. Puromycin resistant clones were transfected with pPGK-nlsCRE and scored for gancylovir resistance (FIG. 9C). All gancylovir resistant clones expressed GFP, although variation in the intensity of GFP was observed (data not shown) depending on the parental clone source. This expression variance is expected due to the influence of porcine sequence adjacent to the sites of transposon integration, a phenomenon commonly referred to as "position effect". A significant increase in the efficiency of selection cassette recycling was demonstrated in the presence of single copy inserts when compared to multicopy concatemers (FIG. 9C vs 7C). In addition, activation of GFP expression upon recombinase-based excision from integrated transposons demonstrates the efficacy of Cre-dependent conditional gene expression in transgenic porcine cells.

Example 5

Genome Integration in Parthenogenetic Pig Embryos

To determine if SB was active in pig embryos, parthenogenetic pig embryos were injected with two methylated SB transposons KT2H-YFClinear and KT2C-mCherrysupercoiled (FIG. 10a) along with in vitro transcribed, capped SB transposase mRNA. Injected embryos were cultured for 7 days post injection resulting in a mixture of 1-cell to blastocyst stage embryos and reserved for characterization. In order to study transgenesis in individual embryos, a method for genomic DNA characterization was developed. An individual embryo is expected to be comprised of from 1 to a few hundred cells, depending on developmental stage (1-cell to hatched blastocyst).

The whole genome amplification (WGA) protocol of Luthra et al. (*J Mol Diagn* 2004, 6(3):236-242) was modified for assessment of transgenesis in pig embryos. Using rolling circle replication, picograms of genomic DNA can be amplified to 40 µg in a non-biased manner. Of importance for genomic characterization, the average size of the amplification product from this procedure is around 12 kilobases which is suitable for Southern analysis of single-copy genes. See Papaioannou et al., *Development* 1988, 102(4):793-803; Luthra et al., *J Mol Diagn* 2004, 6(3):236-242, and Pinard et al., BMC genomics [electronic resource] 2006, 7:216).

Figure 10:
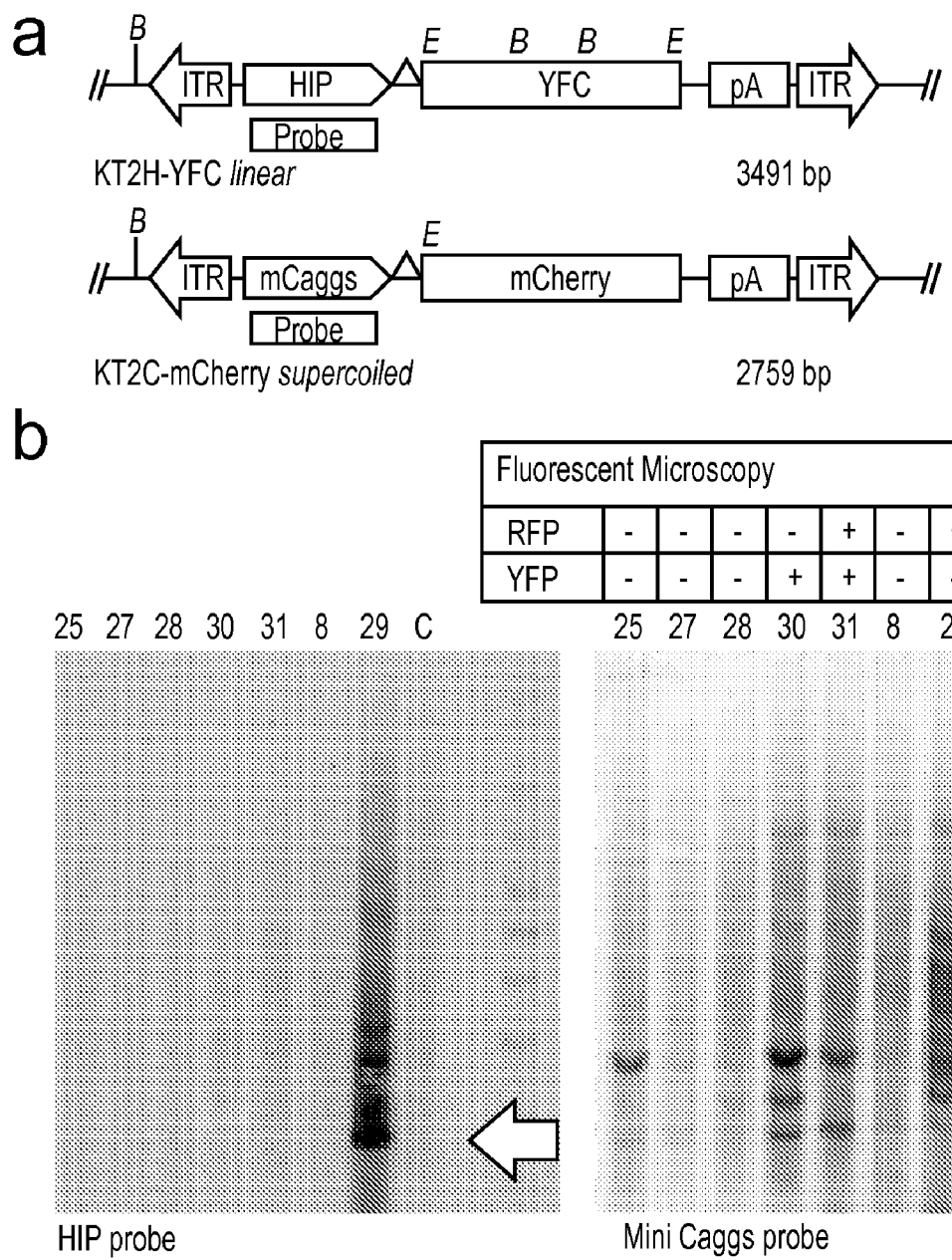
FIG. 10a is a schematic of the KT2H-YFC transposon, which is designed to express a fusion of yellow fluorescent protein and Cre recombinase from the human insulin promoter (HIP). Expression from this promoter should be limited to insulin producing cells in the pancreas. The KT2C-mCherry transposon expresses a modified version of red fluorescent protein mCherry from the ubiquitous miniCags (mCags) promoter. The transposons were prepared for injection either by cutting once in the vector backbone to linearize, KT2H-YFC, or by leaving the plasmid supercoiled KT2C-mCherry. Both transposons were CpG methylated in vitro and mixed at an equal molar ratio along with 15 ng/µl of in vitro transcribed, capped SB mRNA.
FIG. 10b are photographs of WGA Southern blotting. Prior to embryo freezing, blastocyst stage embryos were examined by fluorescent microscopy. WGA Southern blotting was performed on seven blastocysts and a non-amplified DNA control (C). DNA was cut with BamHI (B) and EcoRI (E) and probed with the HIP or miniCags probe fragment (FIG. 2A) as indicated on the Southern. The arrows mark the expected band liberated from for non-facilitated concatemer integration.

The ability to detect integrations from cultured cells known to contain SB transposons was assessed. WGA-Southern blotting was capable of detecting transposon integration from as few as 5 cells. To test transposition in early embryos from pilot experiments, four 1-cell embryos were pooled for WGA and LM-PCR. Cloning and sequencing revealed eight independent intra-plasmid transposition events (data not shown). Intra-plasmid transposition is commonly in transposition assay, and although it does not demonstrate integration into the genome, here definitively demonstrates transposition in the 1-cell pig embryo. Furthermore, WGA was independently conducted using seven randomly selected blastocyst stage embryos, and Southern analysis was conducted using probes specific to the HIP and miniCags promoters present in the two transposons tested (FIG. 10B). Several embryos displayed hybridizing bands corresponding to the miniCags promoter, while embryo 29 displayed unique bands corresponding to both transposons. These results demonstrate TnT into the pig genome using the SB transposon system. Furthermore, these results were validated by LM-PCR/sequencing. In close alignment with the Southern analysis, 4-right and 3-left transposon-genome junctions were recovered from embryo 29 (Table 3). Genomic sequence flanking transposon insertions was analyzed by BLAST and revealed to represent 7 independent transposition events, one of which serendipitously integrated upstream of the pig myostatin gene.

TABLE 3

Pig genome integration sites

| | Genome sequence | IR/DR L | Best Match | E-values (b-score) | Location (species) |
|---|---|---|---|---|---|
| Vector Left | CAGCTGGATCCAGATCCCTA TA (SEQ ID NO: 70) | CAGTTGAAGTC (SEQ ID NO: 71) | | | |
| Junction 1 | CTACCTCAAGATAACATAGC TA (SEQ ID NO: 72) | CAGTTGAAGTA (SEQ ID NO: 73) | AL031407.3 | 2e-05 (56.5) | Chromosome 6p22.1-23 (Human) |
| Junction 2 | TGAAAAATAATTGGAACAAA TA (SEQ ID NO: 74) | CAGTTGAAGTA (SEQ ID NO: 73) | AM710396.1 | 2e-11 (78.7) | Androgen receptor (Macaque) |
| Junction 3 | TTCGGAAGATGTGGTATATA TA (SEQ ID NO: 75) | CAGTTGAAGTA (SEQ ID NO: 73) | EF599954.1 | 0 (867) | *Sus scrofa* retrotransposon L1 (Pig) |
| Junction 4 | TTTATCTATCAAAACACATC TA (SEQ ID NO: 76) | CAGTTGAAGTA (SEQ ID NO: 73) | DQ020484.1 | 4e-11 (76.8) | *Sus scrofa* BAC KNP_217F2 (Pig) |

| | IR/DR R | Genome sequence | Best Match | E-values (b-score) | Location (species) |
|---|---|---|---|---|---|
| Vector Right | GACTTCAACTG (SEQ ID NO: 77) | TA TAGGGATCTGGTACCATTTA (SEQ ID NO: 78) | | | |
| Junction 5 | GACTTCAACTG (SEQ ID NO: 77) | TA TATACACAATGGAATACTAC (SEQ ID NO: 79) | AY208121.1 | 2e-149 (536) | *Sus scrofa* myostatin gene (Pig) |
| Junction 6 | GACTTCAACTG (SEQ ID NO: 77) | TA TATAAAAAAATGTCTGCTCC (SEQ ID NO: 80) | XM_848959.1 | 7e-34 (152) | *Canis familiaris* DNA sequence |
| Junction 7 | GACTTCAACTG (SEQ ID NO: 77) | TA TAGAGACAGACCTGGAAAGG (SEQ ID NO: 81) | AL513165.12 | 0.001 (52.8) | Human DNA sequence |

Example 5

Transgene Methylation Status and Transcriptional Activity

Cytosine methylation is an essential epigenetic modification to all vertebrate genomes and is developmentally regulated. In the early embryo, the paternal genome undergoes active, non-specific demethylation, while methylation of the maternal genome depletes with every cell division until the morula stage, but not to the same extent of the paternal genome (Armstrong et al. *Stem Cells* 24:805-814 (2006)). Thus, integration would be expected to erase synthetic methylation of transposons during development of the early embryo. Nevertheless, endogenous hypermethylation of cytosine residues can cause silencing of transgenes in animals (Chevalier-Mariette et al., *Genome Biology* 4:R53 (2003); Betzl et al. *Biol. Chem.* 377:711-9 (1996); Schumacher et al., *J. Biol. Chem.* 275:37915-37921 (2000)). Thus, transposon transgenes were analyzed in several founder mice to assess both their methylation status and transcriptional activity.

Figure 11:
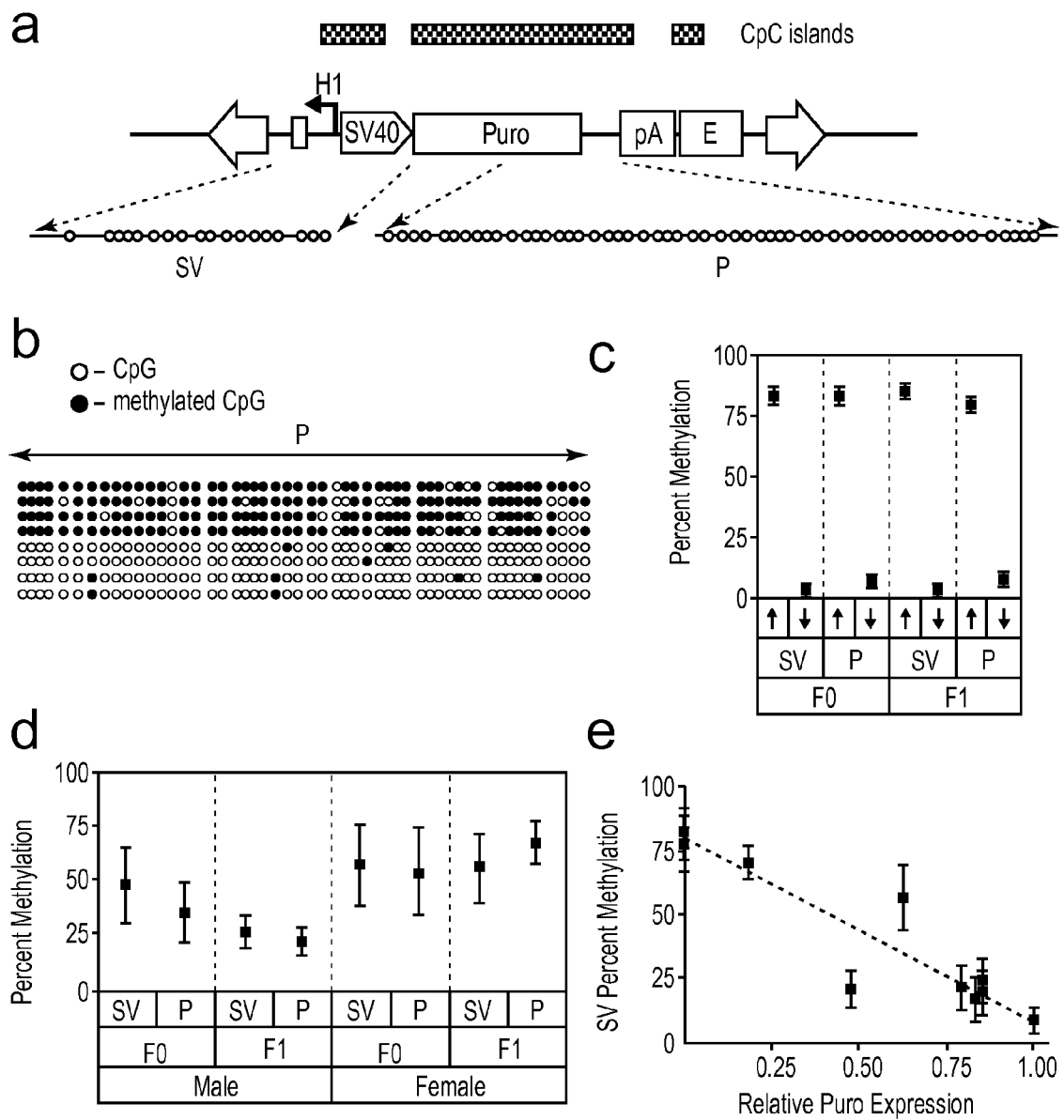
FIG. 11 depicts methylation of T2/sh_mCFTR1 transposons in founder and F1 animals. a) Three CpG islands are found in the T2/sh_mCFTR1 transposon (hatched boxes). Two amplicons, SV and P, overlapping the SV40/H1 promoter and Puro coding regions were analyzed for methylation in transgenic founder and F1 DNA. b) Methylation was largely bimodal, showing almost complete methylation or lack thereof from transgene to transgene. c) Data was accumulated for 52 SV and 67 P amplicons from founder animals and 112 SV and 170 P amplicons from F1 animals. Dividing the pattern into two groups with greater or less than 50% methylation revealed little variation from this bimodal pattern with a 95% confidence interval. d) Some variation in the percent methylation across the transgene was attributable to significant differences between methylation patterns in offspring from male or female founders in both the SV and P regions (p<0.05, Mann-Whitney test). e) Among F1 animals that carried a single transgene insertion, as determined by Southern blot (see FIG. 3), a significant correlation between percent methylation and normalized Puro expression was found (n=9, p<0.05, linear regression analysis).

FIG. 11A shows CpG-rich regions of T2/sh_mCFTR1 and two segments (SV and P) examined by bisulfate sequencing on DNA extracted from the liver of transgenic mice. Since the methylation patterns could vary from transgene to transgene, multiple ($\geq 5$) independently isolated PCR fragments were sequenced for each animal. The distribution of methylation in F0 and F1 offspring indicates that methylation status is reset in the early embryo (FIG. 11B). Percent methylation of individual transposon insertions was bi-modal, either hyper or hypomethylated in each founder (FIG. 11C), in concordance with known character of the mammalian epigenome (Eckhardt et al. *Nat. Genet.* 38:1378-1385 (2006); Rakyan et al. *PLoS Biology* 2:e405 (2004)). Interestingly, a significant increase in the overall level of transgene methylation was observed in female founder animals and their offspring compared to male founders and their offspring (FIG. 11D). The T2/sh_mCFTR1 transposon expresses a hairpin RNA against Cftr using the human H1 promoter (transcribed by Pol III), and puromycin N-acetyltransferase (puro) using the SV40 promoter (transcribed by Pol II) (FIG. 1A). Because the SV40 promoter is not active in mouse hepatocytes, small intestine samples from all F0 single and multi-copy transgenics were probed by quantitative RT-PCR for puro expression. Puro was detected in every animal, regardless of whether the injected transgene(s) had been synthetically methylated before injection (data not shown). This likely reflects mosaicism of transgenesis (and thus endogenous methylation) in founders. F1 offspring were examined from multiple founders, each carrying a single copy of the transgene (as determined by Southern), and found significant correlation between puro expression and % methylation of the SV region (FIG. 11E).

The expression of the sh_mCFTR1 hairpin measured between 2,000 and 10,000 copies per cell in lung and liver samples from two founder animals and their F1 offspring (data not shown). Despite variable levels of sh_mCFTR1, several mouse lines display functional consequences of Cftr knockdown, including impaired chloride transport and reduced fertility. In summary, due to the epigenetic reprogramming during embryogenesis, TnT with methylated transposon transgenes is an efficient method for generating transgenic animals that express their transgene cassettes in a manner consistent with their position of integration, not with their synthetic modification before injection.

Example 6

Cre Regulated APOBEC-G Transgenic Cell Lines

Three Sleeping Beauty transposons were constructed and are referred to generically as pKT2X-LP2-PTK-APOBEC-G in FIG. 12A, where X refers to three ubiquitous promoters; miniCags, ubiquitin, or PGK ranging from high to low expression. Each transposon was separately introduced into K815 adult male fibroblast cells at a 2:1 molar ratio with the Sleeping Beauty transposase expression plasmid pKC-SB100X (FIG. 12B). Transposition was selected for based on puromycin resistance provided by the floxed puroΔTK (PTK) gene positioned downstream of the promoter and immediately upstream of the human APOBEC-G cDNA. Provision of Cre recombinase either transiently, or in the context of mating to a Cre-transgenic pig, removes the foxed PTK gene, while simultaneously activating expression of the hAPOBEC-G gene (FIG. 12A). Transgenic cells were selected on a population level, and determined to contain 1-5 unlinked copies of the transposon, corresponding to between 400-2,000 independent insertions into the pig genome.

Co-Transposition for Creating APOBEC-G Cell Lines:

For constitutive expression of APOBEC-G, pKT2P-APOBEC-G was constructed driving APOBEC-G from the ubiquitous PGK promoter. To avoid confounding effects of expressing an antibiotic resistance gene from the same loci, this construct was designed without a selectable marker. Rather, two transposons, pKT2P-APOBEC-G and pKT2P-PTK (at a ratio of 5:1), were transfected into K815 adult male fibroblasts with the transposase expression construct pKC-SB100X (at a molar ratio of two parts transposons, one part transposase) (FIG. 12B). Due to the proclivity of multiple transposon insertions per selected clone, a high proportion of the puromycin resistant clones were expected to also contain unlinked copies of the pKT2P-APOBEC-G transposon. Subsequently, the puromycin transposon can be segregated from the APOBEC-G transposon by standard breeding. A PCR assay showed that 97.5% (n=40) puromycin resistant clones also contain APOBEC-G. These clones have been expanded to characterize expression level and copy number of the APOBEC-G transposon by Southern blotting. Additionally, pooled resistant cells have been cryo-preserved and represent 400-2,000 independent insertions of APOBEC-G transposon.

Example 7

Transposon Co-Transfection YFP-Cre (YFC) Cell Lines

Figure 12C:
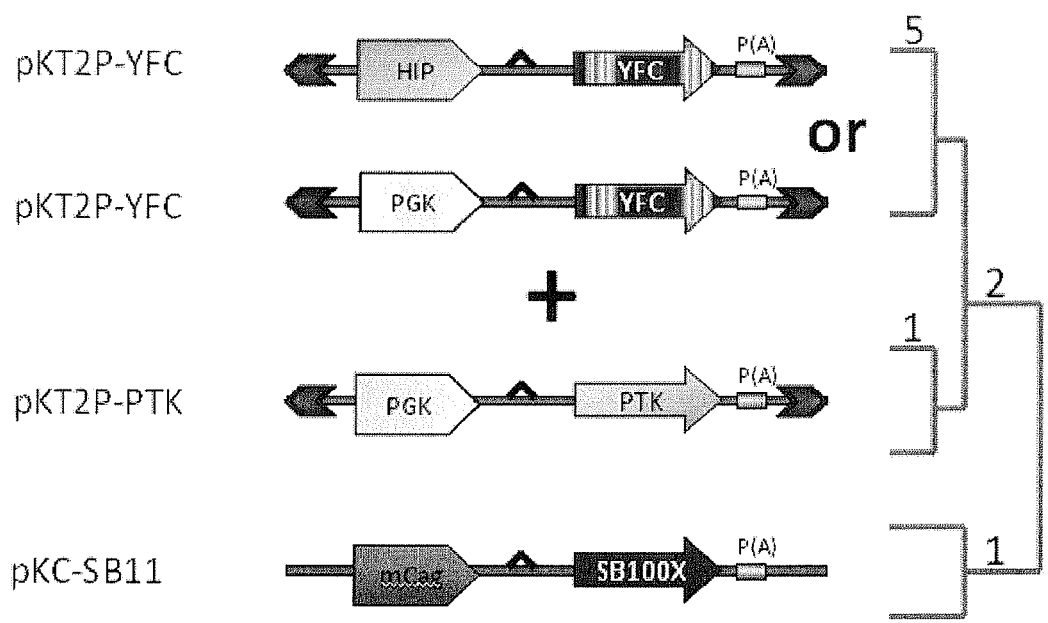
FIG. 12C is a schematic of the YFC expression plasmids and transfection scheme. Two transposons, either pKT2H-YFC or pKT2P-YFC and pKT2P-PTK, were simultaneously transfected into cells at a 5:1 ratio in trans with pKC-SB100X for a total of 2 parts transposon to 1 part transposase. Cells were selected in medium containing puromycin and assayed for co-retention of both PTK by selection and YFC transposons by PCR.

For constitutive ubiquitous and tissue specific expression of YFC, two transposons were constructed; pKT2P-YFC, PGK promoter drives ubiquitous expression and pKT2H-YFC, human insulin promoter restricting expression to β cells. To avoid confounding effects of expressing an antibiotic resistance gene, these constructs were designed without a selectable marker. Rather, pKT2P-YFC or pKT2H-YFC were co-transfected with a selectable transposon, pKT2P-PTK, plus pKC-SB100X at a molar ratio of 5:1:3 ratio (two parts transposon, one part transposase) respectively (FIG. 12C). Due to the proclivity of multiple transposon insertions per selected colony, a high proportion of the puromycin resistant clones were expected to also contain unlinked copies of the YFC transposons. Subsequently, the puromycin transposon can be segregated from the YFC transposons by standard breeding. A PCR assay showed that 93.1% (n=27) and 89.2% (n=25) of selected colonies contained pKT2P-YFC and pKT2H-YFC respectively. These clones have been expanded to characterize expression level (pKT2P-YFC only since the human insulin promoter is not active in fibroblasts) and copy number of the YFC transposons by Southern blotting. Additionally, pooled resistant cells have been cryo-preserved and represent 400-2,000 independent insertions for each transposon.

Example 8

Tet-Regulated RNAi of Porcine CFTR

Two tet-regulatable shRNA expression vectors, pKT2C-KeN-H1x and pKT2C-KM2eN-H1x, were created based on designs used in Szulc et al. (*Nat. Methods*. 2006 3(2):109-16), where regulated RNAi was observed both in vitro and in vivo. Regulation of shRNA expression in these vectors relies on expression of tTR-KRAB and rtTR-KRAB2S-M2, fusion proteins between the bacterial tetracycline repressor, allowing specific binding to tet operator (TRE) sequence, and Krüppel-associated box domain (KRAB), a repressor of gene expression. Association of these fusion proteins with TRE is dependent on the presence, pKT2C-KeN-H1x (tet-on) or absence, pKT2C-KM2eN-H1x (tet-off) of doxycycline thus providing systems where transgenes are expressed or silenced respectively in the presence of doxycycline (FIG. 13). Conversely, when doxycycine is removed, expression is silenced in pKT2C-KeN-H1x and activated in H1x. Two shRNA's (shCFTR1 and shCFTR3) previously shown to reduce the transcript and function of porcine CFTR {Palmer et al., *J Cell Physiol*. 2006 206(3):759-70} were cloned downstream of the human H1 promoter in both tet-on and tet-off versions resulting in pKT2C-KeN-shCFTR1 or 3 and pKT2C-KM2eN-shCFTR1 or 3. These constructs were transfected into female pig cells accompanied by Sleeping Beauty expression plasmid pKC-SB100X at a molar ratio of 2:1. Cells transfected with tet-on versions were selected in medium containing G-418 and doxycycline while tet-off versions were selected in G-418 only. To verify shRNA expression was regulatable, G-418 resistant pools for each vector were cultured in the presence and absence of doxycycline for 14 days and assayed for expression levels of shCFTR1 or 3. Expression of shCFTR 1 was highly regulated by both tet-on and tet-off versions (64 and 67 fold change respectively) while shCFTR3 was less responsive to doxycycline (25 and 9 fold respectively). Absolute expression levels were higher for shCFTR1 than shCFTR3 in the induced state for both tet-on and tet-off versions (FIG. 13C).

Several transgenic pig fibroblast clones were developed and characterized for shRNA expression by quantitative PCR. See FIGS. 14A and 14B. The seven cells lines depicted in FIG. 14B were selected with a range of shRNA expression for cloning by CFTR.

Enucleation and Donor Cell Transfer. Cumulus enclosed oocytes provided by BOMED are washed in HEPES buffered NCSU-23 medium and cultured (matured) in 50 T1 drops of Medium 199 (supplemented with 0.1% PVA, 0.5 ug/ml LH, 0.5 ug/ml FSH and 10 ng/ml EGF) for an additional 20 h under a 5% $CO_2$ in air atmosphere. Immediately prior to enucleation, expanded cumulus and corona cells are removed by blunt dissection and repeated pipetting of the ova in HEPES buffered NCSU-23 supplemented with 0.1% hyaluronidase. Groups of ova are transferred into 5 T1 droplets of HEPES buffered NCSU-23 containing 10% fetal calf serum, 2.5 µg/ml cytochalasin B (CB) and 5 Tg/ml Hoechst 33343, which have previously been arranged in a column on the lid of a 9 mm×50 mm Petri dish. Enucleation is achieved by physically removing the polar body and adjacent cytoplasm, which should contain the metaphase II plate, using an ES cell transfer pipette. Successful enucleation is confirmed by staining the isolated cytoplasm with 5 µg/ml Hoechst 33342. Donor cells are synchronized in presumptive G0/G1 by serum starvation (0.5%) for 24 to 72 h. Microdrops containing oocytes are spiked with a small volume of donor cells that have been trypsinized not more than 3 h prior to enucleation. Whole cell transfer is accomplished by using an ES cell transfer pipette (Eppendorf) with a sharp, beveled tip (inner diameter 20 µm).

Fusion and Activation of oocytes. Donor cells were injected into the perivitelline space and pressed against the oocyte's membrane. Cell-cytoplast couplets were fused within 2 h after enucleation. Groups of 5-10 couplets were manually aligned between the electrodes of a 1 mm gap fusion chamber (BTX) overlaid with mannitol fusion medium. Couplets were fused by exposure to a single pulse of 150 V/mm for 60 us. Following fusion, couplets were cultured in HEPES buffered NCSU+10% fetal calf serum from 0.5 to 1.5 h before activation. Couplets were activated by placing them in 1 mm gap fusion chamber overlaid with mannitol medium supplemented with 0.1 mM $CaCl_2 \times 2H_2O$ and exposing them to two 60 us pulses of 150V/mm.

Embryo transfer. Pubertal crossbred gilts aged 8 to 10 months were synchronized with Regumate (containing 0.4% altrenogest; 10 mg/day; Intervet, Boxmeer, Netherlands) mixed in commercial feed and given each morning for 17-19 days. All recipient gilts were injected with 1,000 IU PMSG (Folligon & Chorulon) and 80 h later with 500 IU hCG (Folligon & Chorulon). To produce cloned pigs, reconstructed embryos were surgically transferred into the oviducts of synchronized foster mothers by 20-24 h after activation. An ultrasound scanner with an attached 3.5 MHz transabdominal probe were used to check pregnancies at 25 and 35 days after embryo transfer. Pregnant recipients were reexamined by ultrasound again at approximately 30 days prior to the expected date of parturition. One week prior to the date of projected farrowing, all gilts were moved to farrowing crates and pigs delivered by either natural delivery or hysterotomy as dictated by labor and animal conditions.

Animals produced. 1,000 embryos were reconstructed and transferred to 9 recipients. One (1) surrogate gave birth to 7 healthy transgenic founder female piglets.

Other Embodiments

It is to be understood that while the invention has been described in conjunction with the detailed description thereof, the foregoing description is intended to illustrate and not limit the scope of the invention, which is defined by the scope of the appended claims. In general, the embodiments are illustrated by describing particular combinations of features that may be mixed-and-matched to produce other combinations as guided by the need to make a functional embodiment of the invention.

What is claimed is:

1. A method for making a transgenic pig, said method comprising:

preparing a pig egg with an in vitro hypermethylated transposon that comprises a transcriptional unit comprising a regulatory region operably linked to a target nucleic acid sequence, said transposon being inserted into a genome of the egg;

transferring said egg to a recipient female; and allowing said egg to develop in said recipient female to produce said transgenic pig, wherein the pig is gestated in the female and expresses the target nucleic acid sequence.

2. The method of claim 1 wherein preparing the pig egg comprises introduction of the transposon and a transposase into a single-cell fertilized egg, with the transposase inserting the transposon into the genome.

3. The method of claim 1 wherein preparing the pig egg comprises enucleation of the egg followed by transfer of a nucleus of a somatic pig cell into the egg, with the transferred nucleus comprising the gene and the transposon inserted into the genome.

4. The method of claim 1 wherein preparing the pig egg comprises transfer of chromatin of a somatic pig cell into the egg, with the chromatin of the somatic cell comprising the transposon.

5. The method of claim 1 wherein the hypermethylated transposon comprises hypermethylation between inverted terminal repeats of the transposon.

6. The method of claim 1 wherein all cytosine-phosphodiester-guanine sites in the transposon are methylated.

7. The method of claim 1 wherein at least 90% of cytosine-phosphodiester-guanine sites in the transposon are methylated.

8. The method of claim 1 wherein said transposon is selected from the group consisting of Sleeping Beauty, Tol2, PiggyBac, Frog Prince, Minos, and Hsmar1.

* * * * *